United States Patent
Nelson et al.

(10) Patent No.: US 6,855,337 B1
(45) Date of Patent: Feb. 15, 2005

(54) BEAR DERIVED ISOLATE AND METHOD

(75) Inventors: Ralph A. Nelson, Urbana, IL (US); Patricia G. Miers, Camarillo, CA (US); Kenneth L. Rinehart, Urbana, IL (US)

(73) Assignee: Carle Development Foundation, Urbana, IL (US)

( * ) Notice: Subject to any disclaimer, the term of this patent is extended or adjusted under 35 U.S.C. 154(b) by 255 days.

(21) Appl. No.: 10/232,880

(22) Filed: Aug. 30, 2002

Related U.S. Application Data

(63) Continuation of application No. 08/833,096, filed on Apr. 4, 1997, now abandoned, which is a continuation-in-part of application No. 08/470,750, filed on Jun. 6, 1995, now abandoned, which is a continuation-in-part of application No. 08/259,788, filed on Jun. 14, 1994, now abandoned, which is a continuation-in-part of application No. 08/079,089, filed on Jun. 16, 1993, now abandoned.

(51) Int. Cl.$^7$ ................................................ A61K 35/16
(52) U.S. Cl. ...................................... 424/531; 424/543
(58) Field of Search ................................. 424/531, 543

*Primary Examiner*—Jean C. Witz
(74) *Attorney, Agent, or Firm*—McDermott, Will & Emery

(57) ABSTRACT

A bear derived isolate found in denning black bears or black bears from which food has been withheld for at least two weeks when injected into another mammal produces reduced heart rate, reduced respiratory rate, reduced temperature, and a wakeful tranquility not unlike the phenomena of the denning black bear. The isolate is taken from either the serum or urine of such denning bear. The method of the invention involves the steps of fractionating the serum or urine of a denning black bear to produce fractions of varying potency.

22 Claims, No Drawings

BEAR DERIVED ISOLATE AND METHOD

CROSS-REFERENCE TO RELATED APPLICATIONS

"The present Application is a Continuation of pending application Ser. No. 08/833,096, filed Apr. 4, 1997 now abandoned; which in turn is a Continuation-In-part of application Ser. No. 08/470,750, filed Jun. 6, 1995, abandoned; which Application in turn is a Continuation-In-Part of Application Ser. No. 081259,788, filed Jun. 14, 1994, abandoned; which in turn is a Continuation-In-Part of original application Ser. No. 08/079,089, filed Jun. 16,1993, abandoned."

FIELD OF INVENTION

The present invention relates to the discovery and isolation of a substance called bear derived isolate (BDI) which can be found in fasting and denning black bears which, in combination and with various carriers and various doses, based upon studies conducted with guinea pigs, bone cultures, and rats, will likely have beneficial results on humans in promoting bone growth in those persons having osteoporosis, in conserving nitrogen to a point where hemodialysis and kidney transplants need not be done in patients with chronic or end stage renal disease, in inhibiting protein breakdown in humans suffering burns and trauma, in permitting long-term flights into space by conserving bone integrity and preventing muscular atrophy, and in producing weight loss in obese subjects in the form of fat reduction while conserving lean body mass and promoting tranquility while in an alert state at normal body temperature. A related aspect of the invention is directed to a method of the isolation and purification of the bear derived isolate, whether from a fasting bear or a denning bear, to a form where predictable results in the above phenomena are readily achieved alone or in combination with other known metabolic substances. The further discovery that a fasting or otherwise normal summer bear, as distinguished from a denning bear, will produce the equivalent of a bear derived isolate (BDI) requires that this invention be considered in terms of a fasting bear, despite the fact that the bulk of the investigation has evolved around the isolate from a denning bear.

A better understanding of the field of invention, the invention itself, and the description of preferred embodiments will follow from an understanding of the definitions of various terms which are used, and which appear in the following "Glossary of Terms".

GLOSSARY OF TERMS

Aliquot: A specified portion.
Alkaline Phosphatase Activity: Activity of this enzyme increases in bone as part of osteoblastic stimulation of bone growth.
Anorexia: Loss of appetite.
Aqueous Fraction: That portion containing water.
Bone Remodeling: A function of bone in which osteoblasts form bone and osteoclasts resorb bone. Positive bone remodeling occurs when the osteoblastic activity exceeds the osteoclastic activity; or when the osteoclastic activity is diminished; or where the osteoblastic activity is increased. In any of these events there is a positive addition to bone. Negative bone remodeling occurs when the osteoclastic activity outstrips the osteoblastic activity, or the osteoblastic activity is reduced from its nonnal balance with the osteoclastic activity; and any combination of the foregoing.
Bone Resorption: Occurs when bone is subjected to osteoclastic activity.
Countercurrent Chromatography (CCC): A technique used to separate substances of different molecular characteristics by using solvents of aqueous and organic properties with centrifugation. Some substances are retained on the coil while others pass through.
Deproteination: Subject the sample to any of various procedures for removing all or part of the original protein in the sample.
Differentiation: To develop into specialized organs or cells.
Eluted: Drawn down, through or off (e.g. liquid through a filter).
Eluted Isocratically: Separate substances off of a column using one solvent system without changing concentration of that solvent system.
Fasting: A voluntary or involuntary state represented by states of non-ingesting, hypophagia, or anorexia. In the context of a fasting active summer bear, while food may be withheld, water is available on demand.
Fibroblast: A stellate or spindle-shaped cell with cytoplasmic processes present in connective tissue, capable of forming collagen fibers.
Gas Chromatography(GC): A method of chromatography in which the substance to be separated into its components is diffused along with a carrier gas through a liquid or solid adsorbent for differential adsorption.
High Performance Liquid Chromatography (HPLC): Method of partitioning chromatography that employs high pressures to propel the solvent through a thin column resulting in a high resolution of complex mixture.
Intraneritoneally: Inside the abdominal cavity.
Latin Square Design: An experimental design which gives statistical meaning to data when using small numbers of experimental units (e.g. numbers of animals, samples, etc.). The number of treatments tested is always equal to the number of experimental units. being used and each experimental unit receives all treatments over time.
Lyophilization: The creation of a stable preparation of a biological substance or isolate (blood serum, plasma, etc.), by rapid freezing and dehydration of the frozen product under high vacuum.
Lyophilize: Freeze dry.
Mass Spectrometry (MS): A procedure used to determine the masses of atoms or molecules in which a beam of charged particles is passed through an electric field that separates particles of different masses.
Metabolites: Any of various inorganic or organic compounds produced by metabolic pathways in the body such as urea, creatinine, amino acids, hydroxy acids, fatty acids, glucose, ions, etc.
Monocyte: Cells with a single nucleus derived from marrow monoblasts. They have deeply indented and irregularly shaped nuclei and bundled and scattered single filaments in the cytoplasm. Marrow monocytes are responsible for forming osteoclasts.
Ninhydrin: Agent used to develop color on TLC plates.
Nuclear Magnetic Resonance (NMR): The absorption of electromagnetic radiation of a specific frequency by an atomic nucleus that is placed in a strong magnetic field, used especially in spectroscopic studies of molecular structure.
Osteoblast: A cell from which bone develops.
Osteoclast: A large multinuclear cell that resorbs bony tissue in the process of osteoclasis.
Osteoid: Relating to or resembling bone ossiform; newly formed organic bone matrix prior to calcification.

Osteoporosis: Demineralization of bone; decrease in bone mass or structure.

Ovariectomy: Surgical removal of the ovaries.

Pellet by Centrifugation: Spin sample to force protein residues to bottom of test tube.

Phosphomolybdic Acid Detection: Method used to develop color on TLC plates.

Renal Failure: Inability of kidney to function properly; one aspect is failure to excrete the amount of urea formed by the body daily. This leads to a gradual elevation of urea which may result in uremia, a toxic condition, that requires dialysis or kidney transplantation for treatment.

Resolution Factor ($R_f$): The distance that the midpoint of the compound travels on a given plate divided by the distance the solvent travels on the plate.

Resorb: To dissolve and assimilate.

Silica Gel/Column Chromatography: Sandlike material is placed in a long glass tube which is wet with solvents and is used to separate the materials by retaining some components on the silica while other components pass through depending on the solvents used.

Sham: A subject is subjected to surgical procedure without removal of organs (ovaries) in order to duplicate the physical and mental impact of the surgical procedure on test animals.

Silica Plate: Glass plate or microscope slide coated or painted with sand-like material. Used to separate and detect substances.

Stirring Rod: Metal or glass rod used to stir mixtures (e.g. spoon in coffee).

Supernatant: Liquid fraction of a liquid solid mixture where the solid has settled to the bottom of its container (e.g. in water and sand, water is the supernatant).

Thin Layer ChromatograLhv (TLC): Method used to separate chemical constituents which can then be identified by color or other properties upon development.

Transamination: A process involved in the metabolism of amino acids in which amino groups ($-NH_2$) are transferred from amino acids to certain keto acids yielding new keto and amino acids.

Triturate: Treat certain dry materials by dissolving part of them into solution leaving behind components that do not dissolve in said solution.

Ultrasonication: Using sound waves to remove particles from small places (e.g. used to clean jewelry).

BACKGROUND OF THE INVENTION

It is known that denning, fasting black bears, fasting polar bears, and pregnant female polar bears who den possess blood factors that can recycle harmful body waste products back into usable protein for building tissue, and that denning, fasting black bears can continue to build bone when the bear is immobile for months at a time. Upon isolating the substance which controls this phenomenon in the bear, there is the possibility that the same can be used to prevent toxic buildups that endanger humans with kidney failure that now require the stressful, expensive treatments of dialysis and kidney transplant to sustain life. The isolate (BDI) also includes the possibility that it can prevent protein breakdown which leads to life threatening situations in humans suffering burns and trauma.

It is believed that such knowledge can lead to strategies to combat bone loss, which afflicts millions of middle aged and elderly people, especially post-menopausal women and astronauts in weightlessness of space. Loss of bone mass in space is one of the major problems that prevents long term space flights by humans.

Bears preparing to enter the denning phase go through a period of hyperphasia during which they eat enough food to store enough fat to last through the denning period. During denning, bears do not eat, do not drink, and do not urinate or defecate. Exiting the den after a four to five month period, the bears resume normal eating patterns. Knowledge and/or the isolate (BDI) may be useful in developing strategies and/or products for the treatment of eating disorders such as anorexia nervosa and bulimia.

Black bears in particular, during their three to five month denning, show a reduction in body temperature of at least 2° C., remain alert and expend energy normally; yet they do not eat, drink, urinate, or defecate and exhibit no problems with waste building to toxic levels. Other mammals, including humans, can recycle some waste, but under similar conditions must quickly rid themselves of the rest of their waste or die.

It has been determined that bears in a non-denning state during summer months are induced to produce the isolate (BDI) after 20 days of fasting, even though they are allowed to drink water. Under these circumstances, bears urinated and did not exhibit the tranquility associated with a denning bear.

Other mammals (including deep hibernators such as ground squirrels who continually awaken throughout hibernation and generate waste they must get rid of) break down protein mainly from muscle to supply energy and other essential nutrients for life. This process not only depletes body muscle, it also releases the toxic form of nitrogen as ammonia. Mammals, including humans, convert the ammonia to urea, which is much less toxic but must be eliminated in urine. During denning, black bears also produce urea, but close this loop and recycle the urea nitrogen back into protein. They produce no waste and maintain muscle mass while eliminating the need to urinate or defecate. The process is so efficient that normal urea concentration in blood decreases and body protein increases. The bear is the only animal known that fasts completely (no food or water) yet ends a 100 day or longer fast with a little more protein (lean tissue) than when it started. During the denning period, the bear steadily consumes body fat that had been stored during the pre-denning period.

This unique response extends to maintenance of bone mass. The bear shows no bone loss even when supine over more than 100 days. In contrast, deep hibernators lose bone and exhibit osteoporosis when hibernating. The bear does not develop osteoporosis and is able to maintain skeletal integrity despite the harsh conditions. Under similar stimuli, humans would suffer severe bone loss.

Taken in the context of the foregoing, it is a desirable forward goal in the treatment of human ailments to be able to isolate the bear derived isolate (BDI) which permits the foregoing phenomena in bears, and to translate it into meaningful metabolic and curative processes in the human.

These goals appear possible. For instance, a bile salt produced by the bear has been shown to improve liver function in humans with the fatal disease of primary biliary cirrhosis. In humans, this bile salt also reverses serious rejection reactions against bone marrow transplants. Further, this bile salt, ursodeoxycholic acid, is the most effective dissolver of human gall stones. Thus, a isolate produced by bears has direct positive application to human disorders.

Important to the present invention is the skill of the technician practicing the invention in identifying when the true state of denning exists in the bear and when the denning bear accomplishes the unique management of wastes such that none accumulate.

Experiments and observations directed to studies in denning bears have been under way for more than 23 years. During that time, it has been established that the recycling of body wastes causes the blood ratio of urea to creatinine (U/C) both expressed in mg/dl to decrease from 20 or more (sometimes ranging as high as 70 after eating a high protein diet) to 10 or less—something impossible for any other mammal that is not drinking fluid. A U/C ratio of 10 or less due to a significant decrease in urea and a significant increase in creatinine indicates that recycling of urea is in progress. The low U/C ratio found throughout denning sometimes occurs in wild bears in the fall just before denning. At this point, wild bears have stored enough fat for denning. They stop eating and drinking; complete waste recycling has begun before they enter the den.

The bear continues to degrade amino acids and form urea. In turn, the urea molecule is quickly degraded by transferring nitrogen from it to substances such as pyruvic acid or alpha-ketoglutaric acid to reform amino acids. This latter process is called transamination. The substances necessary for transamination (pyruvic acid and alpha-ketoglutaric acid) are generated from glycerol which has been released from fat. The newly formed amino acids are then reincorporated into protein.

The overall process of urea recycling consists of two processes: 1) formation of urea from amino acids, and 2) reformation of amino acids from urea which are then reincorporated into protein. Since (2) is faster than (1), there is net formation of new protein. Based on our knowledge, no other fasting animal can accomplish this feat.

Some amino acids formed in the bear are: alanine, serine, ornithine, arginine, glycine, leucine, threonine, phenylalanine, and tyrosine. These amino acids are found in such proteins as albumin and fibrinogen.

Humans can recycle only about 25% of the urea they form. The bear, on the other hand, recycles urea back into protein a little faster than it makes it. Thus, its blood urea concentration diminishes even though it does not drink water or urinate. The amino acids that serve as vehicles for urea recycling are ordinarily found in all mammals, but not in the concentrations shown by bears when fasting. Therefore, it is assumed that they may become vehicles to be used with the bear derived isolate when duplicating the bear's unique recycling.

During denning, the kidney of the bear continually forms urine. Upon reaching the urinary bladder, the urine (which contains BDI) is completely absorbed by the wall of the bladder. Thus, in a highly concentrated form, BDI moves across the bladder wall into blood, circulates, and stimulates all tissues of the bear. When compared to the blood of fasting humans, blood of the denning bear differs in concentrations of some amino acids, bear ketones are much lower, and there is a difference in some other essential substances. While concentrations of many of these substances decrease during human fasting; they do not decrease in the bear. Therefore, exact profiles of these known metabolites may have to be added to BDI in order to duplicate the bear's unique recycling in humans.

Recycling urea, the waste product of protein breakdown, back into protein leads to maintenance of lean body mass.

To prevent bone loss, bone remodeling occurs normally while in the supine state. In the human, a supine state inhibits normal bone remodeling and leads to severe loss of calcium and bone.

All of these stages of prior art were possible only by developing the state of the art that permits bears to den in captivity and to design the definitive studies to explain the processes.

SUMMARY OF THE INVENTION

The present invention results from the discovery of the method and results from isolation of a material in bears, particularly black bears, called Bear Derived Isolate or BDI, that enables denning so that BDI can be used alone or identified with one substance or combination of substances either novel and unique or previously identified to help human beings and other mammals. All predictable results are based upon in vivo studies with guinea pigs, in vivo studies with rats, in vitro organ studies of calvarial mouse bone, and in vitro studies of prevention of proliferation of cells that resorb bone. and stimulation of proliferation of cells that form bone using cell cultures of monocytes, osteoclasts, osteoblasts and fibroblasts. BDI is present in the serum (blood) of denning bears. BDI is also present in urine of denning bears. However, because the bear is an omnivore, fasting in summer is extremely rare. What has been discovered however, is that when the normally active black bear is fasted in the summer time, but water not withheld, over a period of two to three weeks it will develop in the urine the same BDI referred to with regard to denning black bears. Post-fast data showed that urea recycling was induced. This was evidenced by a low serum urea/creatinine ratio, a slight increase in total proteins, and a marked increase in beta-hydroxybutyric acid. Accordingly where the term BDI is used, it includes fasting bears from which food has been withheld but which are not in the traditional denning season. The same can be extrapolated for active polar bears. Because the U/C ratio of polar bears is near 10 or less when fasting, urea recycling is indicated.

In order to obtain the research material (BDI) blood (serum) and urine are collected from black bears during their denning period. Quantities of 100 ml may be drawn monthly from each bear or on a more frequent schedule as required. The urine and/or serum is then subjected to the isolation method as described herein.

As illustrated in Table 1, isolation of BDI requires precipitation of protein from winter urine or serum using methanol, centrifuging the sample and removing precipitated protein as pellets, and drying the BDI into a visible extract. Further, by the use of thin layer chromatography (TLC), countercurrent chromatography (CCC), preparative thin layer chromatography, or column chromatography, at least two compounds, both in urine and blood, can be isolated in BDI.

Thus, the method of isolating these compounds permits predictable separation of BDI into Fractions. These Fractions are suitable for biologic testing. One component is an as-yet-unidentified compound. It is called the Miers-Nelson Component (MNC) after the researchers. The other component is beta-hydroxybutyrate (BHB).

BDI can be divided into three Fractions which are sufficiently purified to test for their biological activity in guinea pigs, rats, and bone culture assays. These Fractions are:

Fraction=BDI-[BHB+MNC](Early fractions),

Fraction=BHB (Middle fractions), and

Fraction III=MNC (Late fractions).

OBJECTIVES OF THE INVENTION

It is a primary object of the present invention to isolate and evaluate BDI which is present in a denning bear or fasting bear.

A further object of the present invention is to permit the isolation of BDI in such quantities that BDI used alone, or in combination with other metabolites and carriers, may be administered orally or by injection to other animals or humans for various treatments.

Being on the cutting edge of a pioneer area of analysis, yet another object of the present invention is to produce BDI (which permits derrning) in order to facilitate further research concerning various beneficial results that can be achieved regarding the kidney, liver, bone growth and remodeling, brain, and nitrogen cycles in the body.

Yet another object of the present invention, and an important one, is to produce BDI in a form which, upon further analysis, will permit synthesis of BDI in larger volumes and at significantly reduced expenditures.

Further objects and advantages of the present invention will become apparent as the following description proceeds, taken in conjunction with the accompanying data.

Following is a Table illustrating the process for the isolation of BDI and two compounds found in it.

TABLE 1

Chemical Process for Isolation of BDI
and Two Compounds Found In It
Research Procedure for Isolating BDI and Its Fractions

| STEP | SAMPLE | PROCESS | YIELDS |
|---|---|---|---|
| One | Urine (50 ml) | 1. MeOH Deproteinization 2. n-BuOH Trituration | Dry Sample (BDI) |
| Two | Dry BDI (3.5 g) | CCC (n-BuOH:AcOH:$H_2O$) 20:1:20 | Dry Sample |
| Three | Dry sample (2 mg) | CCC (n-BuOH:AcOH:$H_2O$) 20:1:20 | Fractions: A. Fraction I BDI – [BHB + MNC] Early CCC Fractions B. Fraction II BHB Middle CCC Fractions C. Fraction III MNC Late CCC Fractions |

DESCRIPTION OF PREFERRED EMBODIMENT

The Denning Process of Bears

The denning process of bears has been defined in the statement of Background of the Invention above. In order to obtain the bear derived isolate successfully, denning bears must be available quickly and throughout the denning period as is the case at The Carle Foundation Bear Research Station, Champaign County, Illinois. At this facility, after food intake decreases in October or November, food is removed, inducing the bear to enter the denning state. At all times where reference is made to the bears which were used to produce BDI, such bears were the well known North American Black Bears (*Ursus americanus*).

Thereafter, blood and urine samples are taken from the bears. This continues until March when the bear leaves its den and has access to food and water. At first (for approximately two to three weeks), the bears slowly begin to eat after they emerge from their dens in the spring. Food intake reaches normal levels, and weight gain continues until early June in preparation for mating. By mid June the bears have normalized their body stores of fat that were diminished during denning and will continue to eat throughout the summer to maintain body weight. Slight increases in body weight throughout the summer can be attributed to continued growth. In late August, in preparation for the subsequent denning season, the bear increases its food intake from 5,000 to 8,000 Calories/day to 20,000 Calories/day. The bear eats almost to a calorie the quantity of food required to store enough fat to support energy requirements of denning, fetal support, and lactation. For a 400 pound bear, energy expenditure during denning is about 4,000 Calories/day.

Bears that have been fasted for a period of not less than 21 days during the summer or non-denning period, whose urine, when subjected to isolation methods, yielded a material (BDI) which produced bone remodeling effects and urea creatinine ratios comparable to that of the material (BDI) taken from a denning bear. The experiment related to 14 bears which were given free access to drinking water, but food was withheld for 21 days. The group was fasted during the month of July, a recognized non-denning period for bears. This was in an attempt to determine whether fasting is the controlling factor in the production of BDI.

Defecation stopped after approximately 2–3 days in the fasting bears, but occasionally bile stain material passed per rectum in some of the bears. With free access to water, the bears drank enough to stimulate urination. (Excess water was required because the only mechanism bears have to regulate body temperature is through evaporation via the respiratory tract. In summer, ambient temperature is much higher than experienced by denning bears, thus there is a need for increased evaporative water loss. This, in turn, stimulated drinking, which exceeded the bears' requirements for body temperature control and thus stimulated urination.) Even though the fasted bears drank water, thirteen of fourteen bears showed an increase in serum creatinine. Eleven of fourteen bears showed a reduction in serum urea, which resulted in a significant reduction in the U/C ratio. Five animals demonstrated values previously known to be associated only with denning bears (Table 2).

TABLE 2

SUMMER BEAR FASTING EXPERIMENT: Jul. 13, 1994 to Aug. 2, 1994

| DATE BEAR | Jul. 13, 1994 PRE-FAST WEIGHT (lbs.) | Aug. 2, 1994 POST-FAST WEIGHT (lbs.) | Jul. 13, 1994 to Aug. 2, 1994 WEIGHT LOSS (lbs.) | Jul. 13, 1994 PRE-FAST UREA (mg/dl) | Aug. 2, 1994 POST-FAST UREA (mg/dl) | Jul. 13, 1994 PRE-FAST CREATININE (mg/dl) | Aug. 2, 1994 POST-FAST CREATININE (mg/dl) | Jul. 13, 1994 PRE-FAST U/C RATIO | Aug. 2, 1994 POST-FAST U/C RATIO |
|---|---|---|---|---|---|---|---|---|---|
| 1-524 | 256 | 214 | −42 | 22.39 | 21.89 | 1.4 | 2.1 | 15.99 | 10.42 |
| 2-523 | 186 | 150 | −36 | 29.61 | 36.20 | 1.4 | 2.2 | 21.15 | 16.68 |
| 3-519 | 358 | 298 | −60 | 31.70 | 27.47 | 1.7 | 2.6 | 18.65 | 10.56 |
| 4-521 | 226 | 186 | −40 | 32.60 | 41.85 | 1.7 | 2.1 | 19.18 | 19.93 |
| 5-522 | 350 | 302 | −48 | 30.90 | 18.24 | 1.8 | 2.1 | 17.17 | 8.69 |
| 6-520 | 298 | 248 | −50 | 32.20 | 30.90 | 2.1 | 2.4 | 15.33 | 12.88 |

TABLE 2-continued

SUMMER BEAR FASTING EXPERIMENT: Jul. 13, 1994 to Aug. 2, 1994

| DATE BEAR | Jul. 13, 1994 PRE-FAST WEIGHT (lbs.) | Aug. 2, 1994 POST-FAST WEIGHT (lbs.) | Jul. 13, 1994 to Aug. 2, 1994 WEIGHT LOSS (lbs.) | Jul. 13, 1994 PRE-FAST UREA (mg/dl) | Aug. 2, 1994 POST-FAST UREA (mg/dl) | Jul. 13, 1994 PRE-FAST CREATININE (mg/dl) | Aug. 2, 1994 POST-FAST CREATININE (mg/dl) | Jul. 13, 1994 PRE-FAST U/C RATIO | Aug. 2, 1994 POST-FAST U/C RATIO |
|---|---|---|---|---|---|---|---|---|---|
| ♀ 7-513 | 210 | 178 | −32 | 30.70 | 26.61 | 1.5 | 2.1 | 20.47 | 12.67 |
| ♀ 8-514 | 216 | 190 | −26 | 45.50 | 27.47 | 1.7 | 2.6 | 26.76 | 10.56 |
| 9-515 | 306 | 260 | −46 | 37.98 | 30.26 | 2.2 | 2.3 | 17.26 | 13.16 |
| ♀ 10-516 | 162 | 140 | −22 | 33.00 | 31.55 | 1.6 | 2.2 | 20.63 | 14.34 |
| 11-518 | 304 | 262 | −42 | 19.74 | 36.48 | 1.6 | 2.6 | 12.34 | 14.30 |
| 12-517 | 306 | 260 | −46 | 44.40 | 24.46 | 2.3 | 2.0 | 19.30 | 12.23 |
| U.P | 412 | 356 | −56 | 49.35 | 24.46 | 2.4 | 2.7 | 20.56 | 9.06 |
| Caruso | 388 | 328 | −60 | 42.30 | 31.76 | 1.9 | 2.4 | 22.26 | 13.23 |
| MEANS | 284 ± 77 | 241 ± 67* | −35 ± 15 | 34.46 ± 8.5 | 29.29 ± 6.3 | 1.8 ± 0.3 | 2.3 ± 0.2* | 19.08 ± 3.47 | 12.75 ± 3.0* |

*Indicates a significant difference between the Pre-fasting and Post-fasting values using a paired t test, $p < 0.01$
SUMMARY
Active bears eating normally were fasted 21 days 'After fasting'
1. 11 out of 14 bears showed a decrease in the concentration of serum urea.
2. 13 out of 14 bears showed an increase in serum creatinine.
3. 12 out of 14 bears showed a decrease in the U/C ratio with 5 bears showing values $\leq 10$.

Data collected from fasted summer bears (after they had been eating normally during the non-denning period) were compared with data collected from fasted winter bears. Although bears usually den (and don't eat) during the winter, these bears had been eating prior to entering the Carle Bear Research Facility. The data collected from the fasted summer bears were similar to data collected from the same bears after a three week winter (Table 3).

It was concluded that after both the summer fast and the winter fast, the bears were in the urea recycling mode previously only characterized during denning.

The prefasted BDI from summer urine tested in bone cultures was from catheterized specimens while the post BID from urine was collected without anesthesia from the

TABLE 3

WINTER BEAR FASTING EXPERIMENT: Feb. 24, 1994 to Mar. 7, 1994

| DATE BEAR | Feb. 14, 1994 PRE-FAST WEIGHT (lbs.) | Mar. 7, 1994 POST-FAST WEIGHT (lbs.) | Feb. 14, 1994 to Mar. 7, 1994 WEIGHT LOSS (lbs.) | Feb. 14, 1994 PRE-FAST UREA (mg/dl) | Mar. 7, 1994 POST-FAST UREA (mg/dl) | Feb. 14, 1994 PRE-FAST CREATININE (mg/dl) | Mar. 7, 1994 POST-FAST CREATININE (mg/dl) | Feb. 14, 1994 PRE-FAST U/C RATIO | Mar. 7, 1994 POST-FAST U/C RATIO |
|---|---|---|---|---|---|---|---|---|---|
| 1-524 | 280 | 230 | −50 | 15.02 | 10.73 | 1.5 | 2.0 | 10.01 | 5.37 |
| 2-523 | 192 | 156 | −36 | 17.17 | 19.31 | 1.6 | 2.2 | 10.73 | 8.78 |
| 3-519 | 384 | 332 | −52 | 30.04 | 15.02 | 2.1 | 2.7 | 14.31 | 5.56 |
| 4-521 | 288 | 238 | −50 | 32.18 | 12.88 | 1.7 | 2.1 | 18.90 | 6.13 |
| 5-522 | 380 | 324 | −56 | 19.31 | 15.02 | 1.7 | 2.3 | 11.36 | 6.53 |
| 6-520 | 282 | 244 | −38 | 23.61 | 10.73 | 2.2 | 2.5 | 10.73 | 4.30 |
| ♀ 7-513 | 228 | 206 | −22 | 27.90 | 10.73 | 1.8 | 2.1 | 15.50 | 5.11 |
| ♀ 8-514 | 222 | 198 | −24 | 36.48 | 21.46 | 2.2 | 2.4 | 16.58 | 8.94 |
| 9-515 | 328 | 282 | −46 | 32.19 | 32.19 | 2.2 | 2.3 | 14.63 | 14.0 |
| ♀ 10-516 | 184 | 152 | −32 | 27.90 | 27.90 | 1.6 | 1.8 | 17.44 | 15.50 |
| 11-518 | 318 | 286 | −32 | 32.19 | 21.46 | 2.4 | 2.9 | 13.41 | 7.40 |
| 12-517 | 354 | 316 | −38 | 17.17 | 10.73 | 1.5 | 2.0 | 11.44 | 5.36 |
| *U.P. | 380 | 374 | −06 | 10.73 | 10.73 | 3.3 | 3.4 | 3.25 | 3.16 |
| *Caruso | 436 | 426 | −10 | 6.40 | 6.44 | 3.2 | 3.2 | 2.01 | 2.01 |
| MEANS | 286 ± 69 | 247 ± 62 | −43 ± 15 | 25.88 ± 7.19 | 17.30 ± 7.21** | 1.9 ± 0.3 | 2.3 ± 0.3** | 13.72 ± 2.92 | 7.73 ± 3.57** |

*Bear was already denning.
**Indicates a significant difference between the Pre-fasting and Post-fasting values using a paired t test. $p < 0.01$.
SUMMARY
Of the bears who were not previously denning (ie had access to food during the winter). after fasting
1. 9 out of 12 bears showed a decrease in the concentration of serum urea.
2. 12 out of 12 bears showed an increase in serum creatinine.
3. 12 out of 12 bears showed a decrease in the U/C ratio with 10 bears showing values $\leq 10$.

specially adapted metabolic cages. As described later, BDI from the latter sample significantly increased osteoblast activity.

Chemistry of the Invention

Introduction

The presentation to follow is divided into two parts. The first deals with the chemical process of isolation and characterization of BDI and two compounds characteristic of the winter denning bears (BHB and MNC) found in BDI. The second part describes the biologic activity of BDI and three of its component Fractions. The chemical isolation of BDI using chromatography makes it possible to divide purified BDI. Countercurrent chromatography yields 50 fractions in successive order: 1–50. The first group of CCC fractions (1–17) does not contain either BHB or MNC. The second group of CCC fractions (18–22) contains BHB. The third group of CCC fractions (23–50) contains MNC, found mainly in fractions 25–29. The CCC machine is then washed out to collect anything left in it. The third division also includes the wash; nothing is discarded. CCC fractions are grouped for further studies and labeled Fraction I, Fraction II, and Fraction III.

The specific fractions related to CCC samples may vary slightly. For instance, BHB may elute in fractions 19–23, and MNC in fractions 24–29. However, all CCC samples at division points are tested by thin layer chromatography so that no BHB appears in either Fraction I or Fraction III and so that no MNC appears in Fraction II.

Therefore, through the use of CCC, two characteristic components can be isolated. They also serve as logical points for division of BDI into three Fractions in order to test biologic activity: Fraction I (BDI–[BHB+MNC]), Fraction II (contains BHB), and Fraction III (contains MNC). When separated by CCC, these Fractions are known to contain amino acids, ammonia, urea, creatinine, creatine, and other animal products.

Identification of Bear Derived Isolate (BDI) Derived from Urine

A 50 ml aliquot of bear urine is deproteinated by diluting with methanol (1:1 v/v) and allowing proteins to precipitate out overnight at $-20°$ C. The proteins are then pelleted by centrifugation (20 minutes @ 2500 r.p.m., $10°$ C.) and the supernatant is extracted. To completely dry the supernatant extract, nitrogen gas is used to remove methanol. Samples are then frozen ($-80°$ C.) and lyophilized. Once dry, samples are weighed using Mettler Analytical Balance AE163. Fifty milliliters of winter bear urine yields approximately 3.5 g of dry residue known as BDI. For observation of the effects of BDI, the dry deproteinated sample (BDI) is reconstituted with 2 or more ml of saline. This solution can then be used for guinea pig and bone culture studies.

Isolation and Characterization of the Miers-Nelson Component (MNC)

Step 1: Verification of MNC Presence In BDI

BDI containing MNC is prepared as before and dried to a residue using nitrogen gas or lyophilization. The BDI is then:

Dissolved in 100–500µl of methanol depending on sample weight.

To test for presence of MNC in number (1) above, approximately 4–6µl is applied to normal phase TLC plates (EM Science, P.O. Box 70, 480 Democrat Road, Gibbstown, N.J. 08027–1296 Silica Gel 60 $F_{254}$, 0.25 mm) in successive µL applications.

The silica plate is then developed in a 4:1:1 1-butanol:acetic acid:water solvent system contained in a TLC chamber. Once developed, the plate is removed, dried by heat gun, and finally detected by ninhydrin spray (0.3% w/v in 1-butanol).

Location of MNC is detected with vigorous heating by heat gun and/or hot plate until edges of the TLC plate are charred. At this point in isolation, MNC is visualized as a pink spot at $R_f=0.74-0.80$.

Step II: Purification of MNC

Approximately 1.75 g of BDI containing MNC is then prepared for the next purification step involving countercurrent chromatography. This procedure utilizes a bi-phasic solvent system of 1-butanol:acetic acid:water (20:1:20) and a Countercurrent Chromatography System with #10 semi-preparative coil (P.C. Inc.).

Two liters of the bi-phasic solvent described above is prepared at least one day prior to using CCC.

This butanol-acetic acid-water solvent system is mixed by shaking and allowed to settle 2 to 4 hours before separation of the organic and aqueous bilayers.

Two liters of solvent yields approximately 1200 ml of the organic stationary phase (primarily composed of butanol) and approximately 800 ml of the aqueous mobile phase (primarily composed of water).

The dried sample of BDI that has been prepared prior to the aqueous/organic solvent system still contains MNC. This sample is reconstituted in 5 ml of the solvent system (2 ml stationary phase; 3 ml mobile phase) and loaded on to a 10 ml injection loop interfaced to the CCC.

The CCC coil is first loaded with 385 ml of stationary (organic) phase.

Using the mobile (aqueous) phase, the triturate is injected onto the coil for separation.

The coil is rotated at approximately 800 r.p.m., flow rate=4 ml/min (LDC Analytical Mini Pump). Five minute samples are collected (Gilson Microfraction Collector #203).

Fifty (20 ml) samples are collected and the coil is washed with methanol:water (1:1 by volume).

All samples are then frozen ($-80°$ C.) and lyophilized (freeze dried).

Once dry, the 50 samples are analyzed by TLC/ninhydrin to determine which samples contain MNC.

MNC elutes in samples 25–29 (approximately 520–580 ml post coil).

Next, those usable, isolated MNC samples are combined with each other for further purification. Sample weight at this stage of purification has been reduced from 1.75 g to 1–2 mg. At this point, samples containing concentrated MNC also contain biological salts and significantly reduced concentrations of other impurities as detected by TLC/ninhydrin, UV, iodine vapor, and phosphomolybdic acid.

Then, samples containing MNC, the remainder of the CCC samples, and the wash of the CCC (fractions 22 through 50 plus wash) are recombined and passed through CCC a second time under the exact conditions described above.

Step III: Harvesting AC: Preparative Thin Layer Chromatography

Final purification of Fraction III (MNC) entails the use of preparative thin layer chromatography.

The dried combined samples of MNC from the second countercurrent chromatography run are the sources of samples to be applied across an 8×12 cm silica thin layer plate. MNC is first reconstituted in 100 µl of methanol and then applied in ten 1 microliter (µl) spots across the plate.

Application of MNC in solution (to the TLC plate) is then repeated 10 times.

In order to achieve the best resolution, between each application the µl spots are allowed to air dry. When finished, each spot on the plate will contain 10 microliters (µl) of MNC in solution forming a band across the TLC plate.

The plate is then resolved in 4:1:1 BuOH:AcOH:$H_2O$. Once the solvent rises to 80%–90% of the TLC plate, the plate is removed from the solvent and dried by heat gun.

Without developing the plate, the MNFC band is removed by scraping the silica from the plate at the $R_f$ region of 0.74–0.80.

The silica is then wetted in approximately 1–2 ml of 1-butanol with vigorous vortex mixing.

The 1-butanol and silica mixture is then centrifuged for 20 minutes at 2500 r.p.m. This allows the silica to pellet to the bottom of the tube.

The MNC containing butanol supernatant is then removed and dried down under nitrogen gas.

At this step in purification, the 1–2 mg sample has been reduced to 100–200 µg of MNNC and is separated from salts and other impurities as detected by TLC/UV, ninhydrin, and iodine vapor. A lipid contaminant is apparent under phosphomolybdic acid development at the solvent front of normal phase TLC plates at this point. However, MNC remains the only significantly concentrated material present as detected by TLC/ninhydrin, UV, iodine vapor, and phosphomolybdic acid detection.

Properties of MC

The harvested MNC has the following properties:
1. It is soluble in water, methanol, and 1-butanol.
2. It is insoluble in less polar organic solvents such as chloroform, toluene, and hexane.
3. It is stable when stored frozen at –20 C. to –85° C. for at least eight years.
4. It is stable at room temperature (20° C.–22° C.) for at least four days.
5. It is heat resistant to 65° C.
6. It is slightly UV active by detection of TLC and UV spectroscopy at 280 and 320 nm wavelengths.
7. It is ninhydrin positive only with extended heating as previously described.
8. It can be identified as pink in color at $R_f$ 0.77–0.80 when purified on normal phase silica TLC plates, sprayed with ninhydrin and heated.
9. It can be detected using iodine vapor development of normal phase silica TLC plates.
10. To date, no tested substances in blood and urine of mammals show characteristics similar to the ninhydrin reaction at $R_f$ range of 0.77–0.80 on the thin layer chromatography used in isolation.
11. Recommended storage of the harvested MNC is to freeze it in a light resistant container under nitrogen gas.

Isolation and Characterization of Beta-hydroxybutyric Acid (BHB)

Preparative Thin Layer Chromatography

The verification, purification, and harvesting of BHB is similar to MNC, except that CCC samples 18–22 are used to elute BHB. Further, BHB is extracted using the same method of preparative thin layer chromatography except that the silica is scraped from the plate at the $R_f$ region of 0.82 to 0.92.

Flash Column Chromatography

An alternative method of harvesting BHB called Flash Column Chromatography can be used. When this method is used, BHB samples obtained from CCC purification are combined and dried.

The combined samples are reconstituted in 250 µl of 1-butanol. Mixing and ultrasonication are used to induce the sample into a homogeneous solution.

Once the samples are completely solubilized in the 250 µl of butanol, 250 µl of acetone is added to the solution. The resultant 500 µl sample is ready for subsequent purification by silica gel flash column chromatography.

A 15×230 mm silica gel (0.040–0.063 mm particle, 230–400 mesh) column is packed and wetted with five column volumes of acetone: 1-butanol (99:1). This ratio significantly contributes to purity and yield.

The 500 µl samples, in 1-butanol:acetone (1:1), are applied to the column and are desirably eluted isocratically with acetone:1-butanol (99:1) under nitrogen gas pressure (5 psi) at a rate of approximately 2 in/min. Fifty (1 ml) samples are collected in approximately 20–30 minutes.

Since acetone is the primary solvent, all collected samples are dried by nitrogen gas or allowed to air dry, and then visualized by TLC/ninhydrin. BHB elutes off the column in samples 19–21 with good reproductibiiity and resolution given the method employed.

Summary of Preparation of Pre-Fasted and Fasted Urine

The bears were fasted overnight before the day of the experiment. They were allowed unlimited access to water. On the day of the experiment bears were anesthetized with Telazol, i.m. 4–5 mg/kg body weight. Baseline blood and urine (catheterized) were taken as pre-fast controls. Catheterized urine was only collected from three of the bears, numbers 4/521;9/515; and 12/517. The urine was pooled and treated with an equal amount of methanol (165 ml). After sitting overnight at –80° C., the urine was centrifuged at 1650 gravity×15 minutes. The supernatant was removed and the precipitate discarded.

Next, the supernatant was placed under a nitrogen stream until most of the methanol had been removed. The sample was then frozen at –80° C. After freezing, the sample was placed on the lyophilizer. YH 11-9-1 (BDI-U) was then used either for use in the bone culture or further purification by countercurrent chromatography (CCC).

Twenty-one days later, the bears were again anesthetized to collect serum and urine in the same fashion as the pre-fasted controls. Prior to this, beginning Jul. 28, 1994 until Aug. 2, 1994, urine was also collected from beneath the cages. All male urine was pooled and female urine was pooled. Catheterized urine was collected from bears and kept separately and treated with an equal volume of methanol after aliquots were removed for urea and creatinine analysis: 6/520 (4ml, YH 11-13-2),9/515 (119ml,YH 11-13-3) and 11/518 (17ml, YH 11-13-4). Also collected from two ofthe older bears was 125 ml from Caruso (YH 11-13-5), and 6.5ml from UP (YH 11-13-6).

The samples were purified by countercurrent chromatography in the following manner. The dried, deproteinated serum (BDI, 0.5 to 1.0 g), was reconstituted in three to four ml of a lower phase 1-butanol:acetic acid:water (20:1:20) mixture. Ten fractions were collected in one run according to the standardized protocol (as attached). The samples were then lyophilized, reconstituted in methanol for transfer to pre-weighed vials, and then dried down under nitrogen for weight determination. At this point, samples were then evaluated for further bone cultures; 1 c/ms or further purification by HPLC. The cultures which were run with urine produced enhanced bone remodeling both of the osteoblastic enhancement and the osteoclastic diminution.

Formation of the Organic Bone Matrix—Osteoid

Both osteoblasts and fibroblasts are involved with formation of osteoid, the matrix of bone. BDI directly stimulates proliferation of osteoblasts, increasing their numbers by 129%. In a similar fashion, BDI directly stimulates proliferation of fibroblasts by 205%. BDI was tested in fibroblast cultures of NIH-3T3 cells. The concentration of BDI that achieved maximum results was 10 mg/ml, the same concentration that achieved maximum results in the osteoblast cultures of MC-3T3 cells. Thus, BDI coordinates the final stage of bone remodeling by furnishing a place to put new bone. BDI induces a similar significant proliferation of fibroblasts (the cells that form matrix or osteoid), the supporting structure of bone, as BDI induced in osteoblasts. Furthermore, the proliferation response of fibroblasts to BDI is similar to proliferation and the bone production response of osteoblasts to BDI.

Thus, BDI orchestrates bone remodeling in a remarkable fashion. In order to form bone while under the combined stresses of not eating or drinking, remaining non-weight bearing, and in the absence of sex steroid production, the bear makes enough bone to avoid osteoporosis. To do this, the bear must shut down bone resorption, stimulate bone formation, and prepare a place to put the newly formed bone. The bear accomplishes this by inhibiting bone resorption while simultaneously stimulating bone formation.

Vitamin D and Bone Integrity In the Denning Bear

During denning, unopposed action by the active form of vitamin D, 1,25-dihydroxyvitamin $D_3$ would produce bone loss, high blood calcium, and death. Ordinarily, 1,25-dihydroxyvitamin $D_3$ stimulates the gut to absorb calcium to replace calcium lost in urine. If insufficient calcium is in food, 1,25-dihydroxyvitamin $D_3$ stimulates bone to release calcium (bone resorption) to keep blood levels of calcium constant.

Since the denning bear is fasting and not urinating, unopposed action of 1,25-dihydroxyvitamin $D_3$ on bone would constantly stimulate bone to release calcium, causing blood calcium to rise to high enough levels to cause cardiac standstill and death. To prevent this occurrence, the bear reduces production of 1,25-dihydroxyvitamin $D_3$ while increasing production of another form of vitamin D—24, 25-dihydroxyvitamin $D_3$. Considered by most a metabolite of vitamin D that has no metabolic action and normally excreted from the body, the 24,25 form actually stimulates bone deposition. The effect of increasing production of 24,25-dihydroxyvitamin $D_3$ while decreasing production of 1,25-dihydroxyvitamin $D_3$ has a favorable effect. The ratio of 24,25 to 1,25 changes from 186 to 300 in captive denning bears (who have ample vitamin D in their summertime food rations) and from 16 to 89 in wild, denning bears.

The large increase in the ratio of 24,25 to 1,25 (61% in captive and 456% in wild bears) serves two purposes:

1. The ability of 1,25-dihydroxyvitamin $D_3$ to release calcium from bone is reduced, and
2. The increase in 24,25-dihydroxyvitamin $D_3$ is enough to recycle calcium that continues to be lost from bone back into bone. The ideal regulation of vitamin D metabolites to prevent high blood calcium only works if the bear can prevent bone loss. We have found that although the bears exists in a stale similar to a postmenopausal woman, the beat makes bone normally, protects its skeleton from osteoporosis, and prevents high blood calcium and death.

Female rats grow normally when receiving daily injections of BDI at a concentration similar to that which enters the blood stream each day from the urinary bladder of a denning bear. No untoward, observable signs or symptoms indicative of adverse reactions to BDI were observed in these rats.

Fasting Summer Bear Conclusions

The fasting summer bear exhibits substantially the same decrease in urea to creatinine ratio as the denning winter bear. Moreover, it exhibits essentially the same bone remodeling enhancement as the denning winter bear. Accordingly, the beneficial aspects of the bear isolate as it relates to renal disorders and osteoporosis appear to be equally as potent with the summer fasting bear as with the winter denning bear.

BIOLOGY OF THE INVENTION

Evaluation of BDI and ITS Fractions

In Vivo Studies: Inducing Denning Bear Behavior in Guinea Pigs and In Vitro Studies: Stimulation of Bone Remoldeling In vivo Studies Introduction The first study was exploratory. It evaluated BDI that had been isolated from winter urine. The second study determined the effects on vital signs of the guinea pig of a lyophilized sample of winter urine and of the precipitate isolated from the urine during deproteination. The third study used a Latin Square Design. It was an in-depth investigation of BDI and three of its isolated Fractions. The fourth study compared fifth study compared BDI derived from winter, denning bears with serum from active, eating bears. As described under "Chemistry of the Invention", serum from winter, denning bears (BDI) and serum from active, eating bears were deproteinized with methanol, the proteins were pelleted by centrifugation, and the supernatants were removed and lyophilized. The dry samples were then reconstituted in 2 ml of saline.

Study One: Exploratory Study Comparing Effects of Summer and Winter Urine on Body Temperature, Heart Rates, and Tranquility in Guinea Pigs Methods Urine from denning and non-denning bears was processed in similar fashion. Guinea pigs received BDI in the same relative concentration as it appears in the denning bear. Thus, the predicted concentration in the blood of the guinea pig was about equal to the predicated concentration of BDI in the blood of the denning bear. Blood volume was estimated as five percent of body weight. 50 ml of urine was deproteinated, lyophilized, and reconstituted in 2 ml of sterile saline as described above. A 2 ml sample was delivered by intraperitoneal injection into each animal.

Results

Five minutes post injection, the animals receiving BDI presented signs of tranquility, reduced heart rate [from approximately 256 to 96 beats per minute (BPM)], and reduced body temperature (from approximately 38° C. to 35° C. or 100.4° F. to 95° F.). The tranquil effects lasted approximately 50 minutes. The tranquil effects were evidenced by the fact that animals could be held on their backs without signs of struggle and that the guinea pigs were alert to their surroundings, but were simultaneously very calm and indifferent to external stimuli such as sudden loud noises. Body temperatures did not return to normal for up to 15 to 20 hours post injection.

Guinea pigs receiving urine from non-denning bears that had been processed in a manner similar to the processing of BDI showed no decreases in body temperature or heart rate. They did not develop a tranquil state.

Conclusion

These data indicate that BDI induces responses of the denning bear in the guinea pig.

Study Two; Comparing Effects of Whole Urine and Precipitate On Heart Rates and Body Temperature In Guinea Pigs Methods Four guinea pigs were injected with varying doses of lyophilized samples of winter bear urine or the precipitate resulting from deproteination of winter bear urine. Rectal body temperature was measured and an electrocardiogram (ECG) was taken every 15 minutes after time of injection, The material to be injected was prepared in the following manner.

Whole bear winter urine was aliquoted out into 20 ml, 40 ml, and two 50 ml samples.

The 20, 40, and one of the 50 ml samples were lyophilized and placed in the freezer until the day of the experiment.

The second 50 ml sample was treated with an equal volume of methanol, vortexed, and allowed to set in the freezer overnight.

The next day, the methanol treated urine was centrifuged and the supernatant removed.

The remaining precipitate was dried under a nitrogen stream and then frozen until the day of the experiment.

On the day of the experiment, each of the four samples were reconstituted into 2 ml of bacteriostatic 0.9% saline for injection. After a control ECG and rectal body temperature (° F.) were taken, each guinea pig was injected intraperitoneally. ECG recordings and rectal temperatures were then taken every 15 minutes for up to 90 minutes.

Results (Table 4 and Table 5)

The guinea pig receiving the protein precipitate (0.0148 g) had an average increase in heart rate of 18 bpm during the 90 minute observation period. The maximum change in heart rate was +28 bpm and occurred 15 minutes after injection. Rectal temperature changes ranged from −1.2° F. to +0.7° F.

The guinea pig that received the lyophilizate from 20 ml of urine (0.5384 g) exhibited an average decrease in heart rate of 49 bpm with the lowest heart rate measured at 15 minutes after injection. Rectal temperature decreased an average of 2.1° F. over the 90 minutes.

In the animal that received the lyophilizate from 40 ml of urine (1.2164 g), heart rate decreased by an average of 60 bpm within 15 minutes after injection. However, heart rate returned to normal more rapidly in this particular animal than in the guinea pig that received only 20 ml of the lyophilized urine. Therefore, the average change in heart rate for this animal was only −4 bpm. In contrast, rectal temperature decreased by 5.5° F. and remained lowered even at 90 minutes.

The guinea pig that received the highest dose of the lyophilizate from 50 ml of urine exhibited a maximum decrease in heart rate (−154 bpm) at 15 minutes. Rectal temperature decreased by 7.3° F. and was still 6° lower than control 90 minutes after injection.

All animals survived.

TABLE 4

GUINEA PIG STUDY: WHOLE URINE AND PRECIPITATE MEAN CHANGES IN HEART RATES (BPM)
(Treated Rates − Control Rates)

| Post Injection Time | Protein Precipitate | 20 ml | 40 ml | 50 ml |
|---|---|---|---|---|
| 15 minutes | +28 | −83 | −60 | −154 |
| 30 minutes | +18 | −34 | +19 | −129 |
| 50 minutes | +17 | −50 | +15 | −103 |
| 75 minutes | +20 | −43 | +6 | −135 |

TABLE 4-continued

GUINEA PIG STUDY: WHOLE URINE AND PRECIPITATE MEAN CHANGES IN HEART RATES (BPM)
(Treated Rates − Control Rates)

| Post Injection Time | Protein Precipitate | 20 ml | 40 ml | 50 ml |
|---|---|---|---|---|
| 90 minutes | +9 | −37 | 0 | −120 |
| Mean of Means | +18.4 | −49.4 | −4.0 | −128.2 |

TABLE 5

GUINEA PIG STUDY: WHOLE URINE AND PRECIPITATE CHANGES IN BODY TEMPERATURE (° F.)
(Treatment Temperature − Control Temperature)

| Post Injection Time | Protein Precipitate | 20 ml | 40 ml | 50 ml |
|---|---|---|---|---|
| 15 minutes | — | −0.5 | −0.3 | −4.3 |
| 30 minutes | 0.0 | −2.6 | −2.8 | −5.0 |
| 45 minutes | +0.7 | −4.4 | −5.5 | −7.3 |
| 60 minutes | −1.2 | −3.2 | −5.3 | −6.8 |
| 90 minutes | −0.7 | −0.0 | −5.1 | −6.8 |
| Mean | −0.3 | −2.14 | −3.8 | −6.0 |

Summary

Fifty ml of winter bear urine that had been lyophilized and reconstituted in 2 ml of normal saline caused a 45% decrease in heart rate within 15 minutes of injection.

Fifty ml of winter bear urine that had been lyophilized and reconstituted in 2 ml of normal saline caused a decrease in rectal temperature that was maximal at 45 minutes post injection.

Both effects were sustained throughout the 90 minute observation period.

In the guinea pigs that received the lower doses of the lyophilizate from bear urine, heart rate and rectal temperature still decreased with maximal effects measured at 15 minutes for heart rate and 45 minutes for temperature.

The magnitude of the effects produced by 20 ml and 40 ml of urine were smaller when compared to 50 ml of urine.

The animal that received the precipitate intraperitoneally exhibited an increase in heart rate rather than a decrease with little or no change in rectal body temperature.

Conclusions

The lyophilized winter bear urine injected intraperitoneally into conscious guinea pigs produced a decrease in heart rate and rectal body temperature similar to changes previously noted with BDI. The precipitate from the same volume of urine did not produce the same effects; it did not decrease heart rate and had little or no effect on rectal body temperature.

Study Three: Latin Square Designed Studies—The Effect of BDI in A Non-Hibernating Animal. The Guinea Pig Introduction This study was designed to test the effects of BDI and its Fractions in guinea pigs. To ensure unbiased observations, the study was blinded so that the researchers did not know which animal was injected with BDI, with Fraction I, with Fraction II, with Fraction III, or with saline. The Latin Square Design permitted use of animals as their own controls. Thus, in each animal, changes in heart rate and temperature after experimental injections were compared to the guinea pig's own recorded normal heart rate and temperature prior to each injection. In addition, all animals received a control injection of sterile saline during the five week experimental period in an effort to measure the physiologic response in each animal to the pain of the injection itself. Food and water intake, urine output, and urea and creatinine excretion in urine were measured daily for four days after each injection. Therefore, each animal is used as its own control, and each sample injection can be compared to a saline control injection in all animals.

Methods

Heart rates were intermittently monitored by electrocardiograms. Rectal temperatures were intermittently monitored via inserted thermistors calibrated to National Bureau of Standard requirements. Recordings were made every 15 to 30 minutes throughout the two to three hour study. A video camera was used to record behavioral activity in each animal throughout the study. Research observers were asked to comment on each animals' tranquility by observing animal handling and animal reaction when exposed to a loud snapping noise. Thereafter, the animals were housed in a metabolic cage throughout the five-week experiment in order to measure food and water intake and urine output. Urine urea and creatinine concentrations were measured. Effects of the following fractions were compared with BDI, with the saline control, and with each other: Fraction I, representing BDI−[BHB+MNC]; Fraction II, representing BHB; and Fraction III, containing MNC.

Design

Fractions were obtained by combining appropriate samples from the second CCC run. They were lyophilized as those for BDI. Thereafter, they were reconstituted in a saline solution.

After collecting Fraction I, Fraction II, and Fraction III, the study was blinded so that the researchers did not know which animal was injected with Fraction I, with Fraction II, with Fraction III, with saline, or with BDI. Animals were used as their own controls in a Latin Square Design. Heart rates were intermittently monitored by electrocardiograms. Rectal temperatures were intermittently monitored via inserted thermistors. Results were recorded every 15 to 30 minutes throughout the two to three hour study. A video camera was used to record behavioral activity in each animal throughout the study.

To measure effects on body temperature (° C.), heart rates (BPM), and tranquility from each injection on the five guinea pigs, the data were grouped into the following time categories: Zero minutes (pre-injection control), 15–25 minutes, 30–40 minutes, 41–59 minutes, 60–74 minutes, and 75–95 minutes (post injection). Each animal was used as its own control. Treatment means were reported as the difference of each injection effect from the zero minutes (control) result. Therefore, positive or negative treatment mean values indicate an increase or decrease in the effect measured. A similar approach was used for daily determinations of food and water intake and urine excretion of urea and creatinine.

Results

Body Temperature (Table 6)

Beginning at 30 minutes and extending through to the end of the study, BDI produced a significant reduction in body temperature. The overall mean of temperature reduction was seven fold greater than that experienced by the animal when it received saline as a control measure.

Effects of Fraction I, Fraction II, and Fraction III were not different from control observations throughout the study.

TABLE 6

GUINEA PIG STUDY: 5 × 5 LATIN SQUARE
MEAN CHANGES IN BODY TEMPERATURE (° C.)
(Treatment Temperature − Control Temperature)

| Post Injection Time | I | II | III | BDI | C | p < 0.05 |
|---|---|---|---|---|---|---|
| 15 to 25 minutes | 0.33 | 0.41 | 0.35 | 0.34 | 0.01 | N.S. |
| 30 to 40 minutes | 0.10 | 0.34 | 0.19 | −0.31 | −0.31 | N.S. |
| 41 to 59 minutes | 0.03 | 0.22 | 0.17 | −0.84 | −0.24 | N.S. |
| 60 to 74 minutes | −0.15 | 0.21 | 0.10 | −1.14 | 0.01 | * |
| 75 to 95 minutes | −0.42 | 0.12 | 0.38 | −1.54 | −0.15 | * |
| Mean of Means | −0.02 | 0.26 | 0.24 | −0.70 | −0.10 | — |

I = BDI − (BHB + MNC)
II = BHB
III = MNC through Wash
C = Saline Control
*Treatments are significantly different at $p < 0.05$ BDI produced a significant reduction in heart rate. Animals receiving Fraction I showed a significant heart rate reduction of approximately 50% of that shown by BDI. Animals receiving Fraction III showed a moderate but not a statistically significant reduction in heart rate (approximately 20% of that shown by BDI). Compared to BDI, those receiving Fraction II showed only a 10% reduction in heart rate. Saline injection failed to reduce heart rate (Table 7).

TABLE 7

GUINEA PIG STUDY: 5 × 5 LATIN SQUARE
MEAN CHANGES IN HEART RATES (Beats per Minute)
(Treatment Rates − Control Rates)

| Post Injection Time | I | II | III | BDI | C | p < 0.05 |
|---|---|---|---|---|---|---|
| 15 to 25 minutes | −34.4 | −7.2 | −15.2 | −54.0 | 9.2 | * |
| 30 to 40 minutes | −29.4 | −4.4 | −9.2 | −53.0 | 6.8 | ** |
| 41 to 59 minutes | −25.0 | −7.6 | −11.4 | −62.8 | 6.8 | * |
| 60 to 74 minutes | −19.8 | 2.2 | −13.4 | −53.8 | 4.4 | N.S. |
| 75 to 95 minutes | −23.4 | −7.6 | −10.2 | −51.6 | 0.2 | N.S. |
| Mean of Means | −26.4 | −4.9 | −11.9 | −55.0 | 5.5 | — |

I = BDI − (BHB + MNC)
II = BHB
III = MNC through Wash
C = Saline Control
*Treatments are significantly different at $p < 0.05$
**Treatments are significantly different at $p < 0.01$ Food and Water Intake Guinea pigs that received BDI showed a decreased intake of food that was significant by the third and fourth day post injection.

Water intake by guinea pigs that received BDI was not changed.

Urine urea to creatinine ratios were profoundly reduced in guinea pigs receiving BDI.

Tranquility (Table 8)

Only animals receiving BDI were rated more tranquil than those receiving saline.

TABLE 8

GUINEA PIG STUDY: 5 × 5 LATIN SQUARE
TRANQUILITY

| Substance | Fraction | Number of Animals | Tranquility* |
|---|---|---|---|
| BDI | — | 5 | 3.6 |
| BDI − (BHB + MNC) | I | 5 | 2.0 |
| BHB | II | 5 | 2.8 |

TABLE 8-continued

GUINEA PIG STUDY: 5 × 5 LATIN SQUARE TRANQUILITY

| Substance | Fraction | Number of Animals | Tranquility* |
|---|---|---|---|
| MNC | III | 5 | 2.8 |
| Saline (Control) | C | 5 | 2.6 |

*Animals rated 1 to 4 (anxious to tranquil) when exposed to a brief snapping sound and turned over on their backs Deaths Two animals died within 24 hours. One received Fraction I; the other received BDI.

Summary

BDI demonstrated significant and profound reductions in body temperature when compared to its Fractions—I, II, or III.

The reductions in body temperature stimulated by BDI increased over time with temperatures remaining low for up to 24 hours.

Individual components of BDI (Fraction I, Fraction II, and Fraction III) had no effect on body temperature.

BDI demonstrated significant and profound reductions in heart rate when compared to its Fractions—I, II, or III.

Heart rates were reduced significantly within 30 to 60 minutes after the injection of BDI and tended to return to normal within two to three hours post injection.

In order of responses, Fraction I, Fraction III, and Fraction II reduced, but to a much lesser degree, heart rates independently.

The decrease in urea to creatinine ratios were profoundly reduced in guinea pigs receiving BDI.

Only BDI induced tranquility over that shown by animals receiving the saline control.

Conclusion

BDI contains components that target specific physiologic changes independently, but BDI exhibits the greatest overall effects when all the components of BDI are present. The performance of BDI exceeds the results of any of the above fractional components.

Study Four: Effects of Combination of Fraction I, Fraction II, and Fraction III Isolated From Urine In A Non-Hibernating Animal, the Guinea Pig Introduction Samples were defined as follows:
1. Combination A: Fraction I plus Fraction III representing BDI–BHB; contains MNC.
2. Combination B: Fraction I plus Fraction II representing BDI–MNC; contains BHB.
3. Combination C: Fraction II plus Fraction III representing BHB+MNC.

The above Combinations were obtained by combining appropriate samples from the second CCC run. They were dried as those for BDI. Thereafter, they were reconstituted in a saline solution.

Methods

BDI obtained from urine taken from early, mid, and late denning bears was used for isolation of Fraction I, Fraction II, and Fraction III. The combinations were injected intraperitoneally.

Body temperature (° C.), heart rates (BPM), and tranquility were measured for each treatment on three guinea pigs.

Data were grouped into time categories: 0 minutes (pre-injection control), 30 minutes, 60 minutes, 75 minutes, and 260 minutes (post injection).

Each animal was used as its own control. Treatment means are reported as the difference of each treatment effect from the 0 minutes (control) result. Therefore, as in the Latin Square Study, positive or negative treatment mean values indicate an increase or decrease in the effect measured. A mean of the Combination means was then calculated from each Combination over all animals and all time categories. All research observers (blinded study) were asked to comment on each animals' tranquility by observing the animal handling and animal reaction when exposed to a loud snapping noise.

In these studies, comparison between guinea pigs, sample potency was expressed as the ratio of averaged treatment means to g dry weight of each sample injected.

Results

Temperatures (Table 9) were reduced in all three guinea pigs receiving Combination A, Combination B, and Combination C with the largest decreases in temperatures occurring in animals receiving Combination A or Combination B.

When temperature responses were related to weight of the injected sample (Table 9-Potency), Combination A, Combination B, and Combination C were potent in reducing body temperatures. Combination C had the greatest potency (Table 9).

TABLE 9

GUINEA PIG STUDY: COMBINED FRACTIONS
CHANGES IN BODY TEMPERATURE (° C.) AND POTENCY
(Treatment Temperature – Control Temperature)

| Post Injection Time | Combination A | Combination B | Combination C |
|---|---|---|---|
| 30 minutes | −0.21 | −0.67 | −0.17 |
| 60 minutes | −1.21 | −1.68 | −0.17 |
| 75 minutes | −1.60 | −2.01 | −0.34 |
| 260 minutes | −4.49 | −3.63 | −1.50 |
| Mean | −1.88 | −2.00 | −0.55 |
| Sample Weight | 3.3833 g | 1.9917 g | 0.1699 g |
| Potency* | −0.56 | −1.00 | −3.24 |

Combination A = Fraction I + Fraction III = BDI − BHB (Contains MNC)
Combination B = Fraction I + Fraction II = BDI − MNC (Contains BHB)
Combination C = Fraction II + Fraction III = MNC + BHB (Through Wash)

Heart rates were reduced in all three guinea pigs. The largest reductions occurred in animals receiving combinations A and B (Table 10).

Combination C was most potent in reducing heart rate (Table 10).

TABLE 10

GUINEA PIG STUDY: COMBINED FRACTIONS
MEAN CHANGES IN HEART RATES
(Beats per Minute) AND POTENCY
(Treatment Rates – Control Rates)

| Post Injection Time | Combination A | Combination B | Combination C |
|---|---|---|---|
| 30 minutes | −88.0 | −54.0 | −14.0 |
| 60 minutes | −70.0 | −67.0 | −50.0 |
| 75 minutes | −79.0 | −60.0 | −68.0 |
| Mean of Means | −70.0 | −60.3 | −44.0 |
| Sample Weight | 3.3833 g | 1.9917 g | 0.1699 g |
| Potency* | −23.4 | −30.3 | −258.8 |

Combination A = Fraction I + Fraction III = BDI − BHB (Contains MNC)
Combination B = Fraction I + Fraction II = BDI − MNC (Contains BHB)
Combination C = Fraction II + Fraction III = MNC + BHB (Through Wash)

Combination A, Combination B, and Combination C produced tranquility in the animals (Table 11).

TABLE 11

GUINEA PIG STUDY: EFFECT OF COMBINED FRACTIONS, TRANQUILITY

| Substance | Combination | Number of Animals | Tranquility* |
|---|---|---|---|
| BDI − BHB (Contains MNC) | Combination A (Fraction I + Fraction III) | 1 | 4.0 |
| BDI − MNC (Contains BHB) | Combination B (Fraction I + Fraction II) | 1 | 4.0 |
| MNC + BHB | Combination C (Fraction II + Fraction III) | 1 | 3.0 |

*Animals rated (anxious to tranquil) when exposed to a brief snapping sound and turned over on their backs
Animals receiving Combination A or Combination B died within 24 to 48 hours post injection.

Summary

Combination A, Combination B, and Combination C greatly reduced body temperature and heart rate.

Reductions in body temperature increased over time with temperatures remaining low for up to 24 to 48 hours.

Heart rates were reduced within 30 to 60 minutes after the injections and remained low throughout the 75 minutes that the animals were monitored.

Combination C gave the largest potency effect in temperature and heart rate reduction. The animal survived. This suggests that the components of Combination C may be the predominantly active ingredients in BDI containing no toxic side effects.

Conclusions

BDI from urine and its combined components demonstrate dramatic decreases in body temperature and heart rate in non-denning guinea pigs.

BDI from urine and its combined components also produce alert tranquility in this non-denning animal model.

Study Five: Comparison of BDI Derived From Denning Serum and Serum From Active Bears In A Non-Hibernating Animal, the Guinea Pig Methods As previously described, equal volumes of BDI and summer active serum were processed by deproteinization, centrifugation, supernatant removed, lyophilization, and residue reconstitution into 2 ml of saline. The reconstituted samples were each intraperitoneally injected into guinea pigs. Body temperatures, heart rates, and tranquility ratings were recorded as described in Study One, Study Two, and Study Three.

Results

The mean decrease in body temperature associated with BDI was −0.19° C. This is approximately two-fold greater than the −0.10° C. shown by serum from active bears and by saline controls in the Latin Square Design.

No significant change in heart rates occurred after injection. BDI was associated with an overall mean decrease of 8 beats/minute; active bear serum showed a mean decrease of 7 beats/minute.

Neither animal showed signs of tranquility.

Conclusions

BDI from serum showed only a mild response in lowering body temperature.

Active bear serum showed no response in lowering body temperature.

Neither BDI from serum nor active bear serum affected the heart rate or induced tranquility.

The lack of response may be attributable to an extremely low concentration of BDI in the. samples.

Overall Conclusions of Guinea Pig Testing

When given intraperitoneally to the guinea pig, BDI induces the responses of the bear: tranquility, decreased heart rate, and decreased body temperature.

No differences in guinea pig results were noted when BDI was isolated from early, mid, or late denning bears.

BDI was most effective when used in full strength.

Isolated Fractions of BDI by themselves were inactive.

Combination of BDI into Combination A (Fraction I plus Fraction II), Combination B (Fraction I plus Fraction III), and Combination C (Fraction II plus Fraction III) also elicited positive results. Combination A and Combination B were associated with side effects which were, most likely, due to Fraction I. Three of seven animals died. They either received Fraction I or Combinations A and B that contained Fraction I.

A definite, safe, and highly active response with no observable side effects was noticed in the animal receiving purified Combination C (Fraction II plus Fraction III).

Treatment of Osteoporosis in Ovariectomized Rats

Our next step was to treat a living animal model similar to the post menopausal woman with BDI.

We used a pharmaceutical industry accepted animal model. Growing rats, less than six months old, were randomized into three groups of six rats each. One group was control (sham operated), one was ovariectomized, and one was ovariectomized and received BDI via subcutaneous injection. Similar volumes of saline were injected into the other two groups. BDI was given in amounts similar to its daily production in bears but proportionally scaled to body weight of the rat.

At the end of eight weeks, the ovariectomized group had become osteoporotic. When compared with this group, the ovariectomized group treated with BDI showed a 3% increase in bone mineral density (BMD) of the femur and a 4% increase in the lumbar vertebrae.

When compared with two month results of treating post menopausal women with estrogen, progesterone, and calcium, BDI results in rats showed a 16-fold greater increase in the BMD in lumbar vertebrae and a 3-fold greater increase in BMD of the femur. Another group of women on similar hormone replacement therapy showed only a 1.7% increase in BMD of the lumbar spine even though they were treated for 1.6 years.

In vitro Studies: Evaluation of BDI and Its Fractions In Stimulating Bone Remodeling Introduction These studies focused on serum and urine obtained from denning bears. The bone mass of denning bears remains constant even though they exist in a non-weight bearing state, a condition that induces loss of bone. Unlike other mammals, the bear maintains bone mass, structure, and strength. In the bear, the cells that produce bone (osteoblasts) are as active as the cells that resorb bone (osteoclasts). Under similar conditions, other mammals (including humans) lose bone by reducing bone formation, by maintaining or increasing bone resorption, or by a combination of these changes.

Test One. Inhibition of the Resorption Activity of Chicken Osteoclasts

Introduction

Unprocessed serum from active eating bears and unprocessed serum from denning bears both showed an inhibition of osteoclast resorption activity. The studies focused on the denning bear because it continues to make bone despite the fact that its non-weight bearing state lasts for months.

Methods
BDI Serum Studies (Table 12)

BDI, BHB, and BDI-BHB (containing MNC) were prepared from serum of bears as described under "Chemistry of the Invention" in this application.

Results

BDI from three bears in concentrations of 1 mg/ml of sample reduced osteoclast resorption activity to values of 24, 46, and 55 percent of control. More dilute samples were not effective (0.1, 0.01, 0.001 mg/ml).

The sample BDI-BHB that contains MNC also proved effective in two bears at concentrations of 1 mg/ml, reducing osteoclast resorption activity to 10 and 75 percent of control.

BHB by itself had no effect on osteoclast resorption.

Test Two: Simultaneous Evaluation of Osteoblast and Osteoclast Activity

Methods and Materials

Experiments utilized an in vitro bone culture system. Calvaria (skull) of 4 to 6 day old neonatal mice were dissected out and cultured in individual capped test tubes in 2 ml of culture media (DMEM+glutamine, heparin, inactivated horse serum, and antibiotics). Each calvaria was gassed and incubated in a rotating roller drum at 37° C. Osteoblast activation (increased bone formation) was evaluated as a function of alkaline phosphatase activity (ALP). Osteoclast activity (bone resorption) was evaluated as a function of beta-glucuronidase activity. For testing purposes, two samples of serum from bears were used: 1)

TABLE 12

BEAR SERUM: INHIBITION OF FORMATION OF CHICKEN OSTEOCLASTS FROM CHICKEN MONOCYTES OBTAINED FROM BONE MARROW

| | | | | Percent Reduction from Control Concentration of Test Sample (mg/ml) | | | |
|---|---|---|---|---|---|---|---|
| Substance | Bear Name | Weight (g) | CCC Samples | 0.001 | 0.01 | 0.1 | 1.0 |
| BDI | Amanzo | 0.017 | not run | 125 | 115 | 108 | 55 |
| | Caruso | 0.012 | not run | 80 | 106 | | 46 |
| | UP | 0.020 | not run | 152 | 93 | 90 | 24 |
| BDI – BHB | Amanzo | 0.026 | Fraction I and III | 119 | 103 | 108 | 75 |
| (Contains MNC) | UP | 0.078 | Fraction I and III | 84 | 90 | 60 | 10 |
| BHB | Amanzo | 0.0006 | Fraction II | | 130 | 130 | 135 |
| | Caruso | 0.0023 | Fraction II | | 95 | 95 | |
| | UP | 0.002 | Fraction II | 80 | 105 | 110 | |

Conclusion

Direct action of BDI isolated from serum with or without BHB produced an environment conducive for bone formation by inhibiting resorption activity of osteoclasts, the cells that dissolve bone.

BDI Urine Studies (Table 13)

Methods

BDI was prepared from urine from three bears as described previously under "Chemistry of the Invention" of this application.

Results

BDI in concentrations of 10 mg/ml of sample inhibited resorption activity of osteoclasts to values of 25, 35, and 38 percent of control. More dilute samples were not effective (Table 13).

TABLE 13

BEAR URINE: INHIBITION OF FORMATION OF CHICKEN OSTEOCLASTS FROM CHICKEN MONOCYTES OBTAINED FROM BONE MARROW

| | | | Percent Reduction from Control Concentration of Test Sample (mg/ml) | | | | |
|---|---|---|---|---|---|---|---|
| Substance | Bear Name | Sample Weight (g) | 0.01 | 0.1 | 1 | 3 | 10 |
| BDI | Amanzo | 0.268 | 147 | 110 | 130 | 95 | 25 |
| | Caruso | 0.255 | 125 | 85 | | | 35 |
| | UP | 0.270 | 123 | 107 | | | 38 |

Conclusions

BDI isolated from urine induces bone formation by inhibiting bone resorption by osteoclasts.

BDI isolated from serum is approximately 10 times more effective than BDI isolated from urine in reducing bone resorption by osteoclasts.

unprocessed bear serum, and 2) processed bear serum (BDI). Horse serum was used as a serum control to ensure that stimulation was not due to serum growth factors.

Results

Unprocessed bear serum from active, eating, weight-bearing bears increased ALP activity from 600 to 1200 nmole ALP/bone/30 minutes.

Unprocessed bear serum from denning, non-eating, non-active, non-weight bearing bears also significantly increased ALP activity from 600 to 1200 nmole ALP/bone/30 minutes.

Horse serum showed no change in ALP activity.

Unprocessed bear serum from denning bears showed a dose response result. The saline control value of 250 ALP/bone/30 minutes significantly.increased to 600, to 800, and to 1000 ALP/bone/30 minutes in response to 50, 100, and 200 $\mu l$ of serum respectively.

BDI increased ALP activity from 310 to 520 ALP/bone/30 minutes, about 55% of the response elicited by unprocessed bear serum that, in the same test, increased ALP to 700 ALP/bone/30 minutes.

The ability of BDI to increase ALP activity proved significantly greater than effects of calcitonin.

Inactivating serum proteins in unprocessed bear serum by heat produced results similar to BDI; ALP activity increased.

BDI failed to activate beta-glucuronidase. Combining these findings with the above indicated that BDI primarily stimulated bone formation by osteoblasts.

Unprocessed serum from active and denning bears showed both mild stimulation and failure to stimulate beta glucuronidase activity. However, when osteoclasts were stimulated, the response was less than one-half of the osteoblast stimulatory response. Therefore, bone formation activity continued to exceed bone resorbing activity.

Conclusions

Unprocessed serum from active and denning bears stimulates osteoblasts.

Unprocessed serum from active and denning bears varied in its ability to stimulate osteoclasts. At times no changes were observed; at other times mild stimulation was observed.

BDI stimulates osteoblasts to about 55% of that shown by unprocessed serum.

BDI does not stimulate osteoclasts.

The overall effect on bone remodeling is creation of an environment conducive to bone formation stimulation of the limb that forms bone (osteoblasts) while not stimulating bone resorption (osteoclasts).

Test Three: The Effect of Summer Fasted BDI on Osteoblast and Osteoclast Activities Introduction As previously described, fasted bears (who had access to water) during the summertime revealed changes in levels of serum urea, creatinine, and a U/C ratio similar to changes noted when bears were denning. Thus, it was concluded that the summer fasting bears were in the mode of urea recycling (See Tables 1 and 2). Test Three was done to determine if bone remodeling was also stimulated when the bears were fasting. The effect of the 21 day summer fast on bone remodeling was determined by evaluating the activity of BDI obtained from these bears in an in vitro bone culture system.

Materials and Methods

As described in the discussion Test Two, calvaria of 4 to 6 day old neonatal mice were used for the in vitro bone culture system. Alkaline phosphatase activity (ALP) was used as a means of evaluating osteoblast activity (increased bone formation).

Because previous tests using beta glucuronidase activity to evaluate osteoclast activity (increased bone resorption) were inconclusive, a more sensitive test was employed. The production of tartrate resistant acid phosphatase (TRAP) was used as a measure of osteoclast activity (Lau et al., 1987; Delamis 1988). For testing purposes, BDI was prepared from urine of bears before and at the end of the 21 day fast. Denning bear plasma served as a positive control. Pre-fasted BDI was compared with fasted BDI. Both were compared with denning bear plasma and all three samples were compared with the phosphate buffered saline control.

Results

Osteoblast Results (Table 14)

Pre-fasted BDI results were similar to results of denning bear plasma. Both showed a moderate, significant increase in osteoblast activity (55% and 50% above control respectively). However, BDI from the final day of fasting significantly stimrulated osteoblasts some 300% above control, about a six-fold increase over results from denning bear plasma or pre-fasted BDI.

TABLE 14

Changes in Medium Alkaline Phosphatase Activity
In Calvaria Incubated with Normal Denning Bear Plasma
and BDI Processed from Urine
Before and At the End of a 21-Day Fast

| Treatment Group | ALP Activity[1] |
|---|---|
| PBS (Phosphate Buffered Saline) | $444.8^a \pm 108.5$ |
| BP (Denning Blood Plasma) | $666.4^{a,b} \pm 127.2$ |

TABLE 14-continued

Changes in Medium Alkaline Phosphatase Activity
In Calvaria Incubated with Normal Denning Bear Plasma
and BDI Processed from Urine
Before and At the End of a 21-Day Fast

| Treatment Group | ALP Activity[1] |
|---|---|
| Fasted (BDI from Urine of Fasted Bears) | $1337.7^c \pm 346.3$ |
| Pre-Fasted (BDI from Urine of Non-Fasting Bears) | $690.9^b \pm 120.9$ |

[1]nmol of p-nitrophenol/30 min/bone
Different letters indicate a significant difference, $p < 0.05$, $n = 6$ Osteoclast Results (Table 15)

When using TRAP as an indicator of osteoclast activity, results clearly demonstrate BDI's ability to inhibit osteoclast function. Both the fasted and pre-fasted results showed similar, significant inhibitory effects on osteoclast function, reaching levels 40% to 46% of normal. These results confirmed results using the chicken osteoclast tissue culture assay (Tables 12 and 13) as an indicator of osteoclast activity. Denning bear plasma showed no effects on osteoclast function.

TABLE 15

Changes in Medium Tartate Resistant Acid Phosphatase Activity
In Calvaria Incubated With Normal Denning Bear Serum
and BDI Processed from Urine
Before and at the End of a 21-Day Fast

| Treatment Group | TRAP Activity[1] |
|---|---|
| PBS (Phosphate Buffered Saline) | $142.5^a \pm 53.5$ |
| BP (Blood Plasma) | $182.8^a \pm 58.2$ |
| Fasted (BDI from Urine of Fasted Bears) | $77.4^b \pm 4.1$ |
| Pre-Fasted (BDI from Urine of Non-Fasting Bears) | $84.0^b \pm 4.9$ |

[1]nmol of p-nitrophenol/60 min/bone
Different letters indicate a significant difference from the phosphate buffered saline control, $p < 0.05$, $n = 6$ Conclusions Summer fasting in black bears induces a significant increase in potency of BDI in stimulating bone formation through activation of osteoblasts. Simultaneously, BDI significantly inhibits osteoclast activity. Thus, fasting in summer potentiates BDI's ability to stimulate bone formation.

Overall Conclusions of Bone Remodeling Studies

Results of the two separate studies independently performed at two institutions in two different states show complementary findings that support the conclusion that BDI stimulates bone formation and inhibits bone resorption since: BDI stimulates osteoblasts to form bone, BDI does not stimulate osteoclasts already present in bone, BDI inhibits resorption of bone by osteoclasts, and the net effect of these changes is to form bone. Summer fasting induces similar results in bone remodeling.

BDI is extremely potent since it stimulates the bone forming process while simultaneously inhibiting the bone resorption process of bone remodeling. Summer fasting in bears duplicates these positive findings found in denning bears.

Occurrence of Fraction II (BLHB) and Fraction III (MNC) In Fasting, Adult Humans Methods and Materials Initially, BHB was identified by TLC/ninhydrin in very low concentrations in serum samples obtained from two humans that fasted for 20 hours. The serum samples were also deproteinated using the same method established for BDI. A follow-up study was done in fifty adult humans who had fasted for twenty hours to determine if components contained in BDI, namely BHB and MNC, could be found.

Results

MNC was not detected in the serum of fasting humans.

BHB appeared in serum samples obtained from subjects after a food restricted 20 hour fast.

BHB was not detected in serum samples obtained from subjects in the fed state.

Little to no BHB was detected in the urine of subjects collected before and after the 20 hour fast.

Conclusions

MNC, found in BDI, was not found in fasting human serum or urine.

Serum and urine from fasting humans contains BHB.

Dosage Formulations

After BDI (containing both BHB and MNC) alone or in combination with existing identified metabolites of denning bears which are also found in humans, has been isolated as set forth above, it is combined with desirable solvents such as saline or 5% dextrose in water.

After the solvents have been applied, a carrier may also be involved. Such carriers include; peanut oil, propylene glycol, a 5% alcohol based elixir, or pills and capsules containing lactose and/or calcium carbonate fillers. Transdermals are available as an alternative means of delivering the necessary doses of BDI. For subcutaneous, intramuscular, intravenous, or other specialized routes such as into the cerebral spinal fluid, appropriate carriers such as saline, Ringer's lactate, or dextrose solutions may be used. BDI is stable, water soluble, and will not suffer dissolution after stirring or settling overnight.

Once the syringe has been loaded, or the pill compounded, the maximum dosages (which must first be assessed for safety) are calculated for the animal to be tested. The present means to predict maximum dosage was based only on the lyophilized BDI contained in aliquots of 50 ml of denning bear urine that also contained 200 micrograms ($\mu$g) of MNC. Next, the blood volume of the recipient is equated with 50 ml urine volumes from the bear. The concentration of MNC in 50 ml of urine is used for calculations. Mammals have blood volumes of approximately 5% of total body weight. Therefore, a 1000 gram guinea pig has 0.05×1000 g=50 ml blood.

Fifty milliliters denning bear urine containing between 2.0 and 3.6 grams of BDI also contains 200 micrograms ($\mu$g) MNC or 4 $\mu$g/ml.

Therefore, the dosage and formulation for a 1000 gram guinea pig was BDI containing 200 $\mu$MNC, which equaled a dose of 0.2 $\mu$g MNC/g body weight.

Reaffirmation of Findings: Urea recycling is produced when BDI injected into guinea pigs but not necessarily its basic components.

A urea creatinine ratio indicative of urea recycling (10 or less) was produced when BDI was injected into guinea pigs. This effect of efficient recycling lasted for three days after the injection. BDI was then separated into its three basic components. These were done previously as set forth in connection with the Table 1. The three basic components were BDI minus (BHB+MNC); BHB; and MNC. When each of these three basic components was injected seperately into guinea pigs, the urine of guinea pigs did not exhibit a urea to creatine ratio of urea recycling (see Table 16).

TABLE 16

Urine Urea to Creatine Ratio in Guinea Pigs For Three Days Post-Injection

| Treatment | Day 1 | Day 2 | Day 3 |
|---|---|---|---|
| Control: Average U/C Ratio | 34.28 | 34.28 | 34.28 |
| Group A: BDI − (BHB + MNC) (Contains 0.185 g urea) | 26.33 | 22.13 | 26.09 |
| Group B: BHB | 31.86 | 29.45 | 23.69 |
| Group C: MNC Through Wash | 26.23 | 33.20 | 34.55 |
| Group D: BDI (Contains 1.1 g urea) | 8.33 | 12.25 | 7.66 |
| Group E: Saline Control | 17.39 | 13.01 | 14.93 |

Thus, the combination of some substances contained in Fractions 1–17 of Table 1 (BDI minus [BHB+MNC]) and some substances from the fractions associated with BHB and/or NNC stimulate urea recycling.

Some of the individual components of these fractions are now known. The combination of the active substances in each fraction will stimulate urea recycling in the guinea pig, as distinguished from the lack of significant recycling when the three separate components are injected separately.

Further Refinement of Separation Techniques for BDI Isolated from Denning Bear Urine to: 1) Search for the Fractions in BDI Responsible for Stimulation of Osteoblasts 2) Identify Known Chemicals in the Ten Fractions of BDI, and 3) Further Purify the Fractions of BDI by HPLC in order to Identify Structural Components of MNC by Nuclear Magnetic Resonance and Mass Spectrometry.

Chemical methods of obtaining BDI fractions and isolating the same were performed as previously set forth in Table 1. To support further analysis, ten newly defined fractions from the countercurrent coil were collected. For example, the new Fraction I was obtained by pooling the first five elutions acquired from the countercurrent centrifuge. Total volume per collection tube was 20 ml; therefore, Fraction I contains 100 ml.

The precise countercurrent apparatus and centrifuge is manufactured by P.C., Inc. of Potomac, Md., referred to as a Multi-Layer Coil CCC. The #10 coil having a volume of 385 ml was used in processing all of the elutions and rinse which resulted in new Fractions 1–X (Table 17).

TABLE 17

Separation of BDI-Into Ten Fractions After CCC

| New Fractions | CCC Fractions |
|---|---|
| Fraction I | 1–5 |
| Fraction II | 6–10 |
| Fraction III | 11–15 |
| Fraction IV | 16–20 |
| Fraction V | 21–25 |
| Fraction VI | 26–30 |
| Fraction VII | 31–35 |
| Fraction VIII | 36–40 |
| Fraction IX | 41–45 |
| Fraction X | Methanol Wash |

The mobile phase (lower phase of 1-butanol:water:acetic acid, 20:20.1 mixture) of the first six of ten fractions were pumped through the CCC at 4 ml/minute. Collections were taken every twenty-five minutes. After collection of Fraction VI, the coil was stopped. Mobile phase continued pumping at an increased rate of 10 ml/minute. Collections were made at ten minute intervals. The mobile phase was discontinued while a 1:1 mixture of methanol and water was begun before beginning collection of Fraction IX. The methanol/water mixture was switched to 100% methanol at the beginning of Fraction X. After ten minutes, the pump was stopped and the coil was emptied by forcing compressed air through it. Everything collected from the coil at this point was added to Fraction X. All fractions were stored at −70° C. until lyophilization.

Search for Site of Osteoblast Stimulation in BDI

A sample of urine collected from a single denning bear was deproteinated and lyophilized. Up to one gram of BDI was then loaded on the CCC and separated into ten fractions through the procedure diagrammed in Table 17. Weights were obtained for each fraction. Fractions obtained from four separate runs of the CCC were combined before use in osteoblast cultures.

Each combined fraction was tested in a mouse calvaria bioassay to determine its effectiveness in stimulating osteoblasts. An increase in alkaline phosphatase production was interpreted as osteoblast stimulation.

The ability of each combined fraction to stimulate alkaline phosphatase in the mouse calvaria bioassay was measured and expressed as a percent of control. This was compared to the ability of BDI and of pooled blood serum from denning bears to stimulate alkaline phosphatase in the mouse calvaria bioassay (Table 18).

TABLE 18

Percent Stimulation of Osteoblast Activity By Blood Serum, Bear Derived Isolate, and Its Fractions

| Sample | Percent Above Control/mg Specimen |
|---|---|
| Fraction III | 23 |
| Fraction II | 78 |
| BDI (Bear Derived Isolate) | 75 |
| BS (Blood Serum) | 322 |
| Fraction X | 292 |
| Fraction IV | 401 |
| Fraction IX | 571 |
| Fraction V | 3,740 |
| Fraction VI | 4,281 |
| Fraction VII | 37,432 |

Fraction II,
BDI,
Pooled blood serum from denning bears,
Fraction X,
Fraction IV,
Fraction IX,
Fraction V,
Fraction VI, and
Fraction VII demonstrated stimulation of osteoblast activity. Fraction III inhibited osteoblast activity. Thus, Fraction III has the potential to arrest Paget's disease and other forms of neoplasms such as cancer resulting from overactivity of osteoblastic-induced bone growth. For a list of substance identified for Fraction III see Tables 19 and 20.

TABLE 19

QUANTIFIED TARGET PANEL
URINE ORGANIC COMPOUNDS
FRACTION III, BEAR URINE
JZ4061: 5

| | mM/M CREATININE | Nrml Range |
|---|---|---|
| Organic Acids | | |
| LACTIC ACID | 0 | 0–75 |
| PYRUVIC ACID | 0 | 0–20 |

TABLE 19-continued

QUANTIFIED TARGET PANEL
URINE ORGANIC COMPOUNDS
FRACTION III, BEAR URINE
JZ4061: 5

| | mM/M CREATININE | Nrml Range |
|---|---|---|
| GLYCOLIC ACID | 6 | 0–50 |
| ALPHA-OH-BUTYRIC | 0.0 | 0–1 |
| OXALIC | 0.0 | 0–25 |
| 4-OH-BUTYRIC | 0.0 | 0–1 |
| HEXANOIC ACID | 0.2 | 0–11 |
| 5-HYDROXYCAPROIC | 4.4 | 0–1 |
| OCTANOIC | 0.0 | 0–1 |
| BETA-LACTATE | 0.0 | 0–8 |
| SUCCINIC ACID | 0 | 0–20 |
| GLUTARIC ACID | 0.4 | 0–2 |
| 2-OXO-GLUTARATE | 0 | 0–210 |
| FUMARIC | 0.0 | 0–5 |
| MALEIC | 0.0 | 0 |
| MALIC ACID | 28.1 | 0–2 |
| ADIPIC ACID | 0.0 | 0–7 |
| SUBERIC ACID | 1.0 | 0–11 |
| SEBACIC ACID | 0.0 | 0–2 |
| GLYCERIC ACID | 0 | 0–4 |
| BETA-OH-BUTYRIC | 0 | 0–3 |
| METHYLSUCCINIC | 0.0 | 0 |
| METHYLMALONIC | 0 | 0–5 |
| ETHYLMALONIC | 0.0 | 0–4 |
| HOMOGENTISIC ACID | 0.0 | 0–1 |
| PHENYLPYRUVIC ACID | 0.1 | 0–1 |
| SUCCINYLACETONE | 0.0 | 0–1 |
| 3-OH-ISOVALERIC | 0.0 | 0–21 |
| PHOSPHATE | 90 | 0–3000 |
| CITRIC ACID | 24 | 0–450 |
| HIPPURIC ACID | 11 | 0–2000 |
| URIC ACID | 0 | 0–360 |
| Nutritionals | | |
| KYNURENIC ACID | 0.6 | |
| FORMIMINOGLUTAMIC | 0.15 | 0–3 |
| 4-PYRIDOXIC ACID | 0.2 | 0–9 |
| PANTOTHENIC ACID | 14 | 0–30 |
| XANTHURENIC ACID | 0.0 | 0–1 |
| KYNURENINE | 0.1 | 0–1 |
| QUINOLINIC | 0.0 | 0–6 |
| OROTIC ACID | 0.00 | 0–3 |
| D-AM LEVULINIC | 4.0 | 0–18 |
| 3-METHYL HISTIDINE | 0 | 0–75 |
| NIACINAMIDE | 0.0 | 0–1 |
| PSEUDOURIDINE | 58 | 10–220 |
| 2-DEOXYTETRONIC | 0 | 0–75 |
| P-HO-PHEN-ACETIC | 0 | 0–12 |
| XANTHINE | 0 | 0–18 |
| UROCANIC ACID | 0 | 0–3 |
| ABSCORBIC ACID | 1 | 0–160 |
| GLYCEROL | 0 | 0–9 |
| Carbohydrates | | |
| THREITOL | 0 | 0–40 |
| ERYTHRITOL | 0 | 0–55 |
| ARABINOSE | 0 | 0–30 |
| FUCOSE | 0.7 | 0–12 |
| RIBOSE | 3.2 | 0–12 |
| XYLOSE | 0 | 0–70 |
| FRUCTOSE | 0 | 0–115 |
| GLUCOSE | 3 | 0–110 |
| GALACTOSE | 20 | 0–200 |
| MANNOSE | 10 | 0–70 |
| N-AC-GLUCOSAMINE | 1.0 | 0–3 |
| LACTOSE | 2 | 0–60 |
| MALTOSE | 1 | 0–40 |
| XYLITOL | 0.1 | 0–15 |
| ARABINITOL | 0.0 | 0–30 |
| RIBITOL | 0.0 | 0–10 |
| ALLOSE | 1.4 | 0–10 |
| GLUCURONIC ACID | 113.6 | 0–50 |
| GALACTONIC ACID | 12 | 0–60 |

TABLE 19-continued

QUANTIFIED TARGET PANEL URINE ORGANIC COMPOUNDS FRACTION III, BEAR URINE JZ4061: 5

|  | mM/M CREATININE | Nrml Range |
|---|---|---|
| GLUCONIC ACID | 5.2 | 0–35 |
| GLUCARIC | 2.2 | 0–5 |
| MANNITOL | 11.5 | 0–15 |
| DULCITOL | 2.2 | 0–10 |
| SORBITOL | 3.2 | 0–10 |
| INOSITOL | 3.4 | 0–12 |
| SUCROSE | 0 | 0–75 |
| Neurotransmitters | | |
| GABA | 0.0 | 0–1 |
| HOMOVANILLIC ACID | 0.0 | 0–10 |
| NORMETANEPHRINE | 0.0 | 0–1 |
| VANILLYLMANDELIC | 0.0 | 0–6 |
| METANEPHRINE | 0.1 | 0–2 |
| 5-HIAA | 0.0 | 0–6 |
| MHPG | 0.0 | 0–1 |
| ETHANOLAMINE | 0 | 10–90 |
| Amino Acids and Glycine Conjugates | | |
| PROPIONYL GLY | 0.3 | 0–1 |
| BUTYRYL GLYCINE | 0.1 | 0–1 |
| HEXANOYL GLYCINE | 0.1 | 0–1 |
| PHENYL PROP GLY | 0.0 | 0–1 |
| SUBERYL GLYCINE | 0.0 | 0–1 |
| ISOVALERYL GLY | 0.0 | 0–1 |
| TIGLY GLY | 0.0 | 0–1 |
| BETA MET CROT GLY | 0.0 | 0–1 |
| GLYCINE | 1 | 0–500 |
| ALANINE | 2 | 0–130 |
| SARCOSINE | 0.0 | 0–8 |
| BETA-ALANINE | 0.1 | 0–2 |
| B-AMINOISOBUTYRIC | 0 | 0–50 |
| SERINE | 0 | 0–85 |
| PROLINE | 0.0 | 0–8 |
| HYDROXY PROLINE | 0 | 0–75 |
| HYDROXY LYSINE | 0.1 | 0–1 |

TABLE 19-continued

QUANTIFIED TARGET PANEL URINE ORGANIC COMPOUNDS FRACTION III, BEAR URINE JZ4061: 5

|  | mM/M CREATININE | Nrml Range |
|---|---|---|
| ASPARTIC ACID | 0.0 | 0–2 |
| ASPARAGINE | 0.0 | 0–2 |
| N-AC ASPARTIC | 0.0 | 0–20 |
| ORNITHINE | 0.1 | 0–5 |
| GLUTAMIC ACID | 0.1 | 0–6 |
| GLUTAMINE | 1 | 0–210 |
| PIPECOLIC ACID | 0.1 | 0–1 |
| LEUCINE | 0.0 | 0–9 |
| KETO LEUCINE | 0.0 | 0–1 |
| VALINE | 0.0 | 0–18 |
| KETO-VALINE | 0.0 | 0–1 |
| ISOLEUCINE | 0.0 | 0–5 |
| KETO-ISOLEUCINE | 1.0 | 0–1 |
| LYSINE | 1 | 0–35 |
| HISTIDINE | 1 | 0–225 |
| THREONINE | 0 | 0–45 |
| HOMOSERINE | 0.3 | 0–1 |
| METHIONINE | 0.0 | 0–3 |
| CYSTEINE | 0 | 0–160 |
| HOMOCYSTEINE | 0.0 | 0–1 |
| CYSTATHIONINE | 0.1 | 0–1 |
| HOMOCYSTINE | 0.0 | 0–1 |
| CYSTINE | 0.1 | 0–5 |
| PHENYLALANINE | 16 | 0–20 |
| TYROSINE | 1 | 0–22 |
| TRYPTOPHAN | 0 | 0–25 |

TABLE 20

METABOLIC SCREENING LABORATORY URINE ORGANIC CONSTITUENTS FRACTION III, BEAR URINE JZ4061
CONCENTRATION: THIS SAMPLE CONTAINED 20.72 mM CREATININE/mL

| PEAK # | CONSTITUENT'S BEST MATCH FROM LIBRARY* | LIB ENTRY | FIT vs 1000 | AREA % | AREA OF CREAT |
|---|---|---|---|---|---|
| 18 | 24, NU3131 | 2125 | 767 | 1.18 | 72.24 |
| 25 | 25 | 0 | 0 | 2.75 | 167.69 |
| 32 | 32 | 0 | 0 | 0.07 | 4.42 |
| 57 | 57 | 0 | 0 | 0.14 | 8.41 |
| 68 | 1,3 PROPANEDIOL DI-TMS | 1675 | 854 | 0.35 | 21.28 |
| 78 | 78 | 0 | 0 | 0.30 | 18.24 |
| 83 | PROPENE GLYCOL DI-TMS | 50 | 868 | 0.86 | 52.40 |
| 94 | GLYCOLIC ACID DI-TMS | 55 | 925 | 1.83 | 111.85 |
| 97 | GLYCOLIC ACID DI-TMS | 55 | 947 | 1.46 | 88.88 |
| 101 | 92, NA3011 | 2070 | 711 | 0.09 | 5.63 |
| 112 | 104, NJ3031 | 2131 | 834 | 1.87 | 114.25 |
| 181 | 107, KA1051 | 2050 | 712 | 0.08 | 4.73 |
| 243 | 4-HYDROXY BUTYRIC ACID DI-TMS | 97 | 799 | 0.12 | 7.40 |
| 257 | MALONIC ACID DI-TMS | 100 | 760 | 0.09 | 5.38 |
| 323 | PHOSPHATE TRI-TMS | 1413 | 929 | 0.16 | 9.94 |
| 351 | PHOSPHATE TRI-TMS | 1413 | 834 | 0.13 | 7.80 |
| 357 | PHOSPHATE TRI-TMS | 1413 | 852 | 0.60 | 36.50 |
| 362 | PHOSPHATE TRI-TMS | 1413 | 925 | 0.41 | 25.17 |
| 382 | PHOSPHATE TRI-TMS | 1413 | 933 | 0.08 | 4.58 |
| 387 | PHOSPHATE TRI-TMS | 1413 | 804 | 0.70 | 42.71 |

TABLE 20-continued

METABOLIC SCREENING LABORATORY
URINE ORGANIC CONSTITUENTS
FRACTION III, BEAR URINE
JZ4061
CONCENTRATION: THIS SAMPLE CONTAINED 20.72 mM CREATININE/mL

| PEAK # | CONSTITUENT'S BEST MATCH FROM LIBRARY* | LIB ENTRY | FIT vs 1000 | AREA % | AREA OF CREAT |
|---|---|---|---|---|---|
| 409 | 409 | 0 | 0 | 0.23 | 14.03 |
| 423 | 409, JZ4061 | 2327 | 959 | 0.73 | 44.75 |
| 430 | 409, JZ4061 | 2327 | 928 | 0.58 | 35.39 |
| 462 | 283, NF3091 | 2093 | 733 | 0.12 | 7.05 |
| 486 | GLYCERIC ACID TRI-TMS | 324 | 626 | 0.75 | 45.99 |
| 513 | 283, NF3091 | 2093 | 747 | 0.11 | 6.47 |
| 527 | 283, NF3091 | 2093 | 745 | 0.18 | 11.14 |
| 600 | 2, 4 DIHYDROXYBUTYRIC ACID TRI-TMS | 1889 | 922 | 0.23 | 13.89 |
| 628 | 628 | 0 | 0 | 0.09 | 5.22 |
| 638 | 3, 4 DIHYDROXY BUTYRIC ACID TRI-TMS | 361 | 887 | 0.88 | 53.73 |
| 658 | CITRAMALIC ACID TRI-TMS, 675 | 2103 | 703 | 0.13 | 8.17 |
| 664 | 645, M27041 | 1836 | 863 | 0.13 | 7.74 |
| 694 | CITRAMALIC ACID TRI-TMS, 675 | 2103 | 940 | 0.17 | 10.30 |
| 738 | 2-DEOXY PENTONIC ACID GAMMA LACTONE DI-TMS | 176 | 795 | 0.15 | 8.91 |
| 764 | 1-AMINO CYCLOPENTANE CARBOXYLIC ACID DI-TMS | 158 | 614 | 4.40 | 268.70 |
| 773 | TETROSE TRI-TMS | 362 | 938 | 3.31 | 202.06 |
| 787 | TETROSE TRI-TMS | 362 | 941 | 9.36 | 571.10 |
| 800 | 3-METHYL-2-TENTENEDIOIC ACID DI-TMS | 2004 | 726 | 0.07 | 4.32 |
| 813 | CREATININE ENOL TRI-TMS | 1467 | 865 | 1.68 | 102.41 |
| 819 | TETROSE TRI-TMS | 362 | 683 | 1.09 | 66.57 |
| 825 | 4 DE-O TETRONIC TMS3, THREO | 1649 | 671 | 0.65 | 39.52 |
| 836 | 4 DE-O TETRONIC TMS3, THREO | 1649 | 902 | 5.55 | 338.69 |
| 859 | 4 DE-O TETRONIC TMS3; THREO | 1649 | 886 | 1.97 | 120.42 |
| 886 | ALANINE DI-TMS | 78 | 546 | 0.08 | 5.08 |
| 903 | PARA HYDROXY BENZOIC DI-TMS | 202 | 635 | 0.07 | 4.53 |
| 910 | D-ERYTHRO-PENTITOL, 2-DEOXY-1, 3, 4, 5-TETRAKIS- | 633 | 742 | 0.31 | 18.65 |
| 927 | 2, 2 DIMETHYL 3-HYDROXY BUTRIC ACID DI-TMS | 180 | 546 | 0.58 | 35.27 |
| 943 | LACTULOSE METABOLITE? | 1751 | 847 | 0.76 | 46.27 |
| 951 | ARABINOFURANOSE TETRA-TMS | 675 | 855 | 0.26 | 16.12 |
| 963 | GLYCOLIC ACID DI-TMS | 55 | 319 | 0.97 | 59.40 |
| 972 | 981, M21021 | 1829 | 752 | 0.46 | 27.86 |
| 985 | RIBULOSE PER-TMS | 1848 | 749 | 0.88 | 53.83 |
| 996 | 996 | 0 | 0 | 1.31 | 79.71 |
| 1005 | 965, JJ4011 | 2191 | 708 | 0.27 | 16.69 |
| 1011 | ARABITOL | 1841 | 752 | 0.31 | 19.21 |
| 1019 | ARABITOL | 1841 | 664 | 0.15 | 9.44 |
| 1024 | 1024 | 0 | 0 | 0.30 | 18.25 |
| 1034 | D-ERYTHRO-HEX-2-ENOUIC ACID, DI-O-METHYLBIS-O | 404 | 581 | 0.07 | 4.18 |
| 1041 | 6-DEOXY MANNOSE TETRA-TMS | 719 | 873 | 0.28 | 16.91 |
| 1054 | ARABITOL | 1841 | 959 | 2.43 | 148.36 |
| 1060 | ARABINONIC ACID, 2, 3, 5-TRIS-O-TMS-, .GAMMA. -L | 464 | 731 | 0.17 | 10.45 |
| 1072 | ARABITOL | 1841 | 951 | 4.16 | 254.05 |
| 1077 | 1073, RT1051 | 2040 | 732 | 2.02 | 123.07 |
| 1099 | CYSTEINE TRI-TMS | 363 | 295 | 1.13 | 68.83 |
| 1107 | D-XYLOPYRANOSE TETRA-TMS | 679 | 783 | 0.93 | 56.63 |
| 1119 | 1357, M22011 | 1834 | 739 | 2.21 | 134.78 |
| 1126 | 6-DEOXY GLUCIOL PENTA-TMS | 858 | 913 | 1.24 | 75.79 |
| 1131 | 1107, NU3081 | 2122 | 683 | 1.62 | 99.10 |
| 1138 | 4 DE-O TETRONIC TMS3, THREO | 1649 | 691 | 0.97 | 59.50 |
| 1142 | 1142 | 0 | 0 | 0.11 | 6.54 |
| 1160 | PROPANOIC ACID, 3- BIS TMS-OXY PHOSPHINYL OX | 756 | 696 | 0.14 | 8.75 |
| 1167 | CREATININE TETRA-TMS | 1438 | 603 | 0.87 | 52.90 |
| 1176 | ISO CITRIC ACID TETRA-TMS | 775 | 891 | 3.14 | 191.49 |
| 1185 | D-ARABINO-HEXITOL, 2-DEOXY-1, 3, 4, 5, 6-PENTAKIS | 856 | 584 | 0.45 | 27.57 |
| 1195 | 1195 | 0 | 0 | 0.13 | 7.81 |
| 1203 | 1357, M22011 | 1834 | 683 | 1.48 | 90.53 |
| 1226 | 1224, YE1011 | 1884 | 638 | 0.99 | 60.32 |
| 1234 | 1234 | 0 | 0 | 0.08 | 5.12 |
| 1246 | 1246 | 0 | 0 | 0.99 | 60.46 |
| 1254 | GALACTOSE PENTA-TMS | 878 | 707 | 0.57 | 34.80 |
| 1258 | NEO-INOSITOL HEXA-TMS | 972 | 835 | 1.15 | 70.49 |
| 1269 | BENZOIC ACID, 5-METHOXY-2- TMS-OXY - TRIMETH | 293 | 336 | 0.33 | 20.21 |
| 1276 | GLUCONIC ACID, 2, 3, 5, 6-TETRAKIS-O-TMS- LACTO | 737 | 816 | 0.73 | 44.42 |
| 1288 | 3, 4, 5 TRIHYDROXY FURAN 2-ACETALDEHYDE TETRA-T | 743 | 680 | 0.31 | 18.72 |
| 1301 | GLUCITOL TRI-TMS | 979 | 899 | 1.51 | 92.20 |
| 1308 | GLUCITOL TRI-TMS | 979 | 895 | 1.60 | 97.44 |
| 1312 | DULCITOL | 1840 | 926 | 0.78 | 47.33 |
| 1318 | 1315, YE1011 | 1885 | 837 | 0.55 | 33.52 |
| 1325 | 2-DEOXY ERYTHROPENTONIC ACID TETRA-TMS | 687 | 446 | 0.59 | 36.15 |
| 1334 | GALACTONIC ACID HEXA-TMS | 988 | 888 | 3.31 | 201.84 |

TABLE 20-continued

METABOLIC SCREENING LABORATORY
URINE ORGANIC CONSTITUENTS
FRACTION III, BEAR URINE
JZ4061
CONCENTRATION: THIS SAMPLE CONTAINED 20.72 mM CREATININE/mL

| PEAK # | CONSTITUENT'S BEST MATCH FROM LIBRARY* | LIB ENTRY | FIT vs 1000 | AREA % | AREA OF CREAT |
|---|---|---|---|---|---|
| 1354 | TALOSE PENTA-TMS | 896 | 883 | 0.45 | 27.31 |
| 1369 | GALACTONIC ACID HEXA-TMS | 988 | 789 | 0.58 | 35.69 |
| 1377 | GALACTARIC ACID HEXA-TMS | 993 | 772 | 0.46 | 27.82 |
| 1384 | GALACTONIC ACID HEXA-TMS | 988 | 811 | 0.83 | 50.75 |
| 1391 | 2-DEOXY ERYTHROPENTONIC ACID TETRA-TMS | 687 | 529 | 0.20 | 12.26 |
| 1395 | SCYLLO-INOSITOL HEXA-TMS | 969 | 799 | 1.35 | 82.37 |
| 1403 | .BETA.PHENYLPYRUVIC ACID DI-TMS | 280 | 205 | 0.59 | 36.22 |
| 1424 | ARABITOL | 1841 | 584 | 1.31 | 79.85 |
| 1438 | ARABITOL | 1841 | 548 | 0.78 | 47.66 |
| 1443 | MUCO-INOSITOL HEXA-TMS | 974 | 802 | 0.98 | 59.86 |
| 1451 | XYLULOSE TETRA-TMS | 1771 | 658 | 0.17 | 10.36 |
| 1460 | 1460 | 0 | 0 | 0.08 | 4.63 |
| 1473 | 1473 | 0 | 0 | 0.06 | 3.85 |
| 1484 | 1484 | 0 | 0 | 0.07 | 4.16 |
| 1504 | 1504 | 0 | 0 | 0.07 | 4.18 |
| 1553 | .BETA. -D-GALACTOFURANOSE, 1, 2, 3, 5, 6-PENTAKIS- | 880 | 625 | 0.09 | 5.69 |
| 1561 | 1561 | 0 | 0 | 0.29 | 17.73 |
| 1591 | 1591 | 0 | 0 | 0.06 | 3.84 |
| 1596 | PSEUDO URIDINE PENTA-TMS | 1779 | 792 | 1.91 | 116.63 |
| 1615 | D-RIBOFURANOSE TETRA-TMS | 685 | 762 | 0.65 | 39.75 |
| 1658 | 1658 | 0 | 0 | 0.27 | 16.45 |
| 1704 | D-XYLOPYRANOSE TETRA-TMS | 679 | 650 | 0.08 | 4.71 |
| 1726 | ARABINONIC ACID, 2, 3, 4-TRIS-O-TMS-, LACTONE, | 461 | 629 | 0.08 | 5.11 |
| 1801 | 6-DEOXY MANNOSE TETRA-TMS | 719 | 855 | 0.20 | 12.13 |

*The named compound matches the sample peak with a reliability given by "FIT"/1000

When results of this bioassay were expressed per mg of sample to represent potency of the sample, Fraction V, Fraction VI, and Fraction VII demonstrated the highest potency (Table 18). Fraction V exhibited a fifty-fold increase in potency when compared with BDI and a twelve-fold increase over the pooled denning bear serum. Similarly, Fraction VI exhibited a fifty-seven fold increase in potency when compared with BDI and a thirteen-fold increase over the pooled denning bear serum; Fraction VII exhibited a five hundred fold increase in potency when compared with BDI and a one hundred seventeen fold increase over pooled denning bear serum.

Identification of Known Substances in the Ten Fractions of BDI

The ten fractions of BDI collected from the CCC (including Fraction III above) were submitted to Dr. James Shoemaker, Director of the Metabolic Screening Laboratory and Assistant Professor of Biochemistry and Medicine in the College of Medicine, St. Louis University, St. Louis, Mo., for analysis by gas chromatography and mass spectrometry (GCfMS). The mass spectra of trimethylsilyl derivatives of the compounds in the CCC fractions were compared to a database of more than forty thousand chemicals.

Tables 21 and 22 depict data generated from Fraction V. Tables 23 and 24 depict data generated from Fraction VI; Tables 25 and 26 depict data generated from Fraction VII. Data on retention times are available for the substances depicted in Tables 19 through 38.

TABLE 21

QUANTIFIED TARGET PANEL
URINE ORGANIC COMPOUNDS
FRACTION V, BEAR URINE
JZ4081:7

| | um/L* | Nrml Range |
|---|---|---|
| Organic Acids | | |
| LACTIC ACID | 55124 | |
| PYRUVIC ACID | 10460 | |
| GLYCOLIC ACID | 1123 | |
| ALPHA-OH-BUTYRIC | 1274.5 | |
| OXALIC | 0.0 | |
| 4-OH-BUTYRIC | 0.0 | |
| HEXANOIC ACID | 0.0 | |
| 5-HYDROXYCAPROIC | 0.0 | |
| OCTANOIC | 0.0 | |
| BETA-LACTATE | 0.0 | |
| SUCCINIC ACID | 23256 | |
| GLUTARIC ACID | 0.0 | |
| 2-OXO-GLUTARATE | ***** | |
| FUMARIC | 0.0 | |
| MALEIC | 0.0 | |
| MALIC ACID | 0.0 | |
| ADIPIC ACID | 0.0 | |
| SUBERIC ACID | 0.0 | |
| SEBACIC ACID | 0.0 | |
| GLYCERIC ACID | 0.0 | |
| BETA-OH-BUTYRIC | 2026.0 | |
| METHYLSUCCINIC | 0.0 | |
| METHYLMALONIC | 0.0 | |
| ETHYLMALONIC | 0.0 | |
| HOMOGENTISIC ACID | 0.0 | |
| PHENYLPYRUVIC ACID | 0.0 | |

TABLE 21-continued

QUANTIFIED TARGET PANEL
URINE ORGANIC COMPOUNDS
FRACTION V, BEAR URINE
JZ4081:7

|  | um/L* | Nrml Range |
|---|---|---|
| SUCCINYLACETONE | 0.0 | |
| 3-OH-ISOVALERIC | 231.5 | |
| PHOSPHATE | 2.19 | mg/dL |
| CITRIC ACID | 2865 | |
| HIPPURIC ACID | 486 | |
| URIC ACID | 0.59 | mg/dL |
| Nutritionals | | |
| FORMIMINOGLUTAMIC | 0.00 | |
| 4-PYRIDOXIC ACID | 0.0 | |
| PANTOTHENIC ACID | 0 | |
| XANTHURENIC ACID | 0.0 | |
| KYNURENINE | 0.0 | |
| QUINOLINIC | 1871.0 | |
| OROTIC ACID | 0.0 | |
| D-AM LEVULINIC | ***** | |
| 3-METHYL HISTIDINE | ***** | |
| NIACINAMIDE | 1121.0 | |
| PSEUDOURIDINE | 11063 | |
| 2-DEOXYTETRONIC | 0 | |
| P-HO-PHEN-ACETIC | 30 | |
| XANTHINE | 0 | |
| UROCANIC ACID | 0 | |
| ABSCORBIC ACID | 0 | |
| GLYCEROL | 7963.0 | |
| Carbohydrates | | |
| THREITOL | 0 | |
| ERYTHRITOL | 0 | |
| ARABINOSE | 0 | |
| FUCOSE | 0.0 | |
| RIBOSE | 0.0 | |
| XYLOSE | 0 | |
| FRUCTOSE | 0 | |
| GLUCOSE | 23 | mg/dL |
| GALACTOSE | 0 | |
| MANNOSE | 84 | |
| N-AC-GLUCOSAMINE | 0.0 | |
| LACTOSE | 2869 | |
| MALTOSE | 3113 | |
| XYLITOL | 0.0 | |
| ARABINITOL | 0.0 | |
| RIBITOL | 0.0 | |
| ALLOSE | 105.0 | |
| GLUCURONIC ACID | 2467.5 | |
| GALACTONIC ACID | 0 | |
| GLUCONIC ACID | 0.0 | |
| GLUCARIC | 0.0 | |
| MANNITOL | 69.5 | |
| DULCITOL | 0.0 | |
| SORBITOL | 0.0 | |
| INOSITOL | 0.0 | |
| SUCROSE | 6311 | |
| Neurotransmitters | | |
| GABA | 562.0 | |
| HOMOVANILLIC ACID | 0.0 | |
| NORMETANEPHRINE | 0.0 | |
| VANILLYLMANDELIC | ***** | |
| METANEPHRINE | 20.0 | |
| 5-HIAA | 0.0 | |
| MHPG | 500.0 | |
| ETHANOLAMINE | 8655 | |
| Amino Acids and Glycine Conjugates | | |
| PROPIONYL GLY | 863.0 | |
| BUTYRYL GLYCINE | ***** | |
| HEXANOYL GLYCINE | 856.5 | |
| PHENYL PROP GLY | 0.0 | |
| SUBERYL GLYCINE | 49.0 | |
| ISOVALERYL GLY | 0.0 | |
| TIGLY GLY | ***** | |
| BETA MET CROT GLY | 0.0 | |
| GLYCINE | 15925 | |
| ALANINE | 192 | |
| SARCOSINE | 86.0 | |
| BETA-ALANINE | 0.0 | |
| B-AMINOISOBUTYRIC | 798 | |
| SERINE | 12428 | |
| PROLINE | 1351.0 | |
| HYDROXY PROLINE | 15079 | |
| HYDROXY LYSINE | 0.0 | |
| ASPARTIC ACID | 3027.5 | |
| ASPARAGINE | 0.0 | |
| N-AC ASPARTIC | 0.0 | |
| ORNITHINE | 393.5 | |
| GLUTAMIC ACID | 952.5 | |
| GLUTAMINE | 577 | |
| PIPECOLIC ACID | 0.0 | |
| LEUCINE | 1799.0 | |
| KETO LEUCINE | ***** | |
| VALINE | 3449.0 | |
| KETO-VALINE | 0.0 | |
| ISOLEUCINE | 1277.5 | |
| KETO-ISOLEUCINE | 0.0 | |
| LYSINE | 43 | |
| HISTIDINE | 0 | |
| THREONINE | 1750 | |
| HOMOSERINE | 0.0 | |
| METHIONINE | 599.0 | |
| CYSTEINE | ***** | |
| HOMOCYSTEINE | 0.0 | |
| CYSTATHIONINE | 0.0 | |
| HOMOCYSTINE | 0.0 | |
| CYSTINE | 0.0 | |
| PHENYLALANINE | 860.5 | |
| TYROSINE | 1398 | |
| TRYPTOPHAN | 183.5 | |

THIS SAMPLE CONTAINED 130.58 mg Creatinine/dL

*The numbers above are best used to make the qualitative judgement of normal versus abnormal and not for direct quantitative comparisons.

TABLE 22

METABOLIC SCREENING LABORATORY
URINE ORGANIC CONSTITUTENTS
FRACTION V, BEAR URINE
JZ4081
CONCENTRATION: THIS SAMPLE CONTAINED 0.01 mM CREATININE/mL

| PEAK # | CONSTITUENT'S BEST MATCH FROM LIBRARY* | LIB ENTRY | FIT vs 1000 | AREA % | CREAT NOT FOUND |
|---|---|---|---|---|---|
| 7 | 10, STN031 | 1893 | 783 | 4.08 | |
| 19 | 16, 011031 | 1989 | 806 | 6.95 | |
| 34 | 31, NF3031 | 2090 | 757 | 0.78 | |
| 57 | 49, AK2011 | 2047 | 836 | 0.69 | |
| 66 | SILANE, TRIMETHYLPHENOXY- | 1122 | 887 | 2.82 | |
| 70 | ETHYL AMINE DI-TMS | 22 | 589 | 12.54 | |
| 77 | PROPENE GLYCOL DI-TMS | 50 | 867 | 0.84 | |
| 107 | 107, JZ4011 | 2301 | 787 | 0.79 | |
| 117 | 104, NJ3031 | 2131 | 860 | 12.78 | |
| 121 | 119, J04011 | 2243 | 922 | 1.09 | |
| 185 | BETA-LACTATE DI-TMS | 1654 | 773 | 2.17 | |
| 292 | 283, NF3091 | 2093 | 747 | 5.88 | |
| 361 | TRIMETHYLSILYL ETHER OF GLYCEROL | 273 | 917 | 0.77 | |
| 600 | 2-METHYL PROPANOATE GLYCINE CONJUGATE DI-TMS | 226 | 904 | 0.88 | |
| 707 | BUTYRIC ACID GLYCINE CONJUGATE DI-TMS | 225 | 904 | 2.12 | |
| 805 | METHYL D3 CREATININE TRI-TMS | 1466 | 745 | 8.61 | |
| 825 | BUTANEDIOIC ACID, OXO-TMS-, BIS-TMS-ESTER | 401 | 698 | 0.68 | |
| 878 | 878 | 0 | 0 | 1.72 | |
| 940 | 940 | 0 | 0 | 0.80 | |
| 1076 | CIS-ACONITIC ACID TRI-TMS | 540 | 874 | 2.34 | |
| 1111 | SALICYLIC ACID DI-TMS ORTHO-HYDROXY-BENZOIC | 1720 | 286 | 3.95 | |
| 1135 | 1135, JZ4011 | 2306 | 865 | 1.88 | |
| 1223 | VANILLYL MANDELIC ACID TRI-TMS | 610 | 898 | 1.73 | |
| 1284 | 1284 | 0 | 0 | 1.01 | |
| 1364 | 1364, JZ4011 | 2312 | 888 | 1.05 | |
| 1594 | 1594 | 0 | 0 | 17.08 | |
| 1604 | FROM GUAIFENESIN, 1813, NH3041 | 2169 | 688 | 6.27 | |
| 1788 | 1527, 0G1021 | 1987 | 631 | 1.79 | |

*The named compound matches the sample peak with a reliability given by "FIT"/1000

TABLE 23

QUANTIFIED TARGET PANEL
URINE ORGANIC COMPOUNDS
FRACTION VI, BEAR URINE
JZ4011:1

| | mM/M CREATININE | Nrml Range |
|---|---|---|
| Organic Acids | | |
| LACTIC ACID | 2531 | 0–75 |
| PYRUVIC ACID | 516 | 0–20 |
| GLYCOLIC ACID | 53 | 0–50 |
| ALPHA-OH-BUTYRIC | 6.9 | 0–51 |
| OXALIC | 70.3 | 0–25 |
| 4-OH-BUTYRIC | 0.0 | 0–1 |
| HEXANOIC ACID | 14.9 | 0–11 |
| 5-HYDROXYCAPROIC | 0.0 | 0–1 |
| OCTANOIC | 0.0 | 0–1 |
| BETA-LACTATE | 29.4 | 0–8 |
| SUCCINIC ACID | 49 | 0–20 |
| GLUTARIC ACID | 272.8 | 0–2 |
| 2-OXO-GLUTARATE | 26936 | 0–210 |
| FUMARIC | 24.1 | 0–5 |
| MALEIC | 0.0 | 0 |
| MALIC ACID | 1.5 | 0–2 |
| ADIPIC ACID | 3.7 | 0–7 |
| SUBERIC ACID | 5.7 | 0–11 |
| SEBACIC ACID | 0.0 | 0–2 |
| GLYCERIC ACID | 0 | 0–4 |
| BETA-OH-BUTYRIC | 55 | 0–3 |
| METHYLSUCCINIC | 8443.4 | 0 |
| METHYLMALONIC | 0 | 0–5 |
| ETHYLMALONIC | 0.0 | 0–4 |
| HOMOGENTISIC ACID | 25.6 | 0–1 |
| PHENYLPYRUVIC ACID | 7.7 | 0–1 |
| SUCCINYLACETONE | 2.6 | 0–1 |
| 3-OH-ISOVALERIC | 0.6 | 0–21 |
| PHOSPHATE | 8 | 0–3000 |
| CITRIC ACID | 507 | 0–450 |
| HIPPURIC ACID | 472 | 0–2000 |
| URIC ACID | 218 | 0–360 |
| Nutritionals | | |
| KYNURENIC ACID | 44.8 | |
| FORMIMINOGLUTAMIC | 0.00 | 0–3 |
| 4-PYRIDOXIC ACID | 0.0 | 0–9 |
| PANTOTHENIC ACID | 0 | 0–30 |
| XANTHURENIC ACID | 0.0 | 0–1 |
| KYNURENINE | 0.0 | 0–1 |
| QUINOLINIC | 0.0 | 0–6 |
| OROTIC ACID | 0.00 | 0–3 |
| D-AM LEVALINIC | 1657.1 | 0–18 |
| 3-METHYL HISTIDINE | 2 | 0–75 |
| NIACINAMIDE | 16.3 | 0–1 |
| PSEUDOURIDINE | 12665 | 10–220 |
| 2-DEOXYTETRONIC | 0 | 0–75 |
| P-HO-PHEN-ACETIC | 5 | 0–12 |
| XANTHINE | 38 | 0–18 |
| UROCANIC ACID | 47 | 0–3 |

TABLE 23-continued

QUANTIFIED TARGET PANEL URINE ORGANIC COMPOUNDS FRACTION VI, BEAR URINE JZ4011:1

| | mM/M CREATININE | Nrml Range |
|---|---|---|
| ASCORBIC ACID | 0 | 0–160 |
| GLYCEROL | 705 | 0–9 |
| Carbohydrates | | |
| THREITOL | 0 | 0–40 |
| ERYTHRITOL | 12 | 0–55 |
| ARABINOSE | 0 | 0–30 |
| FUCOSE | 0.4 | 0–12 |
| RIBOSE | 0.7 | 0–12 |
| XYLOSE | 0 | 0–70 |
| FRUCTOSE | 135 | 0–115 |
| GLUCOSE | 99 | 0–110 |
| GALACTOSE | 12 | 0–200 |
| MANNOSE | 54 | 0–70 |
| N-AC-GLUCOSAMINE | 2.7 | 0–3 |
| LACTOSE | 259 | 0–60 |
| MALTOSE | 127 | 0–40 |
| XYLITOL | 0.0 | 0–15 |
| ARABINITOL | 0.0 | 0–30 |
| RIBITOL | 0.0 | 0–10 |
| ALLOSE | 0.3 | 0–10 |
| GLUCURONIC ACID | 10.2 | 0–50 |
| GALACTONIC ACID | 15 | 0–60 |
| GLUCONIC ACID | 1.0 | 0–35 |
| GLUCARIC | 0.2 | 0–5 |
| MANNITOL | 10.2 | 0–15 |
| DULCITOL | 0.4 | 0–10 |
| SORBITOL | 9.7 | 0–10 |
| INOSITOL | 8.5 | 0–12 |
| SUCROSE | 1349 | 0–75 |
| Neurotransmitters | | |
| GABA | 1.0 | 0–1 |
| HOMOVANILLIC ACID | 5.6 | 0–10 |
| NORMETANEPHRINE | 41.3 | 0–1 |
| VANILLYLMANDELIC | 90.3 | 0–6 |
| METANEPHRINE | 1.1 | 0–2 |
| 5-HIAA | 1.2 | 0–6 |
| MHPG | 0.0 | 0–1 |
| ETHANOLAMINE | 409 | 10–90 |
| Amino Acids and Glycine Conjugates | | |
| PROPIONYL GLY | 0.0 | 0–1 |
| BUTYRYL GLYCINE | 1196.9 | 0–1 |
| HEXANOYL GLYCINE | 0.0 | 0–1 |
| PHENYL PROP GLY | 0.0 | 0–1 |
| SUBERYL GLYCINE | 0.0 | 0–1 |
| ISOVALERYL GLY | 0.0 | 0–1 |
| TIGLY GLY | 0.0 | 0–1 |
| BETA MET CROT GLY | 0.0 | 0–1 |
| GLYCINE | 1053 | 0–500 |
| ALANINE | 12 | 0–130 |
| SARCOSINE | 12.6 | 0–8 |
| BETA-ALANINE | 0.0 | 0–2 |
| B-AMINOISOBUTYRIC | 7 | 0–50 |
| SERINE | 1106 | 0–85 |
| PROLINE | 115.7 | 0–8 |
| HYDROXY PROLINE | 956 | 0–75 |
| HYDROXY LYSINE | 0.0 | 0–1 |
| ASPARTIC ACID | 232.4 | 0–2 |
| ASPARAGINE | 5.0 | 0–2 |
| N-AC ASPARTIC | 191.8 | 0–20 |
| ORNITHINE | 86.9 | 0–5 |
| GLUTAMIC ACID | 79.7 | 0–6 |
| GLUTAMINE | 4 | 0–210 |
| PIPECOLIC ACID | 0.0 | 0–1 |
| LEUCINE | 141.2 | 0–9 |
| KETO LEUCINE | 611.7 | 0–1 |
| VALINE | 272.9 | 0–18 |
| KETO-VALINE | 0.0 | 0–1 |
| ISOLEUCINE | 107.1 | 0–5 |
| KETO-ISOLEUCINE | 0.0 | 0–1 |
| LYSINE | 644 | 0–35 |
| HISTIDINE | 140 | 0–225 |
| THREONINE | 215 | 0–45 |
| HOMOSERINE | 0.0 | 0–1 |
| METHIONINE | 2.7 | 0–3 |
| CYSTEINE | 1122 | 0–160 |
| HOMOCYSTEINE | 0.0 | 0–1 |
| CYSTATHIONINE | 0.0 | 0–1 |
| HOMOCYSTINE | 0.0 | 0–1 |
| CYSTINE | 8.7 | 0–5 |
| PHENYLALANINE | 85 | 0–20 |
| TYROSINE | 68 | 0–22 |
| TRYPTOPHAN | 54 | 0–25 |

This sample contained 0.02 uMoles Creatinine/1.00 ml.

TABLE 24

METABOLIC SCREENING LABORATORY URINE ORGANIC CONSTITUENTS FRACTION VI, BEAR URINE JZ4011
CONCENTRATION: THIS SAMPLE CONTAINED 0.02 uM CREATININE/ml

| PEAK # | CONSTITUENT'S BEST MATCH FROM LIBRARY* | LIB ENTRY | FIT VS 1000 | AREA % | AREA % OF CREAT |
|---|---|---|---|---|---|
| 5 | 6, J14081 | 2189 | 780 | 1.67 | 422.70 |
| 8 | 10, STN031 | 1893 | 857 | 2.71 | 684.47 |
| 20 | 16, 011031 | 1989 | 820 | 5.76 | 1454.73 |
| 35 | 35 | 0 | 0 | 0.75 | 190.42 |
| 58 | 49, AK2011 | 2047 | 835 | 0.52 | 132.24 |

TABLE 24-continued

METABOLIC SCREENING LABORATORY
URINE ORGANIC CONSTITUENTS
FRACTION VI, BEAR URINE
JZ4011
CONCENTRATION: THIS SAMPLE CONTAINED 0.02 uM CREATININE/ml

| PEAK # | CONSTITUENT'S BEST MATCH FROM LIBRARY* | LIB ENTRY | FIT VS 1000 | AREA % | AREA % OF CREAT |
|---|---|---|---|---|---|
| 67 | SILANE, TRIMETHYLPHENOXY- | 1122 | 932 | 2.18 | 551.58 |
| 73 | 1,3 PROPANEDIOL DI-TMS | 1675 | 934 | 5.38 | 1358.88 |
| 78 | LACTIC ACID DI-TMS | 1510 | 927 | 0.74 | 187.43 |
| 107 | 107 | 0 | 0 | 0.59 | 148.59 |
| 118 | 104, NJ3031 | 2131 | 884 | 8.05 | 2032.64 |
| 122 | 119, J14011 | 2243 | 925 | 0.82 | 206.86 |
| 134 | BLYCINE DI-TMS | 51 | 822 | 0.25 | 64.34 |
| 186 | BETA-LACTATE DI-TMS | 1654 | 755 | 1.55 | 391.09 |
| 251 | 251 | 0 | 0 | 0.38 | 95.36 |
| 294 | UREA DI-TMS | 37 | 800 | 3.00 | 757.29 |
| 362 | TRIMETHYLSILYL ETHER OF GLYCEROL | 273 | 904 | 1.33 | 336.55 |
| 383 | OCTANOIC ACID, 2-OSO-, TRIMETHYLSILYL ESTER | 72 | 707 | 0.27 | 69.11 |
| 427 | METHYLSUCCINIC ACID DI-TMS | 173 | 948 | 3.17 | 799.71 |
| 502 | SERINE TRI-TMS | 322 | 958 | 0.51 | 128.24 |
| 697 | 3-METHYL-2-PENTENEDIOIC ACID DI-TMS | 2004 | 619 | 0.31 | 77.45 |
| 706 | BUTYRIC ACID GLYCINE CONJUGATE DI-TMS | 225 | 874 | 0.43 | 107.51 |
| 748 | HYDROXY PROLINE DI-TMS | 156 | 938 | 0.39 | 99.20 |
| 808 | METHYL D3 CREATININE TRI-TMS | 1466 | 705 | 12.91 | 3258.96 |
| 825 | BUTANEDIOIC ACID, OXO-TMS-, BIS-TMS-ESTER | 401 | 704 | 0.26 | 66.23 |
| 828 | 828 | 0 | 0 | 0.42 | 105.07 |
| 894 | PENTANEDIOIC ACID, 3-OXO-, TRIS-TMS ESTER | 448 | 923 | 0.46 | 116.34 |
| 901 | PARA HYDROXY BENZOIC DI-TMS | 202 | 912 | 0.38 | 95.59 |
| 964 | 964 | 0 | 0 | 1.16 | 293.82 |
| 1013 | 1013 | 0 | 0 | 0.39 | 97.24 |
| 1078 | CIS-ACONITIC ACID TRI-TMS | 540 | 839 | 6.15 | 1152.41 |
| 1111 | P-HO PHENYL GLYCOLIC TRI-TMS | 532 | 927 | 2.98 | 753.39 |
| 1135 | 1135 | 0 | 0 | 0.70 | 175.75 |
| 1141 | 1141 | 0 | 0 | 1.39 | 351.33 |
| 1167 | CITRIC ACID TETRA-TMS | 774 | 870 | 0.67 | 169.16 |
| 1192 | 1192 | 0 | 0 | 1.20 | 302.08 |
| 1215 | 1215 | 0 | 0 | 0.40 | 101.36 |
| 1223 | 1223 | 0 | 0 | 0.28 | 69.72 |
| 1252 | 1252 | 0 | 0 | 0.78 | 197.12 |
| 1364 | 1364 | 0 | 0 | 0.30 | 76.77 |
| 1370 | PALMITIC ACID TMS | 335 | 821 | 0.24 | 60.76 |
| 1389 | 289, ND3073 | 2073 | 678 | 1.49 | 377.32 |
| 1417 | PENTANEDIOIC ACID, 3,3-DIMETHYL-, BIS-TMS-EST | 260 | 418 | 0.50 | 125.53 |
| 1427 | 1427 | 0 | 0 | 0.55 | 138.13 |
| 1443 | URIC ACID TETRA-TMS | 1505 | 780 | 0.25 | 61.93 |
| 1462 | 1462 | 0 | 0 | 1.15 | 291.01 |
| 1492 | PARA-HYDROXYPHENYLACETIC GLYCINE CONJ TR | 2299 | 991 | 7.19 | 1816.50 |
| 1500 | 1481, NU3091 | 2124 | 782 | 8.74 | 2207.43 |
| 1596 | PSEUDO URIDINE PENTA-TMS | 1779 | 768 | 8.67 | 2189.48 |
| 1628 | 1472, VST031 | 2031 | 737 | 0.25 | 63.50 |
| 1746 | SUCROSE OCTA-TMS | 1080 | 924 | 1.05 | 265.38 |

*The named compound matches the sample peak with a reliability given by "FIT"/1000

TABLE 25

QUANTIFIED TARGET PANEL
URINE ORGANIC COMPOUNDS
FRACTION VII, BEAR URINE
JZ4021:2

| | mM/M CREATININE | Nrml Range |
|---|---|---|
| Organic Acids | | |
| LACTIC ACID | 2166 | 0–75 |
| PYRUVIC ACID | 211 | 0–20 |
| GLYCOLIC ACID | 24 | 0–50 |
| ALPHA-OH-BUTYRIC | 3.7 | 0–1 |
| OXALIC | 0.0 | 0–25 |
| 4-OH-BUTYRIC | 0.0 | 0–1 |
| HEXANOIC ACID | 7.4 | 0–11 |

TABLE 25-continued

QUANTIFIED TARGET PANEL
URINE ORGANIC COMPOUNDS
FRACTION VII, BEAR URINE
JZ4021:2

| | mM/M CREATININE | Nrml Range |
|---|---|---|
| 5-HYDROXYCAPROIC | 0.0 | 0–1 |
| OCTANOIC | 0.0 | 0–1 |
| BETA-LACTATE | 10.3 | 0–8 |
| SUCCINIC ACID | 7 | 0–20 |
| GLUTARIC ACID | 0.0 | 0–2 |
| 2-OXO-GLUTARATE | 0 | 0–210 |
| FUMARIC | 6.4 | 0–5 |
| MALEIC | 0.0 | 0 |
| MALIC ACID | 0.0 | 0–2 |

TABLE 25-continued

QUANTIFIED TARGET PANEL URINE ORGANIC COMPOUNDS FRACTION VII, BEAR URINE JZ4021:2

| | mM/M CREATININE | Nrml Range |
|---|---|---|
| ADIPIC ACID | 55.2 | 0–7 |
| SUBERIC ACID | 0.0 | 0–11 |
| SEBACIC ACID | 0.0 | 0–2 |
| GLYCERIC ACID | 0 | 0–4 |
| BETA-OH-BUTYRIC | 15 | 0–3 |
| METHYLSUCCINIC | 2082.5 | 0 |
| METHYLMALONIC | 0 | 0–5 |
| ETHYLMALONIC | 1711.8 | 0–4 |
| HOMOGENTISIC ACID | 14.6 | 0–1 |
| PHENYLPYRUVIC ACID | 3.4 | 0–1 |
| SUCCINYLACETONE | 10.4 | 0–1 |
| 3-OH-ISOVALERIC | 0.6 | 0–21 |
| PHOSPHATE | 208 | 0–3000 |
| CITRIC ACID | 58 | 0–450 |
| HIPPURIC ACID | 48 | 0–2000 |
| URIC ACID | 3 | 0–360 |
| Nutritionals | | |
| KYNURENIC ACID | 0.0 | |
| FORMIMINOGLUTAMIC | 0.00 | 0–3 |
| 4-PYRIDOXIC ACID | 0.0 | 0–9 |
| PANTOTHENIC ACID | 0 | 0–30 |
| XANTHURENIC ACID | 0.0 | 0–1 |
| KYNURENINE | 4.8 | 0–1 |
| QUINOLINIC | 0.0 | 0–6 |
| OROTIC ACID | 0.00 | 0–3 |
| D-AM LEVULINIC | 274.3 | 0–18 |
| 3-METHYL HISTIDINE | 0 | 0–75 |
| NIACINAMIDE | 0.0 | 0–1 |
| PSEUDOURIDINE | 8927 | 10–220 |
| 2-DEOXYTETRONIC | 0 | 0–75 |
| P-HO-PHEN-ACETIC | 9 | 0–12 |
| XANTHINE | 0 | 0–18 |
| UROCANIC ACID | 11 | 0–3 |
| ASCORBIC ACID | 0 | 0–160 |
| GLYCEROL | 470 | 0–9 |
| Neurotransmitters | | |
| GABA | 0.0 | 0–1 |
| HOMOVANILLIC ACID | 91.0 | 0–10 |
| NORMETANEPHRINE | 0.7 | 0–1 |
| VANILLYLMANDELIC | 0.4 | 0–6 |
| METANEPHRINE | 0.4 | 0–2 |
| 5-HIAA | 3.2 | 0–6 |
| MHPG | 0.0 | 0–1 |
| ETHANOLAMINE | 218 | 10–90 |
| Carbohydrates | | |
| THREITOL | 0 | 0–40 |
| ERYTHRITOL | 4 | 0–55 |
| ARABINOSE | 0 | 0–30 |
| FRUCTOSE | 0.0 | 0–12 |
| FUCOSE | 0.0 | 0–12 |
| RIBOSE | 0 | 0–70 |
| XYLOSE | 71 | 0–115 |
| GLUCOSE | 101 | 0–110 |
| GALACTOSE | 1 | 0–200 |
| MANNOSE | 36 | 0–70 |
| N-AC-GLUCOSAMINE | 0.9 | 0–3 |
| LACTOSE | 107 | 0–60 |
| MALTOSE | 61 | 0–40 |
| XYLITOL | 0.0 | 0–15 |
| ARABINITOL | 0.0 | 0–30 |
| RIBITOL | 0.0 | 0–10 |
| ALLOSE | 0.0 | 0–10 |
| GLUCURONIC ACID | 35.8 | 0–50 |
| GALACTONIC ACID | 10 | 0–60 |
| GLUCONIC ACID | 4.5 | 0–35 |
| GLUCARIC | 0.0 | 0–5 |
| MANNITOL | 12.7 | 0–15 |
| DULCITOL | 1.0 | 0–10 |
| SORBITOL | 12.7 | 0–10 |
| INOSITOL | 2.0 | 0–12 |
| SUCROSE | 577 | 0–75 |
| Amino Acids and Glycine Conjugates | | |
| PROPIONYL GLY | 0.0 | 0–1 |
| BUTYRYL GLYCINE | 0.0 | 0–1 |
| HEXANOL GLYCINE | 0.0 | 0–1 |
| PHENYL PROP GLY | 0.0 | 0–1 |
| SUBERYL GLYCINE | 0.0 | 0–1 |
| ISOVALERYL GLY | 279.7 | 0–1 |
| TIGLY GLY | 53.2 | 0–1 |
| BETA MET CROT GLY | 0.0 | 0–1 |
| GLYCINE | 584 | 0–500 |
| ALANINE | 437 | 0–130 |
| SARCOSINE | 5.2 | 0–8 |
| BETA-ALANINE | 0.0 | 0–2 |
| B-AMINOISOBUTYRIC | 2 | 0–50 |
| SERINE | 675 | 0–85 |
| PROLINE | 55.3 | 0–8 |
| HYDROXY PROLINE | 386 | 0–75 |
| HYDROXY LYSINE | 0.0 | 0–1 |
| ASPARTIC ACID | 96.5 | 0–2 |
| ASPARAGINE | 0.0 | 0–2 |
| N-AC ASPARTIC | 10.3 | 0–20 |
| ORNITHINE | 55.4 | 0–5 |
| GLUTAMIC ACID | 20.1 | 0–6 |
| GLUTAMINE | 0 | 0–210 |
| PIPECOLIC ACID | 0.0 | 0–1 |
| LEUCINE | 54.5 | 0–9 |
| KETO LEUCINE | 64.7 | 0–1 |
| VALINE | 112.8 | 0–18 |
| KETO-VALINE | 0.0 | 0–1 |
| ISOLEUCINE | 41.7 | 0–5 |
| KETO-ISOLEUCINE | 0.0 | 0–1 |
| LYSINE | 14 | 0–35 |
| HISTIDINE | 5 | 0–225 |
| THREONINE | 96 | 0–45 |
| HOMOSERINE | 0.0 | 0–1 |
| METHIONINE | 32.3 | 0–3 |
| CYSTEINE | 713 | 0–160 |
| HOMECYSTEINE | 0.0 | 0–1 |
| CYSTATHIONINE | 0.0 | 0–1 |
| HOMOCYSTINE | 0.0 | 0–1 |
| CYSTINE | 0.0 | 0–5 |
| PHENYLALANINE | 19 | 0–20 |
| TYROSINE | 23 | 0–22 |
| TRYPTOPHAN | 8 | 0–25 |

This sample contained 0.02 uMoles Creatinine/1.00 ml.

TABLE 26

METABOLIC SCREENING LABORATORY
URINE ORGANIC CONSTITUENTS
FRACTION VII, BEAR URINE
JZ4021
CONCENTRATION: THIS SAMPLE CONTAINED 0.02 mM CREATININE/mL

| PEAK | CONSTITUENT'S BEST MATCH FROM LIBRARY* | LIB ENTRY | FIT vs 1000 | AREA % | AREA OF CREAT |
|---|---|---|---|---|---|
| 8 | 10, STN031 | 1893 | 854 | 4.82 | 564.34 |
| 20 | 16, 011031 | 1989 | 819 | 6.98 | 817.58 |
| 35 | 35, JZ4011 | 2300 | 945 | 0.97 | 113.26 |
| 58 | 49, AK2011 | 2047 | 821 | 0.68 | 79.19 |
| 67 | SILANE, TRIMETHYLPHENOXY- | 1122 | 935 | 2.89 | 338.68 |
| 73 | 1,3 PROPANEDIOL DI-TMS | 1675 | 931 | 6.05 | 708.72 |
| 78 | LACTIC ACID DI-TMS | 1510 | 931 | 1.23 | 144.38 |
| 108 | 107, JZ4011 | 2301 | 889 | 0.78 | 91.61 |
| 118 | 104, NJ3031 | 2131 | 880 | 11.50 | 1346.76 |
| 122 | 119, JQ4011 | 2243 | 920 | 1.13 | 131.83 |
| 186 | BETA-LACTATE DI-TMS | 1654 | 769 | 2.12 | 248.66 |
| 190 | 2-METHYL 2-HYDROXY BUTYRIC ACID DI-TMS | 140 | 887 | 0.43 | 50.10 |
| 292 | UREA DI-TMS | 37 | 813 | 2.61 | 305.69 |
| 362 | TRIMETHYLSILYL ETHER OF GLYCEROL | 273 | 913 | 1.73 | 202.95 |
| 427 | METHYLSUCCINIC ACID DI-TMS | 173 | 943 | 1.52 | 178.04 |
| 501 | 501 | 0 | 0 | 1.45 | 170.19 |
| 697 | 697 | 0 | 0 | 1.05 | 123.17 |
| 750 | 697, JZ4021 | 2316 | 603 | 0.65 | 76.67 |
| 809 | METHYL D3 CREATININE TRI-TMS | 1466 | 683 | 26.41 | 3094.26 |
| 848 | 848 | 0 | 0 | 0.52 | 60.54 |
| 985 | 985 | 0 | 0 | 0.72 | 84.59 |
| 1239 | P-HYDROXYPHENYL LACTIC ACID TRI-TMS | 578 | 957 | 5.50 | 644.36 |
| 1496 | 1481, NU3091 | 2124 | 753 | 0.48 | 56.26 |
| 1596 | PSEUDO URIDINE PENTA-TMS | 1779 | 783 | 9.00 | 1054.48 |
| 1642 | 1631, M15041 | 1802 | 789 | 9.19 | 1076.96 |
| 1689 | 1689 | 0 | 0 | 0.58 | 67.59 |
| 1741 | TREHALOSE PER-TMS | 1850 | 773 | 2.86 | 335.16 |
| 1746 | SUCROSE OCTA-TMS | 1080 | 923 | 0.97 | 113.28 |

*The named compound matches the sample peak with a reliability given by "FIT"/1000.

Isolated compounds obtained from GCIMS were then compared to a database of chemical mass spectra for identification. Tables 21, 23, and 25 list the identified organic acids, nutritionals, carbohydrates, neurotransmitters, amino acids, and glycine conjugates of Fractions V, VI, and VII respectively.

Tables 22, 24, and 26 list peaks found in Fractions V, VI, and VII. The peaks are identified by retention time and correlated with the "best match" identified from the database library. Values of 700 or higher (1000 represents a perfect match) are considered indicative of substance identification. Peaks identified solely by a special number (peak #7 in Table 22 of Fraction V) indicate that this particular substance has been previously identified but that its chemical structure is unknown. When the peak number and the "best match from the library" are the same (as for peaks 878, 940, 1284, and 1594 in Table 22), it is an indication that these substances have not been identified by previous users of the database library. Similar data for Fractions I, II, IV, VIII, IX and X are in the following Tables 27 through 38.

BHB is found mainly in Fraction IV; MNC is found in Fractions V and VI. The most potent stimulators of osteoblast activity are found in Fractions V, VI, and VII.

Summary

1. Separation techniques of BDI have been refined. BDI has been separated into ten small fractions. Fractions V, VI, and VII of BDI contain substances that produce the most potent stimulation of osteoblasts. The substances that most strongly inhibit osteoblast function are found in Fraction III of BDI.
2. MNC is found in two fractions of BDI that produce the most potent stimulation of osteoblasts—Fractions V and Fraction VI. Preliminary data suggest that one or more components of MNC are found in Fraction VII.
3. The presence of known and unknown substances contained in all ten fractions has been recorded by GC/MS.

TABLE 27

QUANTIFIED TARGET PANEL
METABOLIC SCREENING LABORATORY
FRACTION I, BEAR URINE
JZ4041:3

| | uM/L* | Nrml Range |
|---|---|---|
| Organic Acids | | |
| LACTIC ACID | 283233 | |
| PYRUVIC ACID | 8387 | |
| GLYCOLIC ACID | 1032 | |
| ALPHA-OH-BUTYRIC | 19.5 | |
| OXALIC | 0.0 | |
| 4-OH-BUTYRIC | 0.0 | |
| HEXANOIC ACID | 227.5 | |
| 5-HYDROXYCAPROIC | 0.0 | |
| OCTANOIC | 0.0 | |
| BETA-LACTATE | 674.0 | |
| SUCCINIC ACID | 0 | |
| GLUTARIC ACID | 0.0 | |
| 2-OXO-GLUTARATE | 0.0 | |
| FUMARIC | 35.0 | |
| MALEIC | 0.0 | |
| MALIC ACID | 0.0 | |
| ADIPIC ACID | 49.5 | |
| SUBERIC ACID | 47.5 | |
| SEBACIC ACID | 0.0 | |
| GLYCERIC ACID | 0.0 | |

TABLE 27-continued

QUANTIFIED TARGET PANEL
METABOLIC SCREENING LABORATORY
FRACTION I, BEAR URINE
JZ4041:3

|  | uM/L* | Nrml Range |
|---|---|---|
| BETA-OH-BUTYRIC | 2075.5 | |
| METHYLSUCCINIC | 0.0 | |
| METHYLMALONIC | 0.0 | |
| ETHYLMALONI | 0.0 | |
| HOMOGENTISIC ACID | 0.0 | |
| PHENYLPYRUVIC ACID | 0.0 | |
| SUCCINYLACETONE | 0.0 | |
| 3-OH-ISOVALERIC | 0.0 | |
| PHOSPHATE | 3.71 | mg/dL |
| CITRIC ACID | 61 | |
| HIPPURIC ACID | 0 | |
| URIC ACID | 1.20 | mg/dL |
| Nutritionals | | |
| FORMIMINOGLUTAMIC | 0.00 | |
| 4-PYRIDOXIC ACID | 0.0 | |
| PANTOTHENIC ACID | 0.0 | |
| XANTHURENIC ACID | 0.0 | |
| KYNURENINE | 0.0 | |
| QUINOLINIC | 0.0 | |
| 7OROTIC ACID | 0.0 | |
| D-AM LEVULINIC | ******** | |
| 3-METHYL HISTIDINE | 0.00 | |
| NIACINAMIDE | 0.0 | |
| PSEUDOURIDINE | 221791 | |
| 2-DEOXYTETRONIC | 0 | |
| P-HO-PHEN-ACETIC | 10 | |
| XANTHINE | 0 | |
| UROCANIC ACID | 96 | |
| ASCORBIC ACID | 0 | |
| GLYCEROL | 5903.5 | |
| Carbohydrates | | |
| THREITOL | 0 | |
| ERYTHRITOL | 27 | |
| ARABINOSE | 0 | |
| FUCOSE | 0.0 | |
| RIBOSE | 0.0 | |
| XYLOSE | 13 | |
| FRUCTOSE | 1067 | |
| GLUCOSE | 35 | |
| mg/dLGALACTOSE | 104 | |
| MANNOSE | 988 | |
| N-AC-GLUCOSAMINE | 0.0 | |
| LACTOSE | 2921 | |
| MALTOSE | 2684 | |
| XYLITOL | 0.0 | |
| ARABINITOL | 0.0 | |
| RIBITOL | 0.0 | |
| ALLOSE | 0.0 | |
| GLUCURONIC ACID | 0.0 | |
| GALACTONIC ACID | 440 | |
| GLUCONIC ACID | 0.0 | |
| CLUCARIC | 0.0 | |
| MANNITOL | 681.5 | |
| DULCITOL | 91.0 | |
| SORBITOL | 681.0 | |
| INOSITOL | 107.0 | |
| SUCROSE | 12380 | |
| Neurotransmitters | | |
| GABA | 89.5 | |
| HOMOVANILLIC ACID | 0.0 | |
| NORMETANEPHRINE | 0.0 | |
| VANILLYLMANDELIC | 0.0 | |
| METANEPHRINE | 0.0 | |
| 5-HIAA | 0.0 | |
| MHPG | 0.0 | |
| ETHANOLAMINE | 4416 | |

TABLE 27-continued

QUANTIFIED TARGET PANEL
METABOLIC SCREENING LABORATORY
FRACTION I, BEAR URINE
JZ4041:3

|  | uM/L* | Nrml Range |
|---|---|---|
| Amino Acids and Glycine Conjugates | | |
| PROPIONYL GLY | 0.0 | |
| BUTYRYL GLYCINE | 0.0 | |
| HEXANOL GLYCINE | 0.0 | |
| PHENYL PROP GLY | 0.0 | |
| SUBERYL GLYCINE | 0.0 | |
| ISOVALERYL GLY | 0.0 | |
| TIGLY GLY | 0.0 | |
| BETA MET CROT GLY | 0.0 | |
| GLYCINE | 10411 | |
| ALANINE | 93 | |
| SARCOSINE | 108.0 | |
| BETA-ALANINE | 0.0 | |
| B-AMINOISOBUTYRIC | 0 | |
| SERINE | 10329 | |
| PROLINE | 1125.5 | |
| HYDROXY PROLINE | 10671 | |
| HYDROXY LYSINE | 0.0 | |
| ASPARTIC ACID | 1012.0 | |
| ASPARAGINE | 27.0 | |
| N-AC ASPARTIC | 116.0 | |
| ORNITHINE | 390.0 | |
| GLUTAMIC ACID | 343.5 | |
| GLUTAMINE | 0 | |
| PIPECOLIC ACID | 0.0 | |
| LEUCINE | 1342.0 | |
| KETO LEUCINE | 2776.0 | |
| VALINE | 2256.0 | |
| KETO-VALINE | 0.0 | |
| ISOLEUCINE | 985.0 | |
| KETO-ISOLEUCINE | 0.0 | |
| LYSINE | 63 | |
| HISTIDINE | 0 | |
| THREONINE | 771 | |
| HOMOSERINE | 0.0 | |
| METHIONINE | 0.0 | |
| CYSTEINE | 3314.5 | |
| HOMECYSTEINE | 0.0 | |
| CYSTATHIONINE | 0.0 | |
| HOMOCYSTINE | 0.0 | |
| CYSTINE | 0.0 | |
| PHENYLALANINE | 308.5 | |
| TYROSINE | 370 | |
| TRYPTOPHAN | 28.0 | |

This sample contained 7.61 mg Creatinine/dL.

TABLE 28

METABOLIC SCREENING LABORATORY
URINE ORGANIC CONSTITUENTS
FRACTION I, BEAR URINE
JZ4041
CONCENTRATION: THIS SAMPLE CONTAINED 0.00 uM CREATININE/mL

| PEAK | CONSTITUENT'S BEST MATCH FROM LIBRARY* | LIB ENTRY | FIT vs 1000 | AREA % | AREA % OF CREAT |
|---|---|---|---|---|---|
| 9 | 10, STN031 | 1893 | 849 | 12.44 | 50748.26 |
| 20 | 10, M13011 | 1782 | 755 | 12.97 | 52898.66 |
| 35 | 35, JZ4011 | 2300 | 942 | 1.24 | 5069.15 |
| 58 | 49, AK2011 | 2047 | 804 | 1.01 | 4129.25 |
| 67 | SILANE, TRIMETHYLPHENOXY- | 1122 | 934 | 3.83 | 15642.15 |
| 72 | ETHYL AMINE DI-TMS | 22 | 546 | 12.80 | 52202.81 |
| 79 | LACTIC ACID DI-TMS | 1510 | 959 | 7.49 | 30555.24 |
| 108 | 107, JZ4011 | 2301 | 939 | 0.99 | 4047.10 |
| 118 | 104, NJ3031 | 2131 | 882 | 16.86 | 68779.39 |
| 122 | 119, JQ4011 | 2243 | 930 | 1.60 | 6511.24 |
| 186 | BETA-LACTATE DI-TMS | 1654 | 770 | 2.91 | 11857.41 |
| 288 | UREA DI-TMS | 37 | 816 | 0.90 | 3654.45 |
| 361 | TRIMETHYLSILYL ETHER OF GLYCEROL | 273 | 911 | 1.17 | 4787.66 |
| 539 | 539 | 0 | 0 | 0.65 | 2647.54 |
| 807 | METHYL D3 CREATININE TRI-TMS | 1466 | 706 | 18.22 | 74308.42 |
| 1370 | PALMITIC ACID TMS | 335 | 857 | 0.92 | 3734.21 |
| 1519 | STEARIC ACID TMS | 434 | 870 | 0.70 | 2849.90 |
| 1595 | PSEUDO URIDINE PENTA-TMS | 1779 | 750 | 13.13 | 53567.98 |
| 1672 | 1669, P17031 | 1984 | 908 | 1.15 | 4703.70 |
| 1745 | SUCROSE OCTA-TMS | 1080 | 912 | 1.46 | 5942.59 |

*The named compound matches the sample peak with a reliability given by "FIT"/1000.

TABLE 29

QUANTIFIED TARGET PANEL
URINE ORGANIC COMPOUNDS
FRACTION II, BEAR URINE
JZ4051:4

| | mM/M CREATININE | Nrml Range |
|---|---|---|
| Organic Acids | | |
| LACTIC ACID | 94 | 0–75 |
| PYRUVIC ACID | 6 | 0–20 |
| GLYCOLIC ACID | 2 | 0–50 |
| ALPHA-OH-BUTYRIC | 0.1 | 0–1 |
| OXALIC | 0.0 | 0–25 |
| 4-OH-BUTYRIC | 0.0 | 0–1 |
| HEXANOIC ACID | 0.0 | 0–11 |
| 5-HYDROXYCAPROIC | 0.0 | 0–1 |
| OCTANOIC | 0.0 | 0–1 |
| BETA-LACTATE | 0.0 | 0–8 |
| SUCCINIC ACID | 3 | 0–20 |
| GLUTARIC ACID | 0.0 | 0–2 |
| 2-OXO-GLUTARATE | 0 | 0–210 |
| FUMARIC | 0.0 | 0–5 |
| MALEIC | 0.0 | 0 |
| MALIC ACID | 0.0 | 0–2 |
| ADIPIC ACID | 0.0 | 0–7 |
| SUBERIC ACID | 0.0 | 0–11 |
| SEBACIC ACID | 0.0 | 0–2 |
| GLYCERIC ACID | 0 | 0–4 |
| BETA-OH-BUTYRIC | 1 | 0–3 |
| METHYLSUCCINIC | 0.0 | 0 |
| METHYLMALONIC | 0 | 0–5 |
| ETHYLMALONI | 0.0 | 0–4 |
| HOMOGENTISIC ACID | 0.0 | 0–1 |
| PHENYLPYRUVIC ACID | 0.7 | 0–1 |
| SUCCINYLACETONE | 0.0 | 0–1 |
| 3-OH-ISOVALERIC | 0.0 | 0–21 |
| PHOSPHATE | 137 | 0–3000 |
| CITRIC ACID | 0 | 0–450 |
| HIPPURIC ACID | 13 | 0–2000 |
| URIC ACID | 0 | 0–360 |

TABLE 29-continued

QUANTIFIED TARGET PANEL
URINE ORGANIC COMPOUNDS
FRACTION II, BEAR URINE
JZ4051:4

| | mM/M CREATININE | Nrml Range |
|---|---|---|
| Nutritionals | | |
| KYNURENIC ACID | 0.0 | |
| FORMIMINOGLUTAMIC | 0.00 | 0–3 |
| 4-PYRIDOXIC ACID | 0.0 | 0–9 |
| PANTOTHENIC ACID | 0 | 0–30 |
| XANTHURENIC ACID | 0.0 | 0–1 |
| KYNURENINE | 0.0 | 0–1 |
| QUINOLINIC | 0.0 | 0–6 |
| OROTIC ACID | 0.00 | 0–3 |
| D-AM LEVULINIC | 1.0 | 0–18 |
| 3-METHYL HISTIDINE | 7 | 0–75 |
| NIACINAMIDE | 0.0 | 0–1 |
| PSEUDOURIDINE | 170 | 10–220 |
| 2-DEOXYTETRONIC | 0 | 0–75 |
| P-HO-PHEN-ACETIC | 5 | 0–12 |
| XANTHINE | 0 | 0–18 |
| UROCANIC ACID | 0 | 0–3 |
| ASCORBIC ACID | 0 | 0–160 |
| GLYCEROL | 3 | 0–9 |
| Carbohydrates | | |
| THREITOL | 1 | 0–40 |
| ERYTHRITOL | 5 | 0–55 |
| ARABINOSE | 0 | 0–30 |
| FUCOSE | 0.0 | 0–12 |
| RIBOSE | 0.0 | 0–12 |
| XYLOSE | 0 | 0–70 |
| FRUCTOSE | 0 | 0–115 |
| GLUCOSE | 2 | 0–110 |
| GALACTOSE | 0 | 0–200 |
| MANNOSE | 0 | 0–70 |
| N-AC-GLUCOSAMINE | 0.0 | 0–3 |
| LACTOSE | 1 | 0–60 |

TABLE 29-continued

QUANTIFIED TARGET PANEL
URINE ORGANIC COMPOUNDS
FRACTION II, BEAR URINE
JZ4051:4

| | mM/M CREATININE | Nrml Range |
|---|---|---|
| MALTOSE | 1 | 0–40 |
| XYLITOL | 0.9 | 0–15 |
| ARABINITOL | 0.0 | 0–30 |
| RIBITOL | 0.0 | 0–10 |
| ALLOSE | 0.4 | 0–10 |
| GLUCURONIC ACID | 0.0 | 0–50 |
| GALACTONIC ACID | 0 | 0–60 |
| GLUCONIC ACID | 0.0 | 0–35 |
| CLUCARIC | 0.0 | 0–5 |
| MANNITOL | 0.1 | 0–15 |
| DULCITOL | 0.1 | 0–10 |
| SORBITOL | 0.9 | 0–10 |
| INOSITOL | 0.1 | 0–12 |
| SUCROSE | 4 | 0–75 |
| Neurotransmitters | | |
| GABA | 0.0 | 0–1 |
| HOMOVANILLIC ACID | 1.1 | 0–10 |
| NORMETANEPHRINE | 0.0 | 0–1 |
| VANILLYLMANDELIC | 0.0 | 0–6 |
| METANEPHRINE | 0.2 | 0–2 |
| 5-HIAA | 1.9 | 0–6 |
| MHPG | 0.0 | 0–1 |
| ETHANOLAMINE | 6 | 10–90 |
| Amino Acids and Glycine Conjugates | | |
| PROPIONYL GLY | 0.0 | 0–1 |
| BUTYRYL GLYCINE | 0.0 | 0–1 |
| HEXANOL GLYCINE | 0.0 | 0–1 |
| PHENYL PROP GLY | 0.0 | 0–1 |
| SUBERYL GLYCINE | 0.0 | 0–1 |
| ISOVALERYL GLY | 0.0 | 0–1 |
| TIGLY GLY | 0.0 | 0–1 |
| BETA MET CROT GLY | 0.0 | 0–1 |
| GLYCINE | 10 | 0–500 |
| ALANINE | 0 | 0–130 |
| SARCOSINE | 0.2 | 0–8 |
| BETA-ALANINE | 0.0 | 0–2 |
| B-AMINOISOBUTYRIC | 0 | 0–50 |
| SERINE | 9 | 0–85 |
| PROLINE | 0.7 | 0–8 |
| HYDROXY PROLINE | 13 | 0–75 |
| HYDROXY LYSINE | 0.0 | 0–1 |
| ASPARTIC ACID | 0.6 | 0–2 |
| ASPARAGINE | 0.0 | 0–2 |
| N-AC ASPARTIC | 0.0 | 0–20 |
| ORNITHINE | 0.1 | 0–5 |
| GLUTAMIC ACID | 0.5 | 0–6 |
| GLUTAMINE | 0 | 0–210 |
| PIPECOLIC ACID | 0.0 | 0–1 |
| LEUCINE | 0.9 | 0–9 |
| KETO LEUCINE | 13.4 | 0–1 |
| VALINE | 1.6 | 0–18 |
| KETO-VALINE | 0.0 | 0–1 |
| ISOLEUCINE | 0.5 | 0–5 |
| KETO-ISOLEUCINE | 0.0 | 0–1 |
| LYSINE | 4 | 0–35 |
| HISTIDINE | 0 | 0–225 |
| THREONINE | 0 | 0–45 |
| HOMOSERINE | 0.0 | 0–1 |
| METHIONINE | 0.0 | 0–3 |
| CYSTEINE | 9 | 0–160 |
| HOMOCYSTEINE | 0.0 | 0–1 |
| CYSTATHIONINE | 0.0 | 0–1 |
| HOMOCYSTINE | 0.0 | 0–1 |
| CYSTINE | 0.0 | 0–5 |
| PHENYLALANINE | 0 | 0–20 |
| TYROSINE | 0 | 0–22 |
| TRYPTOPHAN | 0 | 0–25 |

This sample contained 0.42 uMoles Creatinine/1.00 ml.

TABLE 30

METABOLIC SCREENING LABORATORY
URINE ORGANIC CONSTITUENTS
FRACTION II, BEAR URINE
JZ4051
CONCENTRATION: THIS SAMPLE CONTAINED 0.42 uM CREATININE/mL

| PEAK | CONSTITUENT'S BEST MATCH FROM LIBRARY* | LIB ENTRY | FIT vs 1000 | AREA % | AREA % OF CREAT |
|---|---|---|---|---|---|
| 6 | 10, STN031 | 1893 | 823 | 2.11 | 13.22 |
| 13 | 13 | 0 | 0 | 0.53 | 3.32 |
| 18 | 16, O11031 | 1989 | 785 | 6.94 | 43.44 |
| 33 | 35, JZ4011 | 2300 | 882 | 0.59 | 3.70 |
| 56 | 49, AK2011 | 2047 | 831 | 0.51 | 3.19 |
| 65 | SILANE, TRIMETHYLPHENOXY- | 1122 | 935 | 1.87 | 11.73 |
| 69 | ETHYL AMINE DI-TMS | 22 | 581 | 5.56 | 34.84 |
| 76 | LACTIC ACID DI-TMS | 1510 | 946 | 1.02 | 6.42 |
| 106 | 107, JZ4011 | 2301 | 785 | 0.58 | 3.62 |
| 116 | 104, NJ3031 | 2131 | 866 | 9.15 | 57.29 |
| 120 | 119, JQ4011 | 2243 | 913 | 0.75 | 4.71 |
| 184 | BETA-LACTATE DI-TMS | 1654 | 764 | 1.45 | 9.07 |
| 250 | 251, JZ4011 | 2302 | 923 | 0.47 | 2.97 |
| 282 | UREA DI-TMS | 37 | 721 | 0.83 | 5.23 |
| 308 | 283 NF3091 | 2093 | 745 | 18.17 | 113.79 |
| 354 | PHOSPHATE TRI-TMS | 1413 | 905 | 3.37 | 21.13 |
| 537 | 539 JZ4041 | 2320 | 956 | 0.56 | 3.53 |
| 810 | CREATININE TRI-TMS | 1784 | 946 | 35.05 | 219.48 |
| 846 | 3-PHENYL LACTIC TMS 2 | 1562 | 677 | 0.43 | 2.70 |
| 916 | PARA-HYDROXYPHENYLACETIC ACID DI-TMS | 1485 | 938 | 0.64 | 3.99 |

TABLE 30-continued

METABOLIC SCREENING LABORATORY
URINE ORGANIC CONSTITUENTS
FRACTION II, BEAR URINE
JZ4051
CONCENTRATION: THIS SAMPLE CONTAINED 0.42 uM CREATININE/mL

| PEAK | CONSTITUENT'S BEST MATCH FROM LIBRARY* | LIB ENTRY | FIT vs 1000 | AREA % | AREA % OF CREAT |
|---|---|---|---|---|---|
| 1189 | 1189 | 0 | 0 | 0.59 | 3.70 |
| 1204 | 1189, NU3061 | 2118 | 711 | 1.81 | 11.34 |
| 1230 | MOUSE HORMONE? | 1508 | 712 | 0.39 | 2.44 |
| 1234 | 1234, JD2031 | 2002 | 789 | 0.85 | 5.32 |
| 1261 | STEROID M | 1509 | 788 | 0.73 | 4.60 |
| 1369 | PALMITIC ACID TMS | 335 | 862 | 1.00 | 6.25 |
| 1519 | STEARIC ACID TMS | 434 | 918 | 0.38 | 2.38 |
| 1594 | PSEUDO URIDINE PENTA-TMS | 1779 | 816 | 5.75 | 36.03 |

*The named compound matches the sample peak with a reliability given by "FIT"/1000.

TABLE 31

QUANTIFIED TARGET PANEL
URINE ORGANIC COMPOUNDS
FRACTION IV, BEAR URINE
JZ4071:6

| | mM/M CREATININE | Nrml Range |
|---|---|---|
| Organic Acids | | |
| LACTIC ACID | 2393 | 0–75 |
| PYRUVIC ACID | 15 | 0–20 |
| GLYCOLIC ACID | 4 | 0–50 |
| ALPHA-OH-BUTYRIC | 0.7 | 0–1 |
| OXALIC | 0.0 | 0–25 |
| 4-OH-BUTYRIC | 0.0 | 0–1 |
| HEXANOIC ACID | 28.1 | 0–11 |
| 5-HYDROXYCAPROIC | 0.0 | 0–1 |
| OCTANOIC | 0.0 | 0–1 |
| BETA-LACTATE | 19.9 | 0–8 |
| SUCCINIC ACID | 1916 | 0–20 |
| GLUTARIC ACID | 0.0 | 0–2 |
| 2-OXO-GLUTARATE | 210 | 0–210 |
| FUMARIC | 1.7 | 0–5 |
| MALEIC | 25.6 | 0 |
| MALIC ACID | 39.4 | 0–2 |
| ADIPIC ACID | 0.9 | 0–7 |
| SUBERIC ACID | 0.2 | 0–11 |
| SEBACIC ACID | 1.6 | 0–2 |
| GLYCERIC ACID | 0 | 0–4 |
| BETA-OH-BUTYRIC | 5822 | 0–3 |
| METHYLSUCCINIC | 0.0 | 0 |
| METHYLMALONIC | 0 | 0–5 |
| ETHYLMALONIC | 0.0 | 0–4 |
| HOMOGENTISIC ACID | 0.0 | 0–1 |
| PHENYLPYRUVIC ACID | 1163.4 | 0–1 |
| SUCCINYLACETONE | 1.0 | 0–1 |
| 3-OH-ISOVALERIC | 2.1 | 0–21 |
| PHOSPHATE | 135 | 0–3000 |
| CITRIC ACID | 8 | 0–450 |
| HIPPURIC ACID | 25 | 0–2000 |
| URIC ACID | 2 | 0–360 |
| Nutritionals | | |
| KYNURENIC ACID | 13.8 | |
| FORMIMINOGLUTAMIC | 16.80 | 0–3 |
| 4-PYRIDOXIC ACID | 60.5 | 0–9 |
| PANTOTHENIC ACID | 20 | 0–30 |
| XANTHURENIC ACID | 0.0 | 0–1 |
| KYNURENINE | 3.2 | 0–1 |
| QUINOLINIC | 37.4 | 0–6 |
| OROTIC ACID | 0.00 | 0–3 |
| D-AM LEVULINIC | 30.8 | 0–18 |
| 3-METHYL HISTIDINE | 9 | 0–75 |
| NIACINAMIDE | 12.7 | 0–1 |
| PSEUDOURIDINE | 19 | 10–220 |
| 2-DEOXYTETRONIC | 2 | 0–75 |
| P-HO-PHEN-ACETIC | 2 | 0–12 |
| XANTHINE | 0 | 0–18 |
| UROCANIC ACID | 1 | 0–3 |
| ASCORBIC ACID | 3 | 0–160 |
| GLYCEROL | 36 | 0–9 |
| Carbohydrates | | |
| THREITOL | 0 | 0–40 |
| ERYTHRITOL | 2 | 0–55 |
| ARABINOSE | 0 | 0–30 |
| FUCOSE | 1.4 | 0–12 |
| RIBOSE | 1.0 | 0–12 |
| XYLOSE | 2 | 0–70 |
| FRUCTOSE | 0 | 0–115 |
| GLUCOSE | 55 | 0–110 |
| GALACTOSE | 7 | 0–200 |
| MANNOSE | 1 | 0–70 |
| N-AC-GLUCOSAMINE | 0.3 | 0–3 |
| LACTOSE | 11 | 0–60 |
| MALTOSE | 11 | 0–40 |
| XYLITOL | 0.0 | 0–15 |
| ARABINITOL | 0.0 | 0–30 |
| RIBITOL | 0.0 | 0–10 |
| ALLOSE | 0.8 | 0–10 |
| GLUCURONIC ACID | 11.8 | 0–50 |
| GALACTONIC ACID | 166 | 0–60 |
| GLUCONIC ACID | 0.0 | 0–35 |
| CLUCARIC | 0.0 | 0–5 |
| MANNITOL | 1.2 | 0–15 |
| DULCITOL | 0.0 | 0–10 |
| SORBITOL | 1.2 | 0–10 |
| INOSITOL | 0.0 | 0–12 |
| SUCROSE | 14 | 0–75 |
| Neurotransmitters | | |
| GABA | 4.2 | 0–1 |
| HOMOVANILLIC ACID | 2.0 | 0–10 |
| NORMETANEPHRINE | 20.2 | 0–1 |
| VANILLYLMANDELIC | 2.0 | 0–6 |
| METANEPHRINE | 0.5 | 0–2 |
| 5-HIAA | 5.0 | 0–6 |
| MHPG | 2.7 | 0–1 |
| ETHANOLAMINE | 17 | 10–90 |

TABLE 31-continued

QUANTIFIED TARGET PANEL
URINE ORGANIC COMPOUNDS
FRACTION IV, BEAR URINE
JZ4071:6

| | mM/M CREATININE | Nrml Range |
|---|---|---|
| Amino Acids and Glycine Conjugates | | |
| PROPIONYL GLY | 322.6 | 0–1 |
| BUTYRYL GLYCINE | 0.4 | 0–1 |
| HEXANOYL GLYCINE | 0.0 | 0–1 |
| PHENYL PROP GLY | 0.0 | 0–1 |
| SUBERYL GLYCINE | 0.0 | 0–1 |
| ISOVALERYL GLY | 35.7 | 0–1 |
| TIGLY GLY | 18.7 | 0–1 |
| BETA MET CROT GLY | 150.5 | 0–1 |
| GLYCINE | 82 | 0–500 |
| ALANINE | 50 | 0–130 |
| SARCOSINE | 0.3 | 0–8 |
| BETA-ALANINE | 0.0 | 0–2 |
| B-AMINOISOBUTYRIC | 39 | 0–50 |
| SERINE | 54 | 0–85 |
| PROLINE | 4.8 | 0–8 |
| HYDROXY PROLINE | 92 | 0–75 |
| HYDROXY LYSINE | 0.0 | 0–1 |
| ASPARTIC ACID | 14.0 | 0–2 |
| ASPARAGINE | 0.3 | 0–2 |
| N-AC ASPARTIC | 5.0 | 0–20 |
| ORNITHINE | 12.0 | 0–5 |
| GLUTAMIC ACID | 2.4 | 0–6 |
| GLUTAMINE | 46 | 0–210 |
| PIPECOLIC ACID | 0.0 | 0–1 |
| LEUCINE | 47.4 | 0–9 |
| KETO LEUCINE | 45.3 | 0–1 |
| VALINE | 9.1 | 0–18 |
| KETO-VALINE | 0.0 | 0–1 |
| ISOLEUCINE | 6.3 | 0–5 |
| KETO-ISOLEUCINE | 0.0 | 0–1 |
| LYSINE | 45 | 0–35 |
| HISTIDINE | 9 | 0–225 |
| THREONINE | 6 | 0–45 |
| HOMOSERINE | 2.2 | 0–1 |
| METHIONINE | 0.0 | 0–3 |
| CYSTEINE | 179 | 0–160 |
| HOMECYSTEINE | 0.0 | 0–1 |
| CYSTATHIONINE | 1.2 | 0–1 |
| HOMOCYSTINE | 0.0 | 0–1 |
| CYSTINE | 0.3 | 0–5 |
| PHENYLALANINE | 3 | 0–20 |
| TYROSINE | 5 | 0–22 |
| TRYPTOPHAN | 238 | 0–25 |

This sample contained 0.42 uMoles Creatine/1.00 ml.

TABLE 32

METABOLIC SCREENING LABORATORY
URINE ORGANIC CONSTITUENTS
FRACTION IV, BEAR URINE
JZ4071
CONCENTRATION: THIS SAMPLE CONTAINED 0.23 uM CREATININE/mL

| PEAK | CONSTITUENT'S BEST MATCH FROM LIBRARY* | LIB ENTRY | FIT vs 1000 | AREA % | AREA % OF CREAT |
|---|---|---|---|---|---|
| 20 | 10, M13011 | 1782 | 716 | 1.28 | 48.98 |
| 28 | 10, M13011 | 1782 | 821 | 1.18 | 45.14 |
| 34 | 35, JZ4011 | 2300 | 836 | 0.25 | 9.56 |
| 57 | 49, AK2011 | 2047 | 814 | 0.20 | 7.79 |
| 66 | SILANE, TRIMETHYLPHENOXY- | 1122 | 879 | 0.80 | 30.66 |
| 71 | ETHYL AMINE DI-TMS | 22 | 529 | 2.92 | 111.91 |
| 78 | LACTIC ACID DI-TMS | 1510 | 927 | 4.23 | 162.24 |
| 107 | 107, JZ4011 | 2301 | 865 | 0.25 | 9.47 |
| 117 | 104, NJ3031 | 2131 | 872 | 4.13 | 158.52 |
| 122 | 119, JQ4011 | 2243 | 902 | 0.34 | 13.19 |
| 187 | BETA HYDROXYBUTYRIC ACID DI-TMS | 1622 | 930 | 14.85 | 569.62 |
| 251 | 251, JZ4011 | 2302 | 928 | 0.29 | 10.98 |
| 283 | 4-HYDROXY BUTYRIC ACID DI-TMS | 97 | 724 | 0.16 | 6.05 |
| 293 | 283, NF3091 | 2093 | 745 | 0.25 | 9.61 |
| 305 | 283, NF3091 | 2093 | 744 | 1.83 | 70.32 |

TABLE 32-continued

METABOLIC SCREENING LABORATORY
URINE ORGANIC CONSTITUENTS
FRACTION IV, BEAR URINE
JZ4071
CONCENTRATION: THIS SAMPLE CONTAINED 0.23 uM CREATININE/mL

| PEAK | CONSTITUENT'S BEST MATCH FROM LIBRARY* | LIB ENTRY | FIT vs 1000 | AREA % | AREA % OF CREAT |
|---|---|---|---|---|---|
| 355 | PHOSPHATE TRI-TMS | 1413 | 898 | 0.43 | 16.33 |
| 361 | TRIMETHYLSILYL ETHER OF GLYCEROL | 273 | 882 | 0.63 | 24.21 |
| 407 | SUCCINIC ACID DI-TMS | 1635 | 892 | 5.26 | 201.56 |
| 599 | PROPIONATE GLYCINE CONJUGATE DI-TMS | 165 | 961 | 1.11 | 42.71 |
| 611 | 564, JJ4021 | 2200 | 742 | 0.28 | 10.77 |
| 689 | CITRAMALIC ACID TRI-TMS, 675 | 2103 | 944 | 0.40 | 15.18 |
| 722 | NORLEUCINE DI-TMS | 1540 | 656 | 2.48 | 95.07 |
| 749 | 749 | 0 | 0 | 1.11 | 42.72 |
| 797 | 259, 192 TMS | 1470 | 367 | 0.27 | 10.23 |
| 808 | CREATININE, TRI-TMS | 1784 | 913 | 8.32 | 319.11 |
| 845 | 845 | 0 | 0 | 0.19 | 7.28 |
| 862 | 862 | 0 | 0 | 0.18 | 6.77 |
| 940 | GLYCOLIC ACID DI-TMS | 55 | 405 | 0.35 | 13.32 |
| 978 | 251, JZ4011 | 2302 | 390 | 0.16 | 6.22 |
| 985 | 985 | 0 | 0 | 2.58 | 98.95 |
| 997 | 996, G11021 | 1958 | 790 | 0.24 | 9.35 |
| 1000 | 1000 | 0 | 0 | 0.25 | 9.60 |
| 1011 | .BETA. PHENYLPYRUVIC ACID DI-TMS | 280 | 887 | 3.95 | 151.29 |
| 1027 | 1027 | 0 | 0 | 0.93 | 35.63 |
| 1037 | 1037 | 0 | 0 | 0.41 | 15.72 |
| 1047 | 1047 | 0 | 0 | 0.19 | 7.19 |
| 1064 | 2-HYDROXY BENZAMIDE DI-TMS | 198 | 421 | 0.51 | 19.63 |
| 1071 | 1071 | 0 | 0 | 0.22 | 8.29 |
| 1079 | CIS-ACONITIC ACID TRI-TMS | 540 | 792 | 6.66 | 255.42 |
| 1093 | L-GLUTAMIC ACID, N-ACETYL-N-TMS, BIS-TMS EST | 587 | 665 | 0.25 | 9.43 |
| 1098 | 862, JZ4071 | 2344 | 665 | 0.43 | 16.53 |
| 1103 | 1103 | 0 | 0 | 0.52 | 19.81 |
| 1114 | 1114 | 0 | 0 | 0.31 | 12.01 |
| 1120 | 1071, JZ4071 | 2350 | 685 | 0.64 | 24.48 |
| 1135 | 1135, JZ4011 | 2306 | 868 | 0.57 | 22.01 |
| 1178 | 1178 | 0 | 0 | 0.16 | 6.31 |
| 1183 | 6-AMINO HEXANOIC ACID DI-TMS | 166 | 537 | 0.41 | 15.79 |
| 1196 | QUINOLINIC TMS 2 | 1564 | 481 | 1.31 | 50.20 |
| 1202 | 1202 | 0 | 0 | 0.55 | 21.09 |
| 1228 | 1228 | 0 | 0 | 4.38 | 167.97 |
| 1237 | 1,6 DIHYDRO 1-METHYL 6-OXO 3-PYRIDINECARBOXAM | 63 | 558 | 4.31 | 165.39 |
| 1253 | MANNOSE PENTA-TMS | 879 | 901 | 0.28 | 10.68 |
| 1277 | 4-PYRIDOXIC ACID TRI-TMS | 580 | 697 | 0.37 | 14.00 |
| 1294 | NORVALINE DI-TMS | 128 | 402 | 0.75 | 28.82 |
| 1300 | 1300 | 0 | 0 | 0.39 | 14.89 |
| 1310 | NORVALINE DI-TMS | 128 | 432 | 0.25 | 9.50 |
| 1346 | P-HO PHENYL GLYCOLIC TRI-TMS | 532 | 735 | 0.17 | 6.61 |
| 1354 | MANNOSE PENTA-TMS | 879 | 913 | 0.38 | 14.67 |
| 1382 | 1382 | 0 | 0 | 0.64 | 24.60 |
| 1386 | GLYCINE DI-TMS | 51 | 477 | 0.18 | 6.93 |
| 1397 | 1217, NC1031 | 1992 | 543 | 0.16 | 6.32 |
| 1435 | 1435 | 0 | 0 | 0.20 | 7.49 |
| 1443 | URIC ACID TETRA-TMS | 1505 | 674 | 0.33 | 12.63 |
| 1510 | TRYPTOPHAN TRI-TMS | 1965 | 825 | 2.01 | 77.00 |
| 1515 | 1515 | 0 | 0 | 0.99 | 37.86 |
| 1545 | 1545 | 0 | 0 | 0.17 | 6.59 |
| 1589 | 1-PHENYL 2-AMINO PROPANE DI-TMS | 190 | 712 | 0.16 | 5.96 |
| 1595 | PSEUSO URIDINE PENTA-TMS | 1779 | 945 | 2.48 | 95.21 |
| 1604 | 1631, M15041 | 1802 | 692 | 1.73 | 66.36 |
| 1616 | 1616 | 0 | 0 | 0.47 | 17.85 |
| 1631 | 2-PROPENOIC ACID, 2-TMS-OXY-3-1-TMS-1H-IND | 618 | 766 | 1.21 | 46.30 |
| 1641 | 1624, NU3061 | 2120 | 696 | 2.78 | 106.59 |
| 1659 | 1659 | 0 | 0 | 0.60 | 23.09 |
| 1665 | 1665 | 0 | 0 | 0.26 | 10.03 |
| 1731 | TREHALOSE PER-TMS | 1850 | 685 | 0.25 | 9.50 |
| 1745 | TREHALOSE PER-TMS | 1850 | 788 | 0.17 | 6.63 |

*The named compound matches the sample peak with a reliability given by "FIT"/1000.

TABLE 33

QUANTIFIED TARGET PANEL URINE ORGANIC COMPOUNDS FRACTION VIII, BEAR URINE JZ4091:8

| | mM/M CREATININE | Nrml Range |
|---|---|---|
| Organic Acids | | |
| LACTIC ACID | 38661 | 0–75 |
| PYRUVIC ACID | 0 | 0–20 |
| GLYCOLIC ACID | 0 | 0–50 |
| ALPHA-OH-BUTYRIC | 0.0 | 0–1 |
| OXALIC | 0.0 | 0–25 |
| 4-OH-BUTYRIC | 0.0 | 0–1 |
| HEXANOIC ACID | 0.0 | 0–11 |
| 5-HYDROXYCAPROIC | 0.0 | 0–1 |
| OCTANOIC | 0.0 | 0–1 |
| BETA-LACTATE | 0.0 | 0–8 |
| SUCCINIC ACID | 0 | 0–20 |
| GLUTARIC ACID | 0.0 | 0–2 |
| 2-OXO-GLUTARATE | 0 | 0–210 |
| FUMARIC | 0.0 | 0–5 |
| MALEIC | 0.0 | 0 |
| MALIC ACID | 0.0 | 0–2 |
| ADIPIC ACID | 3878.3 | 0–7 |
| SUBERIC ACID | 0.0 | 0–11 |
| SEBACIC ACID | 244.7 | 0–2 |
| GLYCERIC ACID | 0 | 0–4 |
| BETA-OH-BUTYRIC | 89 | 0–3 |
| METHYLSUCCINIC | 0.0 | 0 |
| METHYLMALONIC | 0 | 0–5 |
| ETHYLMALONIC | ******** | 0–4 |
| HOMOGENTISIC ACID | 0.0 | 0–1 |
| PHENYLPYRUVIC ACID | 0.0 | 0–1 |
| SUCCINYLACETONE | 0.0 | 0–1 |
| 3-OH-ISOVALERIC | 0.0 | 0–21 |
| PHOSPHATE | 317 | 0–3000 |
| CITRIC ACID | 37 | 0–450 |
| HIPPURIC ACID | 84990 | 0–2000 |
| URIC ACID | 125 | 0–360 |
| Nutritionals | | |
| KYNURENIC ACID | 7544.8 | |
| FORMIMINOGLUTAMIC | 0.00 | 0–3 |
| 4-PYRIDOXIC ACID | 0.0 | 0–9 |
| PANTOTHENIC ACID | 0 | 0–30 |
| XANTHURENIC ACID | 0.0 | 0–1 |
| KYNURENINE | 0.0 | 0–1 |
| QUINOLINIC | 0.0 | 0–6 |
| OROTIC ACID | 0.00 | 0–3 |
| D-AM LEVULINIC | 0.0 | 0–18 |
| 3-METHYL HISTIDINE | 0 | 0–75 |
| NIACINAMIDE | 0.0 | 0–1 |
| PSEUDOURIDINE | 7176 | 10–220 |
| 2-DEOXYTETRONIC | 0 | 0–75 |
| P-HO-PHEN-ACETIC | 1019 | 0–12 |
| XANTHINE | 0 | 0–18 |
| UROCANIC ACID | 907 | 0–3 |
| ASCORBIC ACID | 0 | 0–160 |
| GLYCEROL | 8524 | 0–9 |
| Neurotransmitters | | |
| GABA | 0.0 | 0–1 |
| HOMOVANILLIC ACID | 4038.8 | 0–10 |
| NORMETANEPHRINE | 0.0 | 0–1 |
| VANILLYLMANDELIC | 0.0 | 0–6 |
| METANEPHRINE | 374.2 | 0–2 |
| 5-HIAA | 6190.5 | 0–6 |
| MHPG | 0.0 | 0–1 |
| ETHANOLAMINE | 3152 | 10–90 |
| Carbohydrates | | |
| THREITOL | 0 | 0–40 |
| ERYTHRITOL | 0 | 0–55 |
| ARABINOSE | 0 | 0–30 |
| FUCOSE | 0.0 | 0–12 |
| RIBOSE | 0.0 | 0–12 |
| XYLOSE | 0 | 0–70 |
| FRUCTOSE | 3266 | 0–115 |
| GLUCOSE | 4435 | 0–110 |
| GALACTOSE | 5127 | 0–200 |
| MANNOSE | 2585 | 0–70 |
| N-AC-GLUCOSAMINE | 11.8 | 0–3 |
| LACTOSE | 4679 | 0–60 |
| MALTOSE | 4470 | 0–40 |
| XYLITOL | 0.0 | 0–15 |
| ARABINITOL | 0.0 | 0–30 |
| RIBITOL | 0.0 | 0–10 |
| ALLOSE | 384.7 | 0–10 |
| GLUCURONIC ACID | 0.0 | 0–50 |
| GALACTONIC ACID | 13137 | 0–60 |
| GLUCONIC ACID | 0.0 | 0–35 |
| GLUCARIC | 42.7 | 0–5 |
| MANNITOL | 604.1 | 0–15 |
| DULCITOL | 0.0 | 0–10 |
| SORBITOL | 603.4 | 0–10 |
| INOSITOL | 0.0 | 0–12 |
| SUCROSE | 18255 | 0–75 |
| Amino Acids and Glycine Conjugates | | |
| PROPIONYL GLY | 0.0 | 0–1 |
| BUTYRYL GLYCINE | 2523.4 | 0–1 |
| HEXANOL GLYCINE | 0.0 | 0–1 |
| PHENYL PROP GLY | 0.0 | 0–1 |
| SUBERYL GLYCINE | 0.0 | 0–1 |
| ISOVALERYL GLY | ******** | 0–1 |
| TIGLY GLY | 0.0 | 0–1 |
| BETA MET CROT GLY | ******** | 0–1 |
| GLYCINE | 9496 | 0–500 |
| ALANINE | 7063 | 0–130 |
| SARCOSINE | 80.5 | 0–8 |
| BETA-ALANINE | 0.0 | 0–2 |
| B-AMINOISOBUTYRIC | 525 | 0–50 |
| SERINE | 10517 | 0–85 |
| PROLINE | 917.5 | 0–8 |
| HYDROXY PROLINE | 12808 | 0–75 |
| HYDROXY LYSINE | 1407.6 | 0–1 |
| ASPARTIC ACID | 1866.1 | 0–2 |
| ASPARAGINE | 0.0 | 0–2 |
| N-AC ASPARTIC | 0.0 | 0–20 |
| ORNITHINE | 1826.4 | 0–5 |
| GLUTAMIC ACID | 364.9 | 0–6 |
| GLUTAMINE | 0 | 0–210 |
| PIPECOLIC ACID | 0.0 | 0–1 |
| LEUCINE | 1200.1 | 0–9 |
| KETO LEUCINE | 913.8 | 0–1 |
| VALINE | 1532.7 | 0–18 |
| KETO-VALINE | 0.0 | 0–1 |
| ISOLEUCINE | 871.7 | 0–5 |
| KETO-ISOLEUCINE | 0.0 | 0–1 |
| LYSINE | 34440 | 0–35 |
| HISTIDINE | 1307 | 0–225 |
| THREONINE | 1240 | 0–45 |
| HOMOSERINE | 0.0 | 0–1 |
| METHIONINE | ******** | 0–3 |
| CYSTEINE | 10527 | 0–160 |
| HOMECYSTEINE | 0.0 | 0–1 |
| CYSTATHIONINE | 0.0 | 0–1 |
| HOMOCYSTINE | 0.0 | 0–1 |
| CYSTINE | 0.0 | 0–5 |
| PHENYLALANINE | 896 | 0–20 |
| TYROSINE | 1136 | 0–22 |
| TRYPTOPHAN | 575 | 0–25 |

This sample contained 0.00 uMoles Creatinine/7.20 ml.

TABLE 34

METABOLIC SCREENING LABORATORY
URINE ORGANIC CONSTITUENTS
FRACTION VIII, BEAR URINE
JZ4091
CONCENTRATION: THIS SAMPLE CONTAINED 0.00 uM CREATININE/mL

| PEAK # | CONSTITUENT'S BEST MATCH FROM LIBRARY* | LIB ENTRY | FIT vs 1000 | AREA % | AREA % OF CREAT |
|---|---|---|---|---|---|
| 14 | 13, JZ4051 | 2321 | 783 | 0.61 | 2309.70 |
| 18 | 13, JZ4051 | 2321 | 759 | 2.92 | 11073.36 |
| 62 | SILANE, TRIMETHYLPHENOXY- | 1122 | 877 | 0.63 | 2396.66 |
| 69 | 1,3 PROPANEDIOL DI-TMS | 1675 | 925 | 2.01 | 7601.11 |
| 74 | LACTIC ACID DI-TMS | 1510 | 907 | 0.65 | 2452.00 |
| 114 | 104, NJ3031 | 2131 | 850 | 3.43 | 12980.22 |
| 185 | BETA-LACTATE DI-TMS | 1654 | 773 | 0.42 | 1575.81 |
| 189 | 2-HYDROXY PENTANOIC ACID DI-TMS | 141 | 918 | 1.13 | 4290.31 |
| 291 | 291 | 0 | 0 | 1.55 | 5864.71 |
| 354 | DIMETHYL MALANIC ACID DI-TMS | 171 | 954 | 0.82 | 3110.44 |
| 362 | TRIMETHYLSILYL ETHER OF GLYCEROL | 273 | 938 | 0.99 | 3754.66 |
| 622 | 3-METHYL 2-PENTENEDIOIC ACID DI-TMS | 224 | 892 | 0.62 | 2366.22 |
| 687 | 3-METHYL BUTANOATE GLYCINE CONJUGATE TMS | 74 | 628 | 0.47 | 1788.05 |
| 696 | 3-METHYL 2-PENTENDIOIC ACID DI-TMS, Z- | 222 | 840 | 0.47 | 1778.00 |
| 752 | GLYCINE, N-3-METHYL-I-OXOBUTYL-N-TMS-, TRIMET | 255 | 942 | 3.62 | 13706.16 |
| 808 | METHYL D3 CREATININE TRI-TMS | 1466 | 743 | 16.38 | 62054.19 |
| 848 | 848, JZ4021 | 2317 | 887 | 3.09 | 11698.73 |
| 1104 | 1104 | 0 | 0 | 3.57 | 13521.55 |
| 1123 | 1112, M20021 | 1823 | 765 | 0.67 | 2526.55 |
| 1158 | 3,4-DIHYDROXY BENZENEACETIC ACID TRI-TMS | 531 | 834 | 0.54 | 2054.74 |
| 1196 | 1189, JZ4051 | 2322 | 961 | 3.87 | 14654.56 |
| 1211 | 1189, NU3061 | 2118 | 697 | 19.22 | 72808.71 |
| 1232 | L-GLUTAMIC ACID, N-ACETYL-N-TMS-, BIS-TMS EST | 587 | 526 | 2.22 | 8414.89 |
| 1241 | P-HYDROXYPHENYL LACTIC ACID TRI-TMS | 578 | 941 | 9.80 | 37151.69 |
| 1287 | HYDROXY PROLINE DI-TMS | 1610 | 424 | 0.72 | 2710.46 |
| 1370 | PALMITIC ACID TMS | 335 | 639 | 1.07 | 4055.54 |
| 1433 | 1481, NU3091 | 2124 | 403 | 0.46 | 1761.13 |
| 1506 | PARA-HYDROXY HIPPURIC ACID DI-TMS | 377 | 901 | 1.04 | 3941.33 |
| 1596 | PSEUDO URIDINE PENTA-TMS | 1779 | 953 | 7.00 | 26509.32 |
| 1642 | 1631, M15041 | 1802 | 795 | 8.81 | 33369.32 |
| 1740 | TREHALOSE PER-TMS | 1850 | 781 | 0.44 | 1655.34 |
| 1746 | SUCROSE OCTA-TMS | 1080 | 892 | 1.40 | 5286.62 |

*The named compound matches the sample peak with a reliability given by "FIT"/1000.

TABLE 35

QUANTIFIED TARGET PANEL
URINE ORGANIC COMPOUNDS
FRACTION IX, BEAR URINE
JZ4101:9

|  | mM/M CREATININE | Nrml Range |
|---|---|---|
| Organic Acids |  |  |
| LACTIC ACID | 856 | 0–75 |
| PYRUVIC ACID | 52 | 0–20 |
| GLYCOLIC ACID | 7 | 0–50 |
| ALPHA-OH-BUTYRIC | 1.9 | 0–1 |
| OXALIC | 0.0 | 0–25 |
| 4-OH-BUTYRIC | 0.0 | 0–1 |
| HEXANOIC ACID | 415.0 | 0–11 |
| 5-HYDROXYCAPROIC | 0.0 | 0–1 |
| OCTANOIC | 0.0 | 0–1 |
| BETA-LACTATE | 0.0 | 0–8 |
| SUCCINIC ACID | 4 | 0–20 |
| GLUTARIC ACID | 0.0 | 0–2 |
| 2-OXO-GLUTARATE | 0 | 0–210 |
| FUMARIC | 7.1 | 0–5 |
| MALEIC | 0.0 | 0 |
| MALIC ACID | 0.0 | 0–2 |
| ADIPIC ACID | 33.7 | 0–7 |
| SUBERIC ACID | 536.8 | 0–11 |
| SEBACIC ACID | 1.1 | 0–2 |
| GLYCERIC ACID | 0 | 0–4 |
| BETA-OH-BUTYRIC | 12 | 0–3 |
| METHYLSUCCINIC | 0.0 | 0 |
| METHYLMALONIC | 0 | 0–5 |
| ETHYLMALONIC | 137.0 | 0–4 |
| HOMOGENTISIC ACID | 0.0 | 0–1 |
| PHENYLPYRUVIC ACID | 110.6 | 0–1 |
| SUCCINYLACETONE | 0.0 | 0–1 |
| 3-OH-ISOVALERIC | 1.8 | 0–21 |
| PHOSPHATE | 317 | 0–3000 |
| CITRIC ACID | 136 | 0–450 |
| HIPPURIC ACID | 35604 | 0–2000 |
| URIC ACID | 4 | 0–360 |
| Nutritionals |  |  |
| KYNURENIC ACID | 297.6 |  |
| FORMIMINOGLUTAMIC | 0.00 | 0–3 |
| 4-PYRIDOXIC ACID | 0.0 | 0–9 |

TABLE 35-continued

QUANTIFIED TARGET PANEL URINE ORGANIC COMPOUNDS FRACTION IX, BEAR URINE JZ4101:9

|  | mM/M CREATININE | Nrml Range |
|---|---|---|
| PANTOTHENIC ACID | 37 | 0–30 |
| XANTHURENIC ACID | 18.4 | 0–1 |
| KYNURENINE | 19.8 | 0–1 |
| QUINOLINIC | 0.0 | 0–6 |
| OROTIC ACID | 0.00 | 0–3 |
| D-AM LEVULINIC | 20.0 | 0–18 |
| 3-METHYL HISTIDINE | 32 | 0–75 |
| NIACINAMIDE | 0.0 | 0–1 |
| PSEUDOURIDINE | 22608 | 10–220 |
| 2-DEOXYTETRONIC | 2 | 0–75 |
| P-HO-PHEN-ACETIC | 18 | 0–12 |
| XANTHINE | 6 | 0–18 |
| UROCANIC ACID | 49 | 0–3 |
| ASCORBIC ACID | 2 | 0–160 |
| GLYCEROL | 352 | 0–9 |
| Carbohydrates |  |  |
| THREITOL | 0 | 0–40 |
| ERYTHRITOL | 0 | 0–55 |
| ARABINOSE | 9 | 0–30 |
| FUCOSE | 41.0 | 0–12 |
| RIBOSE | 41.0 | 0–12 |
| XYLOSE | 3 | 0–70 |
| FRUCTOSE | 14 | 0–115 |
| GLUCOSE | 232 | 0–110 |
| GALACTOSE | 1239 | 0–200 |
| MANNOSE | 35 | 0–70 |
| N-AC-GLUCOSAMINE | 6.5 | 0–3 |
| LACTOSE | 145 | 0–60 |
| MALTOSE | 140 | 0–40 |
| XYLITOL | 0.0 | 0–15 |
| ARABINITOL | 0.0 | 0–30 |
| RIBITOL | 0.0 | 0–10 |
| ALLOSE | 6.4 | 0–10 |
| GLUCURONIC ACID | 38.1 | 0–50 |
| GALACTONIC ACID | 421 | 0–60 |
| GLUCONIC ACID | 4.9 | 0–35 |
| GLUCARIC | 2.9 | 0–5 |
| MANNITOL | 4.1 | 0–15 |
| DULCITOL | 1.0 | 0–10 |
| SORBITOL | 7.7 | 0–10 |
| INOSITOL | 3.9 | 0–12 |
| SUCROSE | 483 | 0–75 |
| Neurotransmitters |  |  |
| GABA | 8.8 | 0–1 |
| HOMOVANILLIC ACID | 6221.3 | 0–10 |
| NORMETANEPHRINE | 53.6 | 0–1 |
| VANILLYLMANDELIC | 30.3 | 0–6 |
| METANEPHRINE | 156.8 | 0–2 |
| 5-HIAA | 4791.4 | 0–6 |
| MHPG | 0.0 | 0–1 |
| ETHANOLAMINE | 211 | 10–90 |
| Amino Acids and Glycine Conjugates |  |  |
| PROPIONYL GLY | 8.7 | 0–1 |
| BUTYRYL GLYCINE | 0.0 | 0–1 |
| HEXANOYL GLYCINE | 39.1 | 0–1 |
| PHENYL PROP GLY | 0.0 | 0–1 |
| SUBERYL GLYCINE | 0.3 | 0–1 |
| ISOVALERYL GLY | 1852.0 | 0–1 |
| TIGLY GLY | 4.7 | 0–1 |
| BETA MET CROT GLY | 36.8 | 0–1 |
| GLYCINE | 614 | 0–500 |
| ALANINE | 3 | 0–130 |
| SARCOSINE | 1.2 | 0–8 |
| BETA-ALANINE | 0.0 | 0–2 |
| B-AMINOISOBUTYRIC | 232 | 0–50 |
| SERINE | 403 | 0–85 |
| PROLINE | 35.4 | 0–8 |
| HYDROXY PROLINE | 1036 | 0–75 |
| HYDROXY LYSINE | 14.3 | 0–1 |
| ASPARTIC ACID | 105.0 | 0–2 |
| ASPARAGINE | 0.6 | 0–2 |
| N-AC ASPARTIC | 41.4 | 0–20 |
| ORNITHINE | 153.8 | 0–5 |
| GLUTAMIC ACID | 53.2 | 0–6 |
| GLUTAMINE | 40 | 0–210 |
| PIPECOLIC ACID | 0.0 | 0–1 |
| LEUCINE | 62.3 | 0–9 |
| KETO LEUCINE | 533.3 | 0–1 |
| VALINE | 60.8 | 0–18 |
| KETO-VALINE | 0.0 | 0–1 |
| ISOLEUCINE | 49.9 | 0–5 |
| KETO-ISOLEUCINE | 0.0 | 0–1 |
| LYSINE | 16777 | 0–35 |
| HISTIDINE | 452 | 0–225 |
| THREONINE | 69 | 0–45 |
| HOMOSERINE | 0.0 | 0–1 |
| METHIONINE | 254.1 | 0–3 |
| CYSTEINE | 2504 | 0–160 |
| HOMOCYSTEINE | 0.0 | 0–1 |
| CYSTATHIONINE | 0.5 | 0–1 |
| HOMOCYSTINE | 4.3 | 0–1 |
| CYSTINE | 16.5 | 0–5 |
| PHENYLALANINE | 216 | 0–20 |
| TYROSINE | 73 | 0–22 |
| TRYPTOPHAN | 404 | 0–25 |

This sample contained 0.02 uMoles Creatine/7.20 ml.

TABLE 36

METABOLIC SCREENING LABORATORY
URINE ORGANIC CONSTITUENTS
FRACTION IX, BEAR URINE
JZ4101
CONCENTRATION: THIS SAMPLE CONTAINED 0.00 uM CREATININE/mL

| PEAK # | CONSTITUENT'S BEST MATCH FROM LIBRARY* | LIB ENTRY | FIT vs 1000 | AREA % | AREA % OF CREAT |
|---|---|---|---|---|---|
| 7 | 6, J14081 | 2189 | 745 | 0.67 | 179.37 |
| 10 | 13, JZ4051 | 2321 | 739 | 0.18 | 47.76 |
| 19 | 13, AK2011 | 2044 | 737 | 1.17 | 312.52 |
| 66 | SILANE, TRIMETHYLPHENOXY- | 1122 | 896 | 0.29 | 77.67 |
| 71 | ETHYL AMINE DI-TMS | 22 | 549 | 1.79 | 479.46 |
| 78 | PROPENE GLYCOL DI-TMS | 50 | 922 | 0.16 | 41.63 |
| 107 | 107, JZ4011 | 2301 | 849 | 0.14 | 37.91 |
| 117 | 104, NJ3031 | 2131 | 851 | 3.34 | 897.03 |
| 122 | 119, JQ4011 | 2243 | 902 | 0.13 | 34.73 |
| 186 | BETA-LACTATE DI-TMS | 1654 | 777 | 0.41 | 110.10 |
| 293 | 2-HYDROXY HEXANOIC ACID DI-TMS | 1682 | 784 | 3.73 | 1000.76 |
| 362 | TRIMETHYLSILYL ETHER OF GLYCEROL | 273 | 909 | 0.50 | 134.35 |
| 383 | SILANE, TRIMETHYL 1-METHYLBUTOXY- | 1112 | 493 | 0.11 | 30.42 |
| 540 | 539, JZ4041 | 2320 | 930 | 0.29 | 78.34 |
| 613 | 613 | 0 | 0 | 0.24 | 63.30 |
| 622 | 3-METHYL 2-PENTENEDIOIC ACID DI-TMS | 224 | 833 | 0.33 | 88.13 |
| 642 | 613, JZ4101 | 2370 | 711 | 1.24 | 332.62 |
| 687 | BENZENEACETIC ACID, ALPHA -- TMS-OXY, -TRIM | 246 | 889 | 1.24 | 332.20 |
| 696 | 3-METHYL 2-PENTENDIOIC ACID DI-TMS, Z- | 222 | 891 | 1.16 | 41.93 |
| 753 | HEXANEDIOIC ACID, 3-METHYL-, BIS-TMS-ESTER | 258 | 663 | 1.64 | 440.24 |
| 781 | HEXANEDIOIC ACID, 3-METHYL-, BIS-TMS-ESTER | 258 | 793 | 0.18 | 49.23 |
| 798 | METHYL D3 CREATININE TRI-TMS | 1466 | 717 | 0.11 | 30.11 |
| 809 | METHYL D3 CREATININE TRI-TMS | 1466 | 701 | 12.34 | 3310.78 |
| 821 | ORTHO-HYDROXYPHENYLACETIC ACID DI-TMS | 247 | 929 | 0.60 | 161.70 |
| 852 | 2-HYDROXY 3-PHENYL PROPIONIC ACID DI-TMS | 287 | 921 | 7.95 | 2132.51 |
| 861 | 848, JZ4021 | 2317 | 685 | 0.18 | 47.45 |
| 879 | HEPTANEDIOIC ACID, BIS-TMS-ESTER | 259 | 905 | 1.33 | 355.68 |
| 903 | PARA-HYDROXY BENZOIC DI-TMS | 202 | 868 | 0.45 | 119.54 |
| 913 | PARA-HYDROXYPHENYLACETIC ACID-DI-TMS | 1485 | 927 | 0.13 | 35.95 |
| 925 | PARA-HYDROXYPHENYLACETIC ACID-DI-TMS | 1485 | 835 | 13.82 | 3707.87 |
| 930 | 938, DQ3041 | 2164 | 757 | 0.10 | 28.08 |
| 975 | 975 | 0 | 0 | 1.18 | 316.77 |
| 986 | 985, JZ4021 | 2318 | 899 | 0.29 | 78.99 |
| 991 | 991 | 0 | 0 | 0.15 | 38.94 |
| 1001 | OCTANEDIOIC ACID, BIS-TMS-ESTER | 306 | 744 | 0.36 | 95.83 |
| 1087 | HOMOVANILLIC ACID DI-TMS | 331 | 946 | 2.49 | 667.03 |
| 1103 | 1104, JZ4091 | 2369 | 930 | 0.43 | 114.58 |
| 1116 | 1116 | 0 | 0 | 0.53 | 142.93 |
| 1125 | 1112, M20021 | 1823 | 763 | 4.82 | 1292.51 |
| 1146 | HIPPORIC ACID TMS ESTER | 103 | 903 | 1.02 | 273.29 |
| 1184 | 1189, JZ4051 | 2322 | 954 | 0.31 | 82.08 |
| 1192 | 1189, JZ4051 | 2322 | 890 | 0.33 | 89.21 |
| 1200 | 1189, NU3061 | 2118 | 705 | 0.72 | 194.06 |
| 1211 | 1189, NU3061 | 2118 | 704 | 5.65 | 1515.93 |
| 1234 | L-GLYTAMIC ACID, N-ACETYL-N-TMS-, BIS-TMS EST | 587 | 494 | 3.37 | 902.66 |
| 1243 | P-HYDROXYPHENYL, LACTIC ACID, TRI-TMS | 578 | 931 | 0.75 | 201.16 |
| 1259 | PROPANEDIOIC ACID, TMS-OXY-, BIS-TMS ESTER | 594 | 238 | 0.52 | 139.80 |
| 1273 | HYDROXY PROLINE DI-TMS | 1610 | 349 | 0.17 | 46.73 |
| 1280 | 1H-INDOLE-2-CARBOXYLIC ACID, 5-ETHYL-1-TMS- | 343 | 646 | 0.29 | 76.62 |
| 1289 | 991, JZ4101 | 2372 | 460 | 1.53 | 409.12 |
| 1332 | 1332 | 0 | 0 | 0.13 | 35.00 |
| 1354 | 1354 | 0 | 0 | 0.13 | 35.22 |
| 1364 | MANNO-ONIC ACID, LACTONE TETRA-TMS | 732 | 454 | 0.30 | 81.30 |
| 1371 | PALMITIC ACID TMS | 335 | 670 | 0.91 | 245.18 |
| 1414 | 1481, NU3091 | 2124 | 464 | 0.60 | 160.27 |
| 1426 | SILANE, TRIMETHYL 3-PHENYLPROPOXY- | 1158 | 500 | 0.19 | 50.80 |
| 1451 | BETA AMINO BUTYRIC ACID DI-TMS | 89 | 761 | 0.22 | 58.41 |
| 1411 | TRYPIOPHAN TRI-TMS | 1965 | 477 | 0.55 | 146.22 |
| 1486 | 1472, VST031 | 2031 | 771 | 4.74 | 1271.10 |
| 1509 | 5-HYDROXY INDOLE ACETIC ACID TRI-TMS | 592 | 943 | 3.19 | 856.94 |
| 1520 | STEARIC ACID TMS | 434 | 787 | 0.14 | 36.29 |
| 1573 | 6-HYDROXY-HEPTANOIC DI-TMS | 1690 | 275 | 0.30 | 79.25 |
| 1596 | PSEUDO URIDENE PENTA-TMS | 1779 | 746 | 5.92 | 1587.71 |
| 1628 | 1472, VST031 | 2031 | 799 | 0.26 | 69.56 |
| 1641 | 1631, M15041 | 1802 | 826 | 0.87 | 234.00 |
| 1673 | 1472, VST031 | 2031 | 650 | 1.73 | 464.94 |
| 1680 | 1676, JD2011 | 2001 | 624 | 0.33 | 87.91 |
| 1746 | SUCROSE OCTA-TMS | 108O | 847 | 0.31 | 83.08 |

*The named compound matches the sample peak with a reliability given by "FIT"/1000.

TABLE 37

QUANTIFIED TARGET PANEL URINE ORGANIC COMPOUNDS FRACTION X, BEAR URINE JZ4111:8

| | mM/M CREATININE | Nrml Range |
|---|---|---|
| Organic Acids | | |
| LACTIC ACID | 19433 | 0–75 |
| PYRUVIC ACID | 950 | 0–20 |
| GLYCOLIC ACID | 196 | 0–50 |
| ALPHA-OH-BUTYRIC | 14.8 | 0–1 |
| OXALIC | 36.0 | 0–25 |
| 4-OH-BUTYRIC | 0.0 | 0–1 |
| HEXANOIC ACID | 60.0 | 0–11 |
| 5-HYDROXYCAPROIC | 12.6 | 0–1 |
| OCTANOIC | 37.4 | 0–1 |
| BETA-LACTATE | 234.1 | 0–8 |
| SUCCINIC ACID | 135 | 0–20 |
| GLUTARIC ACID | 0.0 | 0–2 |
| 2-OXO-GLUTARATE | 0 | 0–210 |
| FUMARIC | 21.9 | 0–5 |
| MALEIC | 0.0 | 0 |
| MALIC ACID | 18.8 | 0–2 |
| ADIPIC ACID | 30.4 | 0–7 |
| SUBERIC ACID | 4707.2 | 0–11 |
| SEBACIC ACID | 3.0 | 0–2 |
| GLYCERIC ACID | 30 | 0–4 |
| BETA-OH-BUTYRIC | 321 | 0–3 |
| METHYLSUCCINIC | 0.0 | 0 |
| METHYLMALONIC | 0 | 0–5 |
| ETHYLMALONIC | 103.0 | 0–4 |
| HOMOGENTISIC ACID | 0.0 | 0–1 |
| PHENYLPYRUVIC ACID | 347.5 | 0–1 |
| SUCCINYLACETONE | 2.2 | 0–1 |
| 3-OH-ISOVALERIC | 1.8 | 0–21 |
| PHOSPHATE | 814 | 0–3000 |
| CITRIC ACID | 46 | 0–450 |
| HIPPURIC ACID | 5949 | 0–2000 |
| URIC ACID | 40 | 0–360 |
| Nutritionals | | |
| KYNURENIC ACID | 6.2 | |
| FORMIMINOGLUTAMIC | 0.60 | 0–3 |
| 4-PYRIDOXIC ACID | 0.0 | 0–9 |
| PANTOTHENIC ACID | 3 | 0–30 |
| XANTHURENIC ACID | 2.6 | 0–1 |
| KYNURENINE | 70.3 | 0–1 |
| QUINOLINIC | 0.0 | 0–6 |
| OROTIC ACID | 28.54 | 0–3 |
| D-AM LEVULINIC | 541.3 | 0–18 |
| 3-METHYL HISTIDINE | 216 | 0–75 |
| NIACINAMIDE | 62.7 | 0–1 |
| PSEUDOURIDINE | 10351 | 10–220 |
| 2-DEOXYTETRONIC | 41 | 0–75 |
| P-HO-PHEN-ACETIC | 254 | 0–12 |
| XANTHINE | 14 | 0–18 |
| UROCANIC ACID | 255 | 0–3 |
| ASCORBIC ACID | 1 | 0–160 |
| GLYCEROL | 11477 | 0–9 |
| Carbohydrates | | |
| THREITOL | 7 | 0–40 |
| ERYTHRITOL | 7 | 0–55 |
| ARABINOSE | 25 | 0–30 |
| FUCOSE | 379.6 | 0–12 |
| RIBOSE | 219.1 | 0–12 |
| XYLOSE | 8 | 0–70 |
| FRUCTOSE | 808 | 0–115 |
| GLUCOSE | 432 | 0–110 |
| GALACTOSE | 19 | 0–200 |
| MANNOSE | 406 | 0–70 |
| N-AC-GLUCOSAMINE | 28.8 | 0–3 |
| LACTOSE | 349 | 0–60 |
| MALTOSE | 237 | 0–40 |
| XYLITOL | 27.6 | 0–15 |
| ARABINITOL | 16.0 | 0–30 |
| RIBITOL | 0.0 | 0–10 |
| ALLOSE | 61.7 | 0–10 |
| GLUCURONIC ACID | 239.8 | 0–50 |
| GALACTONIC ACID | 400 | 0–60 |
| GLUCONIC ACID | 11.2 | 0–35 |
| GLUCARIC | 9.0 | 0–5 |
| MANNITOL | 31.5 | 0–15 |
| DULCITOL | 10.6 | 0–10 |
| SORBITOL | 55.4 | 0–10 |
| INOSITOL | 13.6 | 0–12 |
| SUCROSE | 1788 | 0–75 |
| Neurotransmitters | | |
| GABA | 24.8 | 0–1 |
| HOMOVANILLIC ACID | 1673.5 | 0–10 |
| NORMETANEPHRINE | 17.0 | 0–1 |
| VANILLYLMANDELIC | 2.6 | 0–6 |
| METANEPHRINE | 3.1 | 0–2 |
| 5-HIAA | 1026.9 | 0–6 |
| MHPG | 1.2 | 0–1 |
| ETHANOLAMINE | 679 | 10–90 |
| Amino Acids and Glycine Conjugates | | |
| PROPIONYL GLY | 16.6 | 0–1 |
| BUTYRYL GLYCINE | 0.0 | 0–1 |
| HEXANOYL GLYCINE | 444.9 | 0–1 |
| PHENYL PROP GLY | 243.3 | 0–1 |
| SUBERYL GLYCINE | 4.4 | 0–1 |
| ISOVALERYL GLY | 144.3 | 0–1 |
| TIGLY GLY | 5.7 | 0–1 |
| BETA MET CROT GLY | 353.8 | 0–1 |
| GLYCINE | 2601 | 0–500 |
| ALANINE | 1316 | 0–130 |
| SARCOSINE | 15.4 | 0–8 |
| BETA-ALANINE | 31.3 | 0–2 |
| B-AMINOISOBUTYRIC | 538 | 0–50 |
| SERINE | 2443 | 0–85 |
| PROLINE | 244.2 | 0–8 |
| HYDROXY PROLINE | 3372 | 0–75 |
| HYDROXY LYSINE | 127.6 | 0–1 |
| ASPARTIC ACID | 499.6 | 0–2 |
| ASPARAGINE | 0.2 | 0–2 |
| N-AC ASPARTIC | 13.5 | 0–20 |
| ORNITHINE | 442.4 | 0–5 |
| GLUTAMIC ACID | 6.0 | 0–6 |
| GLUTAMINE | 220 | 0–210 |
| PIPECOLIC ACID | 0.4 | 0–1 |
| LEUCINE | 337.8 | 0–9 |
| KETO LEUCINE | 1066.2 | 0–1 |
| VALINE | 417.4 | 0–18 |
| KETO-VALINE | 1.7 | 0–1 |
| ISOLEUCINE | 274.6 | 0–5 |
| KETO-ISOLEUCINE | 80.6 | 0–1 |
| LYSINE | 2599 | 0–35 |
| HISTIDINE | 203 | 0–225 |
| THREONINE | 377 | 0–45 |
| HOMOSERINE | 0.0 | 0–1 |
| METHIONINE | 20.8 | 0–3 |
| CYSTEINE | 3059 | 0–160 |
| HOMECYSTEINE | 1.0 | 0–1 |
| CYSTATHIONINE | 5.6 | 0–1 |
| HOMOCYSTINE | 59.7 | 0–1 |
| CYSTINE | 9.4 | 0–5 |
| PHENYLALANINE | 233 | 0–20 |
| TYROSINE | 190 | 0–22 |
| TRYPTOPHAN | 130 | 0–25 |

This sample contained 0.03 uMoles Creatinine/100 ml.

TABLE 38

METABOLIC SCREENING LABORATORY
URINE ORGANIC CONSTITUENTS
FRACTION X, BEAR URINE
JZ4111
CONCENTRATION: THIS SAMPLE CONTAINED 0.03 uM CREATININE/mL

| PEAK # | CONSTITUENT'S BEST MATCH FROM LIBRARY* | LIB ENTRY | FIT vs 1000 | AREA % | AREA % OF CREAT |
|---|---|---|---|---|---|
| 6 | 6, J14081 | 2189 | 675 | 0.71 | 314.00 |
| 9 | 10, STN031 | 1893 | 719 | 0.65 | 288.12 |
| 12 | 13, JZ4051 | 2321 | 561 | 0.48 | 215.50 |
| 20 | 10, M13011 | 1782 | 719 | 2.07 | 921.84 |
| 36 | 35, JZ4011 | 2300 | 847 | 0.22 | 97.76 |
| 51 | 42, M20021 | 1816 | 726 | 0.19 | 83.08 |
| 59 | 49, AK2011 | 2047 | 833 | 0.19 | 83.56 |
| 68 | SILANE, TRIMETHYLPHENOXY- | 1122 | 847 | 0.73 | 324.60 |
| 72 | ETHYL AMINE DI-TMS | 22 | 513 | 2.08 | 923.09 |
| 80 | LACTIC ACID DI-TMS | 1510 | 874 | 1.34 | 594.49 |
| 88 | BORATE TRI-TMS | 186 | 618 | 0.06 | 26.27 |
| 108 | 107, JZ4011 | 2301 | 847 | 0.20 | 90.08 |
| 118 | 104, NJ3031 | 2131 | 744 | 2.49 | 1108.84 |
| 123 | 119, JQ4011 | 2243 | 907 | 0.30 | 131.95 |
| 166 | SILANOL, TRIMETHYL-, CARBONATE 2:1 | 1429 | 647 | 0.07 | 32.24 |
| 186 | BETA-LACTATE DI-TMS | 1654 | 781 | 0.54 | 241.79 |
| 224 | 92, NA3011 | 2070 | 757 | 0.07 | 29.54 |
| 252 | 251, JZ4011 | 2302 | 848 | 0.09 | 39.70 |
| 294 | 4-METHYL 2-HYDROXY PETANOIC ACID DI-TMS | 178 | 807 | 5.30 | 2356.51 |
| 297 | 2-HYDROXY HEXANOIC ACID DI-TMS | 1682 | 786 | 3.49 | 1551.67 |
| 301 | 291, JZ4091 | 2368 | 775 | 1.56 | 693.60 |
| 336 | ETHANOLAMINE TRI-TMS | 181 | 907 | 0.13 | 59.44 |
| 349 | PEAK 459, A02011 | 1855 | 511 | 0.06 | 26.28 |
| 365 | TRIMETHYLSILYL ETHER OF GLYCEROL | 273 | 824 | 1.90 | 844.99 |
| 386 | TETRADECANOIC ACID TMS | 251 | 510 | 0.12 | 52.53 |
| 398 | GLYCINE TRI-TMS | 1539 | 869 | 0.44 | 197.40 |
| 503 | SERINE TRI-TMS | 322 | 957 | 0.51 | 228.07 |
| 540 | 539, JZ4041 | 2320 | 886 | 0.37 | 166.09 |
| 613 | 613, JZ4101 | 2370 | 855 | 0.41 | 182.98 |
| 642 | 1364, JZ4011 | 2312 | 370 | 0.69 | 307.69 |
| 686 | BENZENEACETIC ACID, .ALPHA.--TMS-OXY-, TRIM | 246 | 874 | 0.19 | 83.47 |
| 753 | HEXANEDIOIC ACID 3-METHYL-BIS-TMS-ESTER | 258 | 758 | 1.53 | 678.67 |
| 773 | SILANE, DIMETHYLPHENOXY TRIMETHYL- | 1150 | 332 | 0.12 | 55.52 |
| 781 | HEPANEDIOIC ACID, BIS-TMS-ESTER | 259 | 624 | 0.14 | 60.31 |
| 798 | METHYL D3 CREATININE TRI-TMS | 1466 | 715 | 0.04 | 18.49 |
| 809 | METHYL D3 CREATININE TRI-TMS | 1466 | 707 | 4.53 | 2013.68 |
| 822 | ORTHO-HYDROXYPHENYLACETIC ACID DI-TMS | 247 | 907 | 1.04 | 460.14 |
| 856 | 2-HYDROXY 3-PHENYL PROPIONIC ACID DI-TMS | 287 | 872 | 7.69 | 3420.08 |
| 880 | HEPTANEDIOIC ACID, BIS-TMS-ESTER | 259 | 866 | 0.95 | 460.88 |
| 907 | PARA HYDROXY BENZOIC DI-TMS | 202 | 873 | 4.41 | 1959.38 |
| 914 | PARA-HYDROXYPHENYLACETIC ACID DI-TMS | 1485 | 628 | 0.94 | 418.25 |
| 928 | PARA-HYDROXYPHENYLACETIC ACID DI-TMS | 1485 | 811 | 9.47 | 4211.72 |
| 938 | 1234, JZ4061 | 2333 | 444 | 0.07 | 32.28 |
| 946 | HEXANOYL GLYCINE DI-TMS | 1656 | 724 | 0.19 | 83.16 |
| 971 | 975, JZ4101 | 2371 | 813 | 0.23 | 100.98 |
| 976 | 975, JZ4101 | 2371 | 877 | 2.17 | 964.67 |
| 987 | 985, JZ4021 | 2318 | 756 | 0.18 | 81.73 |
| 992 | 991, JZ4101 | 2372 | 814 | 0.20 | 88.90 |
| 996 | SUBERIC ACID DI-TMS | 1633 | 520 | 0.05 | 21.95 |
| 1003 | OCTANEDIOIC ACID, BIS-TMS-ESTER | 306 | 726 | 2.12 | 940.43 |
| 1010 | 1062, NJ3051 | 2135 | 474 | 0.37 | 163.67 |
| 1015 | 561, LB1031 VALPROIC ACID METABOLITE, MSL | 1973 | 527 | 0.55 | 246.28 |
| 1031 | SILANE, TRIMETHYL PHENETHYLTHIO- | 1161 | 389 | 0.23 | 102.67 |
| 1046 | SEBACIC ACID, BIS-TMS-ESTER | 393 | 612 | 0.36 | 160.75 |
| 1060 | 975, JZ4101 | 2371 | 704 | 0.04 | 19.97 |
| 1068 | HYDROCINNAMIC ACID, P-TMS-, TRIMETHYLSILYL ES | 288 | 688 | 0.28 | 126.21 |
| 1081 | 1160, JG4021 | 2179 | 315 | 0.37 | 164.16 |
| 1088 | 1062, NJ3051 | 2135 | 770 | 1.35 | 599.54 |
| 1095 | 1332, JZ4101 | 2374 | 598 | 0.39 | 172.38 |
| 1103 | 1104, JZ4091 | 2369 | 784 | 0.06 | 26.57 |
| 1116 | 1116, JZ4101 | 2373 | 861 | 0.86 | 382.04 |
| 1124 | 1112, M20021 | 1823 | 804 | 0.34 | 149.94 |
| 1133 | 877, JK4071 | 2237 | 414 | 0.28 | 125.70 |
| 1138 | 975, JZ4101 | 2371 | 386 | 0.41 | 181.50 |
| 1145 | HIPPURIC ACID TMS ESTER | 103 | 779 | 0.13 | 59.11 |
| 1157 | ORNITHINE N5, N5 TETRA-TMS | 1536 | 836 | 0.13 | 57.72 |
| 1164 | FRUCTOSE PENTA-TMS | 881 | 660 | 0.18 | 79.07 |
| 1169 | TETRADECANOIC ACID TMS | 251 | 789 | 0.17 | 75.71 |
| 1175 | METHYL ALPHA-GLUCOSIDE TETRA-TMS | 790 | 410 | 0.30 | 134.71 |
| 1187 | 24, AK2011 | 2045 | 508 | 0.23 | 103.04 |

TABLE 38-continued

METABOLIC SCREENING LABORATORY
URINE ORGANIC CONSTITUENTS
FRACTION X, BEAR URINE
JZ4111
CONCENTRATION: THIS SAMPLE CONTAINED 0.03 uM CREATININE/mL

| PEAK # | CONSTITUENT'S BEST MATCH FROM LIBRARY* | LIB ENTRY | FIT vs 1000 | AREA % | AREA % OF CREAT |
|---|---|---|---|---|---|
| 1199 | 1189, JZ4051 | 2322 | 828 | 3.17 | 1408.37 |
| 1213 | 1189, NU3061 | 2118 | 676 | 6.41 | 2850.85 |
| 1222 | SEBACIC ACID, BIS-TMS-ESTER | 393 | 521 | 0.07 | 31.48 |
| 1227 | META-HYDROXYPHENYL ACETIC ACID DI-TMS | 248 | 274 | 0.21 | 91.70 |
| 1234 | ACETIC ACID PHENOXY-, TRIMETHYLSILYL ESTER | 66 | 481 | 0.60 | 265.32 |
| 1255 | GALACTOSE PENTA-TMS | 578 | 571 | 0.69 | 304.74 |
| 1263 | 996, JZ4061 | 2329 | 391 | 0.08 | 37.07 |
| 1279 | 1H-INDOLE-2-CARBOXYLIC ACID, 5-ETHYL-1-TMS-, | 343 | 445 | 0.11 | 49.11 |
| 1288 | INDOLE 2-ACETIC ACID 1-TMS, TMS-ESTER | 316 | 858 | 2.51 | 1117.19 |
| 1302 | GL1021, 678 | 1964 | 451 | 0.32 | 140.03 |
| 1309 | 1H-INDOLE-3-ETHANAMINEN,N, 1-BIS-TMS-5-TMS-OX | 547 | 565 | 0.27 | 119.16 |
| 1334 | 3-HYDROXYTETRADECENEDIOIC ACID 1 | 1708 | 420 | 0.13 | 59.54 |
| 1344 | 1H-INDOLE-5-CARBOXYLIC ACID, 1-TMS-,TRIMETHY | 266 | 441 | 0.38 | 170.74 |
| 1355 | D-MANNOPYRANOSE PENTA-TMS | 892 | 905 | 0.43 | 192.76 |
| 1371 | PALMITIC ACID TMS | 335 | 892 | 0.77 | 340.90 |
| 1398 | GALACTURONIC ACID PENTATMS | 915 | 629 | 0.07 | 31.57 |
| 1406 | 1246, JZ4061 | 2334 | 434 | 0.24 | 108.11 |
| 1411 | 1032, M15041 | 1796 | 335 | 0.04 | 19.48 |
| 1423 | 988, NE3031 | 2088 | 407 | 0.13 | 57.19 |
| 1443 | 1300, JZ4071 | 2356 | 465 | 0.09 | 37.89 |
| 1455 | DODECENEDIOIC ACID DI-TMS, CIS? | 1695 | 433 | 0.07 | 31.96 |
| 1489 | 1472, VST031 | 2031 | 694 | 4.88 | 2167.24 |
| 1502 | OLEIC ACID, TRIMETHYLSILYL ESTER | 1614 | 677 | 0.13 | 56.05 |
| 1509 | 5-HYDROXY INDOLE ACETIC ACID TRI-TMS | 592 | 889 | 0.36 | 159.16 |
| 1520 | STEARIC ACID TMS | 434 | 725 | 0.55 | 244.65 |
| 1529 | 982, N03031 | 2142 | 405 | 0.12 | 53.30 |
| 1537 | 3-HYDROXYDODECANEDIOIC ACID-TMS-3 | 1776 | 708 | 0.05 | 20.19 |
| 1546 | 996, G11021 | 1958 | 448 | 0.27 | 118.50 |
| 1558 | HEPTANEDIOEC ACID, 4-OXO-, BIS-TMS ESTER | 305 | 381 | 0.12 | 54.63 |
| 1562 | 1472, VST031 | 2031 | 635 | 0.07 | 32.52 |
| 1596 | PSEUDO URIDINE PENTA-TMS | 1779 | 690 | 2.10 | 933.44 |
| 1603 | 988, OK1041 | 1990 | 574 | 0.09 | 40.28 |
| 1609 | 1472, VST031 | 2031 | 552 | 0.04 | 19.08 |
| 1612 | 251, KZ4011 | 2302 | 365 | 0.06 | 24.80 |
| 1620 | D-GALACTOSE, 2-AMINO-2-DEOXY-3,4,5,6-TETRAKIS | 746 | 406 | 0.07 | 33.22 |
| 1628 | 1472, VST031 | 2031 | 729 | 0.55 | 246.19 |
| 1652 | 1472, VST031 | 2031 | 713 | 0.14 | 62.64 |
| 1664 | 1631, M15041 | 1802 | 567 | 0.09 | 41.81 |
| 1674 | 1669, P17031 | 1984 | 687 | 2.27 | 1011.28 |
| 1680 | 1472, VST031 | 2031 | 463 | 0.08 | 33.58 |
| 1686 | 1189, JZ4051 | 2322 | 252 | 0.06 | 25.53 |
| 1692 | 1073, RT1051 | 2040 | 395 | 0.05 | 22.18 |
| 1701 | 2-HYDROXYTETRADECENEDIOIC ACID | 1704 | 385 | 0.08 | 36.13 |
| 1728 | 533, LB1031 VALPROIC ACID METABOLITE, MSL | 1972 | 409 | 0.04 | 19.96 |
| 1746 | SUCROSE OCTA-TMS | 1080 | 888 | 0.73 | 324.31 |
| 1795 | LACTOSE OCTA-TMS | 1854 | 785 | 0.08 | 36.36 |
| 1839 | 1785, YD1011 | 1875 | 414 | 0.06 | 25.81 |

*The named compound matches the sample peak with a reliability given by "FIT"/1000

Further Purification of MNC in Friction VI Using HPLC

Fraction VI was further purified using HPLC. After lyophilization and reconstitution in methanol, aliquots of Fraction VI were loaded onto a HPLC using a $C_{18}$ column. A gradient of 0.1M ammonium formate and a 9:1 mixture of acetonitrile/water was the solvent system used for further separation of Fraction VI. Four peaks were visualized using a UV-Vis detector. Based on the increased absorbance at 220 nm, 230 nm, and 280 nm, four fractions were collected.

Peak 3 was further purified by HPLC using an isocratic solvent system. A representative tracing from HPLC of repetitive injections of Peak 3 recorded at wavelengths of 220 nn, 230 nm, and 280 nm. Both peaks were collected and labeled as 3A and 3B respectively.

Peak 4 was further purified by HPLC using a gradient system. It was detected by increased UV absorbance readings at 220 nm, 230 nm, and 280 nm. Peak 4 was separated into two peaks and collected as Fractions 4A and 4B.

Submission of HPLC Fractions for Analysis by Nuclear Magnetic Resonanl (NMR) and Mass Spectrometry (MS)

Fractions labeled as 3A and 3B were submitted to NMR and MS using chemical ionization and electron ionization. The molecular weight of Fraction 3A is estimated to be 279. Interpretation of the NMR spectra suggests a phenolic compound. Fraction 3B has a molecular weight of 209 with an empirical formula consisting of $C_{10}H_{11}NO_4$. The substance para-hydroxyphenylacetylglycine has a similar molecular weight of 209. However, NMR data do not support the theory that para-hydroxyphenylacetylglycine exists in the MNC complex. An ester structure found by NMR in the MNC complex is not found in the structure of para-hydroxyphenylacetylglycine. Also, para-hydroxyphenylacetylglycine has been only detected in Fraction VI.

Data from NMR support the conclusion that Peak 4 contains both an indole structure and a phenol structure.

Summary

1. MNC from Fraction VI has been further purified using gradient and isocratic HPLC into compounds 1, 2, 3A, 3B, 4A, and 4B.

2. The molecular weight of compound 3B is known at 209 ($C_{10}H_{11}NO_4$),

3. One structure with a molecular weight of 209 has been found in Fraction VI. It has been identified as para-hydroxyphenylacetylglycine.

4. However, a unique compound with a phenylester structure and having an empirical formula of $C_{10}H_{11}NO_4$ best corresponds to the data accumulated from NMR.

5. Thus, a unique substance (which is part of the MNC complex associated only with the denning phenomenon) is found in Fraction VI. This unique substance also contains significant biopotential for stimulation of osteoblasts.

Anticipated Treatment Results

Based upon studies with guinea pigs, bone cultures, black bears, and polar bears, the anticipated results of BDI treatment in humans follow.

Osteoporosis

Successful treatment of females or males suffering from osteoporosis or prevention of bone loss in them or in astronauts will be due to stimulation of osteoblasts (the cells that form bone), inhibition of resorption activity of osteoclasts, or simiultaneous effects of osteoblasts and osteoclasts.

Thus, BDI becomes a potent, naturally occurring component to not only prevent osteoporosis but to increase size and strength of bone and successfully treat the debilitating condition of Osteoporosis.

These changes may be evaluated by a general medical examination and optional diagnostic evaluations including radiographic assessment, measurement of the density of vertebral and other bones, prevention of bone fractures, and special assessment of skeletal remodeling activity.

Kidney Disease

Patients with chronic kidney disease or end stage renal failure may be treated so that the recycling of excess urea back into protein would result in the symptoms of kidney failure being reduced or abolished, to the extent that dialysis or kidney transplantation would not be needed.

Burns and Trauma

The prevention of excessive loss of protein from non-involved muscle and other tissues would treat patients with severe burns and trauma.

Muscle Atrophy

This treatment may maintain muscle mass in humans as they age and may prevent loss of muscle tissue in astronauts.

Obesity and Other Eating Disorders

The interfacing of increasing deposition of healthy lean tissue while eating less would have a pronounced favorable effect on the treatment of obesity in human beings. When the effective dose of BDI is adjusted for safety and to a degree that it promotes less food intake to a point of complete absence while preserving lean tissues, treatment of one of the most resistant disorders of human beings may be accomplished.

An anticipated treatment result, based on studies of hyperphagic black bears, would be to stimulate food intake in humans suffering from poor food intake such as anorexia nervosa.

General Health

In humans, the overall effects of BDI are expected to enhance general health while substantially reducing cost of health care.

Predictability and Correlatability of Comparable Results In Humans

While in vivo tests have not been made with regard to bone remodeling by the bear derived isolate of claim 1, in vitro tests have been done. Such in vitro tests are set forth in a recent April 1994 draft publication by the FDA. The publication is entitled "Guidelines for Pre-Clinical and Clinical Evaluation of Agents Used in the Prevention or Treatment of Post Menopausal Osteoporosis". The draft was prepared by The Division of Metabolism and Endocrine Drug Products of the FDA, as indicated in April of 1994. The following shows a comparison between the guidelines (Page 4, Section IV) and results achieved with BDI.

| Suggested FDA Guidelines | BDI Test Results |
|---|---|
| 1. At least one biochemical marker of bone resorption. | 1. BDI isolated from summer fasting urine inhibits the production of tartrate resistant acid phosphatase in mouse calvaria organ cultures. Tartrate resistance acid phosphatase is produced by osteoclasts and serves as a sign of bone resorption (Lau, et al., 1987; Delmas, 1988). |
| 2. At least one biochemical marker for bone formation. | 2. When added to an organ (bone) culture of mouse calvaria, BDI isolated from winter denning urine or from summer fasting urine produced a statistically significant production of alkaline phosphatase which represents stimulation of osteoblasts (Aurback, Marx, et al., 1992; Delmas, 1988, 1993; Mundy, Roodman, 1991; Parviainen, Pirskanen, 1991; Stein, Lian, 1990, 1993; Quarles, Yokay, et al., 1992). |
| 3. That alkaline phosphatase is the suggested biochemical marker for bone formation. | 3. When BDI was broken down into ten individual fractions, fractions V, VI, and VII proved to be the most potent in stimulating statistically significant production of alkaline phosphatase by osteoblasts located in the bone of mouse calvaria. |
| 4. A suggested biochemical marker of bone resorption is urinary pyridinium crosslinks. | 4. Rather than using an indirect method to assess bone resorption, our studies have shown that BDI inhibits resorption in two ways the conversions of bone marrow monocytes into osteoclasts, and by the inhibition of osteoclasts already functioning in bone resorptive cavities. |
| 5. Measurement of serum osteocalcin (a specific marker of bone formation) is encouraged. | |

The foregoing results confirm in vitro bone remodeling consistent with the FDA outlined guidelines. Ongoing in vivo studies have confirmed the following.

Pre-Clinical in vivo Studies

| | |
|---|---|
| 1. Study conducted in an in vivo model such as the ovariectomized, osteoporotic rat. | 1. When compared with the untreated, osteoporotic ovariectomized rat, ovariectomized rats that had been treated with DBI showed a 16-fold increase in bone mineral density of the femoral bone and a 4-fold increase in the vertebral bones when compared with bone mineral density of humans receiving therapeutic estrogen therapy over the same or trial period. |

| -continued |  |
|---|---|
| 2. Histomorphometry or measurement of serum osteocalcium (a specific marker of bone formation) is encouraged. | 2. Histomorphometry of the femoral and vertebral bones from the DBI treated, ovariectomized, osteoporatic rats is now underway. |

The foregoing in vivo studies correlate with the FDA guidelines.

In addition, the subject matter of claim 1 has the ability to modulate the urea to creatinine ratio in urine of the guinea pig to values of 10 or less. Thus, tests were affirmative, and indicative of an increased ability of the guinea pig to recycle urea (Table 16). Bone mineral density in ovariectomized rats increased when those rats were treated with the subject matter of claim 1.

Nelson, Jones, et al. (1975) showed that urea is continually produced in the denning bear. Since the bear doesn't urinate, urea levels in blood, if unchecked, would result in high levels of urea (uremia) and death. Ahlquist, Nelson, et al. (1984) and Wolfe, Nelson et al. (1982, 1982a) showed that uremia is prevented by recycling the newly formed urea almost immediately back into protein from which it came. Nitrogen from urea was split off and attached to glycerol released from stored fat in adipose tissue. The newly formed amino acids were then incorporated in proteins such as albumin and fibrinogen.

Nelson, Beck, et al. (1984) showed that the rapid recycling of urea resulted in a decline of the level of urea in blood. When expressed as a ratio of urea to creatinine, the ratio decreased from 20 or more to less than 10. Such ratios were only found in denning bears who were not drinking or urinating. In catheterized urine specimens of denning bears, Nelson, Wahner, et al. (1973) showed when urea recycling was in process, the urea to creatinine ratio in urine was also reduced to values less than 10.

When BDI was injected into guinea pigs, urine U/C was decreased to values less than 10 indicative of similar urea recycling in guinea pigs as shown by denning bears. A strong indicator of suitability of bear originated materials for pharmacologic use in humans is the use of the bile salt produced by the bear, ursodeoxycholic acid (UDCA).

1. UDCA is safe and effective therapy for patients with cholesterol gall stones (Rubin, Kowalski, et al., 1994).
2. UDCA currently offers the best combination of efficacy and lack of side effects in treatment of primary biliary cirrhosis and reduces the need for liver transplants (Lim, Northfield 1994; Poupon, Poupon, et al., 1994).
3. UDCA improves liver function in primary sclerosing cholangitis of the liver (Jazrawi, De Coestecker, et al., 1994).
4. UDCA is a safe, well-tolerated, and efficacious treatment of refractory chronic graft versus host disease of the liver occurring in patients receiving bone marrow transplants (Fried, Murakawi, et al., 1992).
5. UDCA is a bear derivative acceptable and approved to be administered to humans.

Accordingly, it is extrapolated that if one bear derivative is administered pharmaceutically to humans as a pharmacological product, another bear derivative will be similarly acceptable. This acceptability is reinforced by the cited tests with guinea pigs.

In summary, the conclusion reached after many years of study, observation of the phenomenon of bears, and predicated upon numerous publications set forth in the bibliography filed with this application, the predictability and correlatability to comparable results when administered to humans is present within the confines of the current disclosure.

OTHER INVESTIGATIONS

In addition to those described, investigations relating the close proximity of the BDI isolate with other normally appearing metabolic substances suggests that they are required to achieve action. Thus, BDI, the bear derived isolate alone, may require other metabolites to exert its action. Further portions of the entirety of the isolate may be combined or absorbed into these substances to exert action. This equivalency may be a function of these interactions and substantially produce the same result.

Summary of Present Discovery and Areas for Further Research

Already achieved as set forth above is the discovery of how the bear forms bone, even though existing in a state similar to post-menopausal women. The discovery reveals that BDI inhibits bone resorption by inhibiting the maturation of osteoclasts from bone marrow monocytes and by directly inhibiting functioning osteoclasts. The discovery has confirmed that a unique feature of BDI is that rather than inhibiting osteoblasts as current drugs do (and thus reducing bone production), BDI independently stimulates osteoblasts to form bone. Even though the bear inhibits osteoclasts, at the same time it independently stimulates osteoblasts to form bone. This novel, unique approach of direct osteoblast stimulation by BDI has been shown in cell and organ bone cultures. When current drugs on the market inhibit bone resorption by osteoclasts, osteoblast numbers and activity are also inhibited. BDI's unique abiltiy to directly stimulate osteoblastic proliferation is demonstrated. Moreover, BDI directly stimulates fibroblastic activity which involves the matrix formation and production of bone stimulating factors. Again, no drugs on the market have this action. Finally, BDI stimulates bone formation in the ovariectomized rat, a model similar to post-menopausal women.

GC/MS has established the identifiable ingredients present in BDI. Using countercurrent chromatography (CCC), fractions were developed that separated BDI into semi-purified fractional components that affect osteoblasts, osteoclasts, and fibroblasts. These discoveries include the potent Fractions V, VI, and VII that stimulate osteoblast and fibroblast proliferation and bone formation by osteoblasts. This is to the exclusion of the inhibition of osteoblastic activity of BDI found in Fraction III. Moreover, the discoveries of the constitutents of Fractions V, VI, and VII by first producing them by CCC and then by determining their composition and concentration by GCIMS has led to further investigations. This includes the fact that bone resorption inhibiting activity of BDI is found mainly in the first three fractions of BDI as produced by CCC. Also, Fraction III inhibits osteoblasts directly.

Additionally, the potency of Fractions V, VI, and VII on forming bone in the osteoporotic rat can be calculated from the in vivo rat studies, the In vitro organ cultures of mouse calvarial bone and the cell cultures of osteoblasts.

Future Investigations

What is thus required is the following:

The combined potency of Fractions V, VI, and VII of BDI needs to be determined. This may result in the discovery of a unique substance that orchestrates all of the bone forming activity of BDI or in the fact that BDI represents a novel and unique combination of previously known as well as recently discovered new compounds. This substance or combination will be tested using in vitro and in vivo methods. This novel and unique substance or combination of substances will be synthesized and tested for bone forming activity in a model of the post-menopausal human, ovariecomized rats.

Other Bear Species

The effects of BDI as related to urea recycling extend from the black bear to include grizzly and polar bears. Both of these species demonstrate urea recycling as shown by a low blood urea to creatinine ratio when not drinking water or eating snow. No other mammal has this ability. If not drinking water, or if water is withheld, all other animals show an increase in blood urea and dehydration. Their urea to creatinine ratio rises above 20 and death will occur if water is not taken. Because of the effective urea recycling process, when not drinking or eating, black, grizzly, and polar bears protect their lean body mass, behave normally, and can be physically active. Since BDI induces denning phenomenon in guinea pigs (including urea recycling), BDI can be predicted to be similar in effects if obtained from urine or blood from grizzly or polar bears.

Scope of the Invention

It will be understood that within the scope of the invention as expressed in the appended claims, various changes in the details and materials which have been herein described and illustrated in order to explain the nature of the invention, may be made by those skilled in the art within the principle and scope of the invention as expressed in the appended claims.

What is claimed is:

1. A composition of matter comprising pharmacological properties and which is a deproteinated isolate which has been obtained from a sample of urine or serum taken from a fasting bear from which food has been withheld for two weeks or more, which sample has been subjected to deproteination, then the deproteinated isolate having the pharmacological properties of inducing, when injected into another mammal, conditions observable in denning black bears including reduced heart rate, temperature reduction, or a tranquility distinguishable from normal behavior.

2. A method for obtaining an isolate form the blood or urine of a fasting bear which bear has not eaten for two weeks or more, such isolate being sufficiently free of impurities for repeated administration to mammals to induce activity of a kind observed in denning bears comprising the steps of:

drawing a sample of blood or urine from said bear, deproteinating and extracting the isolate from such sample with organic solvents, further purifying the presence of said isolate by countercurrent chromatography, flash column chromatography, preparative thin layer chromatography, and/or high performance liquid chromatography, and testing the purity of the isolate so obtained by TLC and/or chemical or spectroscopic detection.

3. A deproteinated urine or serum of a fasting bear which has not eaten for two weeks or more comprising a therapeutic compound producing, in any combination, the following behavior in another mammal:

tranquility, or reduced heart rate, or increased osteoblastic activity, or decreased osteoclastic activity.

4. A composition of matter having the characteristics of deproteinated urine or serum of a fasting bear, which bear has not eaten for two weeks or more and capable of producing the following behavior in a guinea pig injected with said composition produces the following:

tranquility, or reduced heart rate, or increased osteoblastic activity, or decreased osteoclastic activity.

5. A composition of matter having the characteristics of deproteinated urine or serum of a fasting bear, which bear has not eaten for two weeks or more and capable of producing when injected in a guinea pig:

enhanced bone remodeling.

6. A composition of matter having the characteristics of deproteinated urine or serum of a fasting bear, which bear has not eaten for two weeks or more and capable of producing when injected in an ovariectomized rat:

enhanced bone formation.

7. A composition of matter comprising the deproteinated urine or serum of a denning black bear, which denning black bear neither eats, drinks, urinates, or defecates for lengthy periods of time having the following properties:

soluble in water, methanol, and 1-butanol, insoluble in less polar organic solvents including ethyl acetate, chloroform, toluene, and hexane, stable at room temperature for four days or more, heat resistant to 65° C., and stable when frozen in a light resistant container under nitrogen gas which, when injected into a guinea pig, is capable of producing reduced heart rate, reduced temperature, or observable tranquility differing from normal.

8. The composition of matter according to claim 7 which, when subjected to in vitro analysis, produces the following:

increased osteoblastic activity, or decreased osteoclastic activity, or increased fibroblastic activity.

9. The composition of matter according to claim 7 which, when subjected to in vitro analysis with ovariectomized rats, produces the following:

increased osteoblastic activity, decreased osteoclastic activity, or both.

10. A pharmacological composition of matter comprising the capability of enhancing bone formation in ovariectomized rats taken from a substance present in the blood or urine of fasting bears, which when fasting are unique in that they have not eaten for two weeks or more, said composition including a quantity of resorptive form of 24,25-dihydroxyvitamin $D_3$ which stimulates bone formation.

11. The method of producing a pharmaceutical composition from the blood or urine of a fasting bear, which bear has not eaten for two weeks or more, comprising the steps of:

harvesting the blood or urine from said bear, using counter current chromatography (CCC) to divide the thus withdrawn composition from the bear into 10 factions; and isolating the inhibitors of bone formulation in Fractions I, II, and III, and purifying the Fractions V, VI, and VII that contain potent stimulation of bone formation, both in the stimulation and proliferation of osteoblast and fibroblasts as well as containing inhibitors to osteoclastic formation and direct inhibitors of resorption by osteoclast.

12. A composition of matter having the characteristics of deproteinated urine of a fasting bear, which bear has not eaten for two weeks or more and capable of producing the following phenomena in a guinea pig when injected with said composition produces the following:

a decrease in the urea creatinine ratio to a level of 10:1 or less.

13. A composition of matter having the characteristics of deproteinated urine of a fasting bear, which bear has not eaten for two weeks or more, and which bear during the period of two weeks or more has reduced its urea to creatinine ratio by at least 25%, capable of producing the following phenomena in a guinea pig when injected with said composition:

a reduction in the urea creatinine ratio to a level of 10:1 or less.

14. A composition of matter having the characteristics of deproteinated urine of a fasting bear, which bear has not eaten for two weeks or more, and which produces the following phenomena when injected into a guinea pig:

a reduction in the urea creatinine ratio of said Guinea pig from the pre-injection urea creatinine ratio of the subject Guinea pig.

15. A composition of matter having the characteristics of unprocessed urine of fasting bears, which bears have been fasting for at least two weeks, but without withholding water and when subjected to alkaline phosphatase as a means of evaluating osteoblastic activity, exhibits and increase in osteoblastic activity of at least 50% above a control.

16. A composition of matter having the characteristics of a bear derived isolate (BDI) which is isolated from fasting black bears which decreases osteoclastic activity while simultaneously stimulating osteoblastic activity thereby promoting enhanced bone remodeling.

17. A method of preparing a bear derived isolate (BDI) from the urine of a bear which either dens without eating, drinking or defecating for weeks on end or when the bear has been fasting for at least two weeks but water is not withheld which, when subjected to tests which are in vivo studies with guinea pigs, in vivo studies with rats, in vitro organ studies of calaverial mass bone, and in vitro studies of prevention and proliferation of cells that resorb bone and stimulation of proliferation of cells that form bones using cell cultures of monocytes, osteoclasts, osteoblasts, and fibroblast and when tested by the various said tests produce the following phenomena:

reduced heart rate;

reduced temperature;

reduced blood pressure;

reduced osteoclastic activity;

increased osteoblastic activity; and a decrease in the urea/creatinine ratio.

18. A composition of matter having the characteristics of deproteinated urine or serum of a fasting bear, which bear has not eaten for two weeks or more and capable of producing the following behavior in a guinea pig injected with said composition produces the following:

tranquility, or reduced heart rate, or increased osteoblastic activity, or decreased osteoclastic activity, or produces at least one of the phenomena as exhibited by a denning black bear.

19. A method of preparing a bear derived isolate (BDI) from the urine of a bear which either dens without eating, drinking or defecating for weeks on end or when the bear has been fasting for at least two weeks but water is not withheld which, when subjected to tests which are in vivo studies with guinea pigs, in vivo studies with rats, in vitro organ studies of calaverial mass bone, and in vitro studies of prevention and proliferation of cells that resorb bone and stimulation of proliferation of cells that form bones using cell cultures of monocytes, osteoclasts, osteoblasts, and fibroblast and when tested by the various said tests produce the following phenomena:

increased fibroblastic activity.

20. A composition of matter having the characteristics of deproteinated urine or serum of a fasting bear, which bear has not eaten for two weeks or more and capable of producing the following behavior in another mammal, conditions observable in denning black bears including:

reduced heart rate, reduced temperature, tranquility distinguishable from normal behavior.

21. A composition of matter having the characteristics of deproteinated urine or serum of a fasting bear, which bear has not eaten for two weeks or more and capable of producing the following behavior in another mammal, injected with said composition produces the following induces behavioral characteristics of a denning black bear.

22. A composition of matter having the characteristics of a deproteinated urine or serum sample of a fasting bear, which bear has not eaten for two weeks or more treated as follows:

first deproteinating the sample, second separating the sample chromatographically into fractions, and third testing the fractions for a purity of isolation which permits the isolate when administered to a mammal other than a bear to induce behavioral characteristics of a denning bear.

* * * * *